United States Patent [19]

Shirasaka et al.

[11] Patent Number: 5,262,411
[45] Date of Patent: Nov. 16, 1993

[54] ISOCEPHEM DERIVATIVES, AND ANTIMICROBIAL COMPOSITION CONTAINING THE DERIVATIVES

[75] Inventors: Tetsuhiko Shirasaka, Kawagoe; Hiroshi Ishikawa; Koichi Yasumura, both of Otsu; Koichiro Jitsukawa, Ashiya; Sachio Toyama; Hidetsugu Tsubouchi, both of Otsu; Kimio Sudo, Shiga; Koichi Tsuji, Otsu, all of Japan

[73] Assignee: Otsuka Pharmaceutical Co., Ltd., Tokyo, Japan

[21] Appl. No.: 635,441

[22] Filed: Dec. 28, 1990

[30] Foreign Application Priority Data

Dec. 29, 1989 [JP] Japan ................................. 1-340044
Feb. 5, 1990 [JP] Japan ................................. 2-26559
Apr. 9, 1990 [JP] Japan ................................. 2-94648
Jun. 28, 1990 [JP] Japan ................................. 2-171981

[51] Int. Cl.$^5$ .................... C07D 417/12; A61K 31/54
[52] U.S. Cl. .................................. 514/210; 540/214; 540/301; 540/222; 540/227
[58] Field of Search ................ 514/214, 210; 540/215, 540/222, 301

[56] References Cited

U.S. PATENT DOCUMENTS 4,908,359  3/1990  Costerousse et al. ................ 540/214

FOREIGN PATENT DOCUMENTS 0215435  9/1986  European Pat. Off. .
0282365  2/1988  European Pat. Off. .

OTHER PUBLICATIONS

Chemical Abstracts, vol. 111, No. 1, Jul. 3, 1989 Columbus, Ohio, USA p. 682; ref. No. 7140Q and JP-A-6-3-313788 (Otsuka Pharm. Co. Ltd.), Dec. 21, 1988.

Primary Examiner—Nicholas S. Rizzo
Attorney, Agent, or Firm—Sughrue, Mion, Zinn, Macpeak & Seas

[57] ABSTRACT

There is provided a cephalosporin derivative represented by the general formula (1):

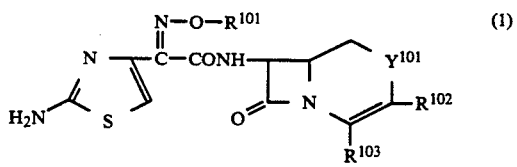

wherein $R^{101}$, $R^{102}$, $R^{103}$ and $Y^{101}$ are as difined; the general formula (2):

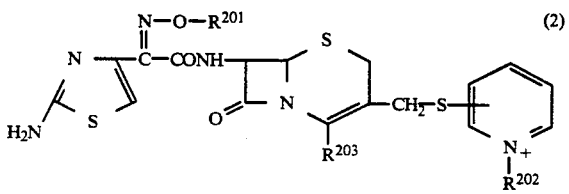

wherein $R^{201}$, $R^{202}$ and $R^{203}$ are as defined above; the general formula (3):

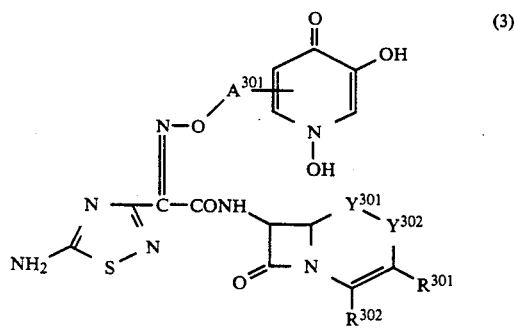

wherein $R^{301}$, $R^{302}$, $Y^{301}$, $Y^{302}$ and $A^{301}$ are as defined; or pharmaceutically acceptable salt thereof. The compound is useful as an active ingredient of antimicrobial agent.

14 Claims, No Drawings

ISOCEPHEM DERIVATIVES, AND ANTIMICROBIAL COMPOSITION CONTAINING THE DERIVATIVES

FIELD OF THE INVENTION

This invention relates to novel cephalosporin derivatives, the process for preparing the same, and antimicrobial composition containing the derivatives.

BACKGROUND OF THE INVENTION

Among antimicrobial cephalosporin derivatives, those wherein the 2-position atom of the isocephem skeleton is a sulfur atom have been described in the Japanese Unexamined Patent Publication No. 201191/1988, those wherein the 2-position atom is an oxygen atom have been described in the Japanese Unexamined Patent Publication No. 152383/1987, and those wherein the 1-position atom is an oxygen atom have been described in the Japanese Unexamined Patent Publication No. 313788/1988 etc.

However, the cephalosporin derivatives in the present invention are structurally different from the known cephalosporin derivatives.

SUMMARY OF THE INVENTION

The object of the present invention is to provide novel cephalosporin derivatives having antimicrobial activity.

Another object of this invention is to provide a pharmaceutical composition containing the cephalosporin derivatives of this invention.

An further object of this invention is to provide the process for preparing the cephalosporin derivatives of this invention.

Namely the cephalosporin derivatives or pharmaceutically acceptable salt of this invention are represented by the general formula (1), (2), or (3).

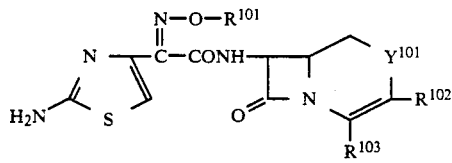
(1)

wherein, $R^{101}$ represents a lower alkyl group, carboxy-lower-alkyl group, or a group represented by the general formula:

$-A^{101}\text{-}R^{104}$ (wherein $A^{101}$ is a lower alkylene group which may have a carboxy groups, and $R^{104}$ represents one of the following groups:

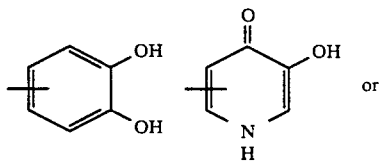 or

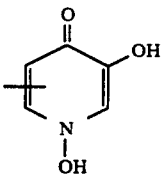

$R^{102}$ is a hydrogen atom, lower alkyl group, or a heterocyclic thiomethyl group having 1 to 4 hetero atoms selected from the group consisting of nitrogen and sulfur atoms, and the heterocyclic moiety of the heterocyclic thiomethyl group may have lower alkyl group, carboxy-lower-alkyl group, hydroxy-lower-alkyl group, amino group, or the group represented by the general formula:

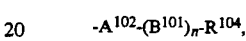
$-A^{102}\text{-}(B^{101})_n\text{-}R^{104}$, wherein $A^{102}$ is a lower alkylene group and $B^{101}$ is a carbonyl group or a group represented by:

—CONHNHCO—;

n is 0 or 1; and $R^{104}$ is the same as defined above), $R^{103}$ is a carboxy group or carboxylate group, and $Y^{101}$ is an oxygen atom or a sulfur atom; provided that at least either $R^{101}$ or $R^{102}$ described above is sure to include $R^{104}$.

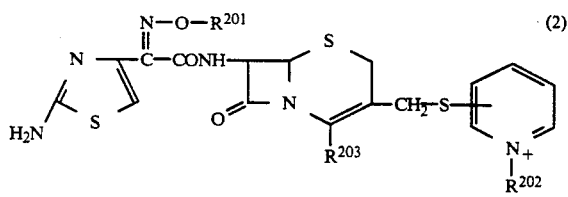
(2)

[wherein $R^{201}$ is a $C_1$-$C_6$-alkyl group or carboxy-$C_1$-$C_6$-alkyl group, $R^{202}$ is a group represented by the general formula:

$-A^{201}\text{-}(B^{201})_n\text{-}R^{204}$ (wherein $A^{201}$ is a $C_1$-$C_6$-alkylene group, $B^{201}$ is a carbonyl group or the group:

—CONHNHCO—, n is 0 or 1, and $R^{204}$ is either one of the following groups:

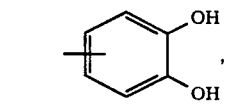

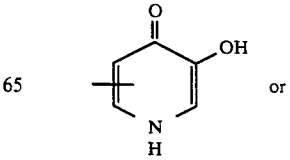 or

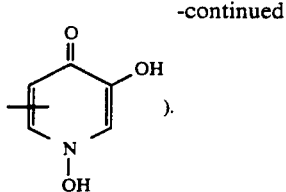

and $R^{203}$ is a carboxy group or carboxylate group,

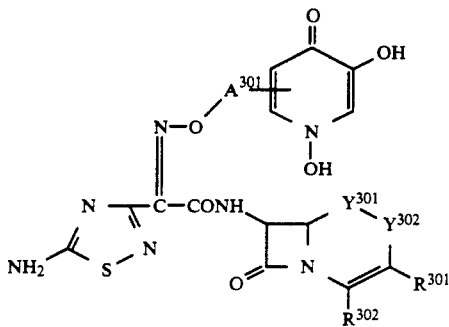

(3)

wherein, wither $Y^{301}$ or $Y^{302}$ is a methylene group and the other is a sulfur atom; $A^{301}$ is a lower alkylene group; $R^{301}$ is a heterocyclic thiomethyl group having 1 to 4 hetero atoms selected from the group consisting of nitrogen and sulfur atoms, and the heterocyclic moiety of the said heterocyclic thiomethyl group may have lower alkyl group, carboxy-lower-alkyl group, carboxy group, or hydroxy group; and $R^{302}$ is a carboxy group or carboxylate group.

The compounds of this invention represented by the general formula (1), (2) or (3) have antimicrobial activity against a broad spectrum of gram-positive and gram-negative bacteria, particularly high activity against gram-positive bacteria such as Staphylococcus aureus FDA-209-P, Streptococcus pneumoniae, and Corynebacterium diphtheriae. The compounds have effective antimicrobial activity also against non-glucose-fermenting bacteria such as Pseudomonas aeruginosa. Especially, compound (1) has high antimicrobial activity against Pseudomonas aeruginosa. In addition, the compounds of this invention are characterized by the good absorption into organisms, long duration of the efficacy, and low toxicity, being very effective even against resistant bacteria and clinical isolates. Moreover, the compounds of this invention are highly stable, being excellent with respect to their absorption and elimination. Namely their renal excretion and their distribution into the bile are high. Their distribution to the organs including the lung is also high. The difference between the minimum inhibitory concentration and minimum bactericidal concentration is small, and side effects such as immunosuppressive action and allergic action are rarely encountered.

Therefore the compounds of this invention are useful as a therapeutics agent for or diseases caused by various pathogenic bacteria in human, animals, fish, and the like, and also useful as external antimicrobials and disinfectants for medical instruments.

DETAILED DESCRIPTION OF THE INVENTION

The groups specified in this specification are described in more detail in the following.

The lower alkyl groups include alkyl groups having 1 to 6 carbon atoms, such as methyl, ethyl, propyl, isopropyl, butyl, isobutyl, tertiary butyl, pentyl and hexyl.

The carboxy-lower-alkyl groups include those of which alkyl moiety has 1 to 6 carbon atoms, such as carboxymethyl, 2-carboxyethyl, 3-carboxypropyl, 4-carboxybutyl, 5-carboxypentyl, and 6-carboxyhexyl.

The lower alkylene groups include those having 1 to 6 carbon atoms, such as methylene, methylmethylene, ethylene, dimethylmethylene, trimethylene, 1-methyltrimethylene, 2-methyltrimethylene, 2,2-dimethyltrimethylene, tetramethylene, pentamethylene and hexamethylene.

The heterocyclic moieties of the heterocyclic thiomethyl groups include unsaturated heterocyclic groups having 1 to 4 heteroatoms selected from the group consisting of nitrogen atom and sulfur atom, being exemplified by 5-membered or 6-membered monocyclic-heterocyclic groups such as 1,3,4-thiadiazolyl, 1,2,3-thiadiazolyl, 1,2,4-thiadiazolyl, 1,2,4-triazolyl, 1,2,3-triazolyl, 1,3,4-triazolyl, tetrazolyl, pyridyl, 1,2-thiazolyl, 1,3-thiazolyl, imidazolyl, and 1,2,4-triazinyl.

The hydroxy-lower-alkyl groups include hydroxymethyl, 1-hydroxyethyl, 2-hydroxyethyl, 2-hydroxypropyl, 3-hydroxypropyl, 2-hydroxy-1,1-dimethylethyl, 4-hydroxybutyl, 5-hydroxypentyl, 6-hydroxyhexyl, 1,2-dihydroxyethyl, and 2,3-dihydroxypropyl.

In the following, representative examples of the compounds of this invention represented by the general formula (1) are listed in Table 1, those represented by the general formula (2) in Table 2, and those represented by the general formula (3) in Table 3.

TABLE 1

| | $R^{101}$ | $R^{102}$ | $R^{103}$ | $Y^{101}$ | Remarks |
|---|---|---|---|---|---|
| 1 | ![structure] | ![structure] | —COOH | S | |
| 2 | ![structure] | ![structure] | —COOH | S | |

TABLE 1-continued

| | $R^{101}$ | $R^{102}$ | $R^{103}$ | $Y^{101}$ | Remarks |
|---|---|---|---|---|---|
| 3 | 6-(CH₂-)-3-hydroxy-1-hydroxy-4(1H)-pyridinone | —CH₃ | —COO⁻ | S | Sodium salt |
| 4 | —C(CH₃)₂—COOH | —CH₂S—(4-pyridinio)—N⁺—CH₂—C(=O)—(3,4-dihydroxyphenyl) | —COO⁻ | S | |
| 5 | —C(CH₃)₂—COOH | —CH₂S—(4-pyridinio)—N⁺—CH₂—C(=O)—NH—NH—C(=O)—(3,4-dihydroxyphenyl) | —COO⁻ | S | |
| 6 | —CH₂—(3,4-dihydroxyphenyl) | —CH₂S—C(=N—N=C(CH₃))—S— (1,3,4-thiadiazole) | —COOH | S | |
| 7 | —C(CH₃)₂—COOH | —CH₂S—(4-pyridinio)—N⁺—CH₂—(5-hydroxy-4-oxo-1H-pyridin-2-yl) | —COO⁻ | S | |
| 8 | 6-(CH₂-)-3-hydroxy-1-hydroxy-4(1H)-pyridinone | H | —COOH | S | |
| 9 | 6-(CH₂-)-3-hydroxy-1-hydroxy-4(1H)-pyridinone | —CH₂S—(tetrazol-5-yl, N1-CH₂COOH) | —COOH | S | |
| 10 | 6-(CH₂-)-3-hydroxy-1-hydroxy-4(1H)-pyridinone | —CH₂S—(tetrazol-5-yl, N1-CH₂CH₂OH) | —COOH | S | |

TABLE 1-continued

| | $R^{101}$ | $R^{102}$ | $R^{103}$ | $Y^{101}$ | Remarks |
|---|---|---|---|---|---|
| 11 | 2-methyl-5-hydroxy-1-hydroxy-4(1H)-pyridinone-methyl | $-CH_2S-C(=N-N=C(CH_3))-S-$ (1,3,4-thiadiazole) | $-COOH$ | S | |
| 12 | 2-methyl-5-hydroxy-1-hydroxy-4(1H)-pyridinone-methyl | $-CH_2S$-(4-pyridinio)-$N^+CH_2COOH$ | $-COO^-$ | S | |
| 13 | $-CH(COOH)$-(3,4-dihydroxyphenyl) | $-CH_3$ | $-COO^-$ | S | |
| 14 | $-CH_2$-(3,4-dihydroxyphenyl) | $-CH_2S$-(4-pyridinio)-$N^+CH_2COOH$ | $-COO^-$ | S | |
| 15 | 2-methyl-5-hydroxy-1-hydroxy-4(1H)-pyridinone-methyl | $-CH_2S$-(1,2,3-thiadiazol-5-yl) | $-COOH$ | S | |
| 16 | $-CH(COOH)$-(3,4-dihydroxyphenyl) | $-CH_2S-C(=N-N=C(CH_3))-S-$ (1,3,4-thiadiazole) | $-COOH$ | S | |
| 17 | $-CH_3$ | $-CH_2S$-(4-pyridinio)-$N^+-CH_2-C(=O)-NH-NH-C(=O)$-(3,4-dihydroxyphenyl) | $-COO^-$ | S | |
| 18 | $-CH_3$ | $-CH_2S$-(4-pyridinio)-$N^+-CH_2-C(=O)$-(3,4-dihydroxyphenyl) | $-COO^-$ | S | |

TABLE 1-continued
| | $R^{101}$ | $R^{102}$ | $R^{103}$ | $Y^{101}$ | Remarks |
|---|---|---|---|---|---|
| 19 | $-C_2H_5$ | 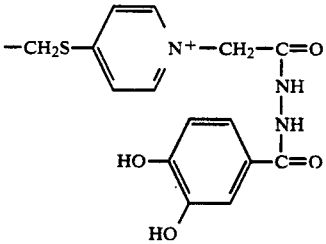 | $-COO^-$ | S | |
| 20 | $-C_2H_5$ | 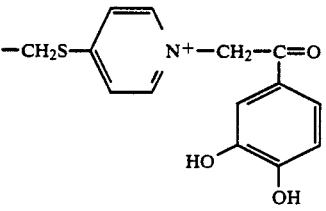 | $-COO^-$ | S | |
| 21 | $-C_3H_7$ | 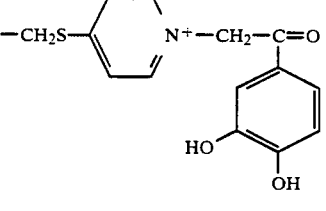 | $-COO^-$ | S | |
| 22 | $-C_3H_7$ | 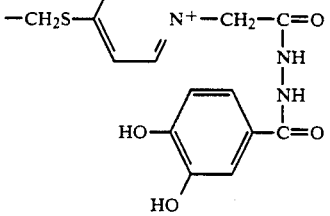 | $-COO^-$ | S | |
| 23 | 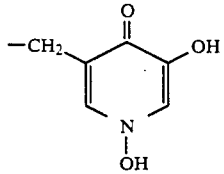 | 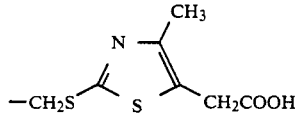 | $-COOH$ | S | |
| 24 | $-C_2H_4COOH$ | 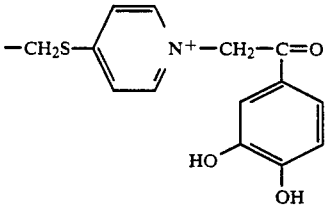 | $-COO^-$ | O | |
| 25 | 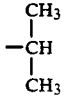 | 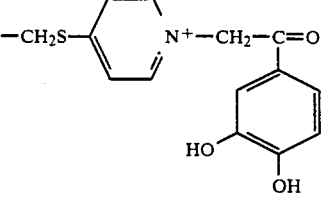 | $-COO^-$ | O | |

TABLE 1-continued

| | R¹⁰¹ | R¹⁰² | R¹⁰³ | Y¹⁰¹ | Remarks |
|---|---|---|---|---|---|
| 26 | (CH₃)₂C(COOH)– | –CH₂S–(4-pyridinium)–N⁺–CH₂–C(=O)–(3,4-dihydroxyphenyl) | –COO⁻ | O | |
| 27 | (CH₃)₂C(COOH)– | –CH₂S–(4-pyridinium)–N⁺–CH₂–C(=O)–NH–NH–C(=O)–(3,4-dihydroxyphenyl) | –COO⁻ | O | |
| 28 | –CH₂COOH | –CH₂S–(4-pyridinium)–N⁺–CH₂–C(=O)–(3,4-dihydroxyphenyl) | –COO⁻ | O | |
| 29 | –CH₂–(1-hydroxy-5-hydroxy-4-oxo-pyridin-2-yl) | –CH₂S–(5-methyl-1,3,4-thiadiazol-2-yl) | –COOH | O | |
| 30 | –CH₂–(1-hydroxy-5-hydroxy-4-oxo-pyridin-2-yl) | –CH₂S–(1,3,4-thiadiazol-2-yl) | –COOH | O | |
| 31 | –CH₂–(1-hydroxy-5-hydroxy-4-oxo-pyridin-2-yl) | –CH₃ | –COO⁻ | O | Sodium salt |
| 32 | CH₃CH₂–C(CH₃)(COOH)– | –CH₂S–(4-pyridinium)–N⁺–CH₂–C(=O)–(3,4-dihydroxyphenyl) | –COO⁻ | O | |

TABLE 1-continued

| | $R^{101}$ | $R^{102}$ | $R^{103}$ | $Y^{101}$ | Remarks |
|---|---|---|---|---|---|
| 33 | $\underset{CH_3}{\underset{|}{\overset{C_2H_5}{\overset{|}{-C-COOH}}}}$ | —CH₂S—(4-pyridinium)—N⁺—CH₂—C(=O)—NH—NH—C(=O)—(3,4-dihydroxyphenyl) | —COO⁻ | O | |
| 34 | —CH₃ | —CH₂S—(4-pyridinium)—N⁺—CH₂—C(=O)—NH—NH—C(=O)—(3,4-dihydroxyphenyl) | —COO⁻ | O | |
| 35 | —CH₃ | —CH₂S—(4-pyridinium)—N⁺—CH₂—C(=O)—(3,4-dihydroxyphenyl) | —COO⁻ | O | |
| 36 | —C₂H₅ | —CH₂S—(4-pyridinium)—N⁺—CH₂—C(=O)—NH—NH—C(=O)—(3,4-dihydroxyphenyl) | —COO⁻ | O | |
| 37 | —C₂H₅ | —CH₂S—(4-pyridinium)—N⁺—CH₂—C(=O)—(3,4-dihydroxyphenyl) | —COO⁻ | O | |
| 38 | —C₃H₇ | —CH₂S—(4-pyridinium)—N⁺—CH₂—C(=O)—NH—NH—C(=O)—(3,4-dihydroxyphenyl) | —COO⁻ | O | |

TABLE 1-continued
| | $R^{101}$ | $R^{102}$ | $R^{103}$ | $Y^{101}$ | Remarks |
|---|---|---|---|---|---|
| 39 | —C₃H₇ | 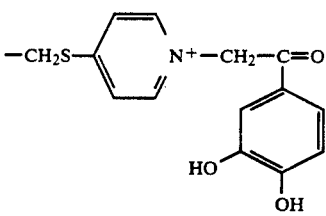 | —COO⁻ | O | |
| 40 | 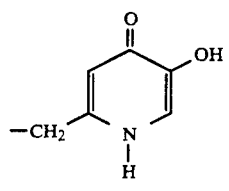 | —CH₃ | —COOH | S | |
| 41 | 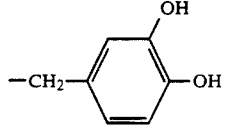 | —CH₃ | —COOH | S | |
| 42 | 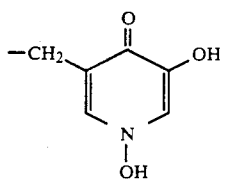 | —CH₃ | —COOH | S | |
| 43 | 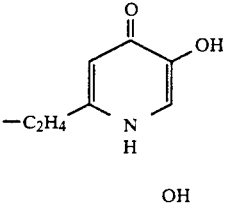 | —CH₃ | —COOH | S | |
| 44 | 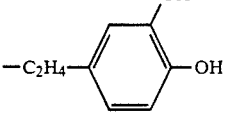 | —CH₃ | —COOH | S | |
| 45 | 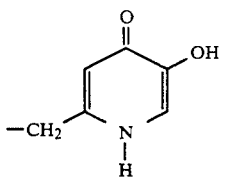 | H | —COOH | S | |
| 46 | 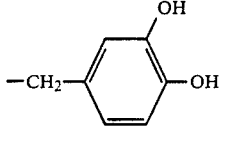 | H | —COOH | S | |
| 47 | 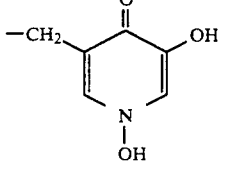 | H | —COOH | S | |

TABLE 1-continued

| | $R^{101}$ | $R^{102}$ | $R^{103}$ | $Y^{101}$ | Remarks |
|---|---|---|---|---|---|
| 48 | -C₂H₄-(3-hydroxy-4-oxo-1,4-dihydropyridin-6-yl) | H | —COOH | S | |
| 49 | -C₂H₄-(3,4-dihydroxyphenyl) | H | —COOH | S | |
| 50 | -CH₂-(5-hydroxy-4-oxo-1-methyl-1,4-dihydropyridin-2-yl) | —CH₃ | —COOH | O | |
| 51 | -CH₂-(3,4-dihydroxyphenyl) | —CH₃ | —COOH | O | |
| 52 | -CH₂-(5-hydroxy-1-hydroxy-4-oxo-1,4-dihydropyridin-3-yl) | —CH₃ | —COOH | O | |
| 53 | -C₂H₄-(5-hydroxy-4-oxo-1,4-dihydropyridin-2-yl) | —CH₃ | —COOH | O | |
| 54 | -C₂H₄-(3,4-dihydroxyphenyl) | —CH₃ | —COOH | O | |
| 55 | -CH₂-(5-hydroxy-4-oxo-1,4-dihydropyridin-2-yl) | H | —COOH | O | |
| 56 | -CH₂-(3,4-dihydroxyphenyl) | H | —COOH | O | |

TABLE 1-continued
| | $R^{101}$ | $R^{102}$ | $R^{103}$ | $Y^{101}$ | Remarks |
|---|---|---|---|---|---|
| 57 | 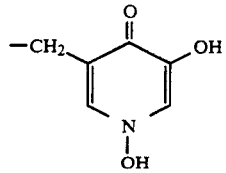 | H | —COOH | O | |
| 58 | 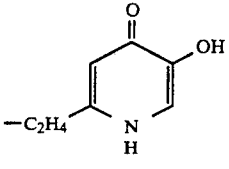 | H | —COOH | O | |
| 59 | 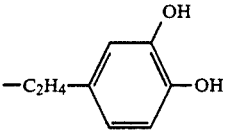 | H | —COOH | O | |
| 60 | 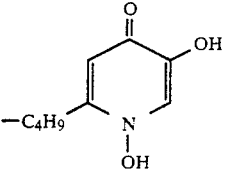 | —C$_3$H$_7$ | —COOH | O | |
TABLE 2
| | $R^{201}$ | $R^{202}$ | $R^{203}$ | Remarks |
|---|---|---|---|---|
| 1 | 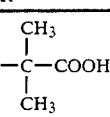 | 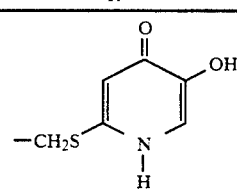 | —COO$^-$ | |
| 2 | 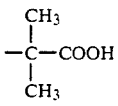 | 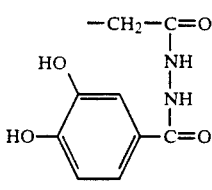 | —COO$^-$ | |
| 3 | 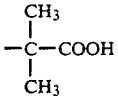 | 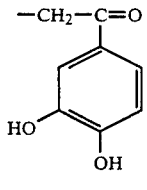 | —COO$^-$ | |
| 4 | —CH$_3$ | 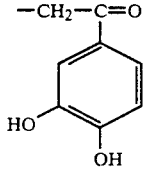 | —COO$^-$ | |

TABLE 2-continued

| | $R^{201}$ | $R^{202}$ | $R^{203}$ | Remarks |
|---|---|---|---|---|
| 5 | —CH₃ | 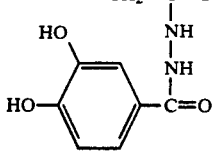 —CH₂—C(=O)—NH—NH—C(=O)—(3,4-dihydroxyphenyl) | —COO⁻ | |
| 6 | —CH₂COOH | 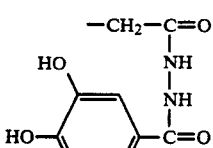 —CH₂—C(=O)—NH—NH—C(=O)—(3,4-dihydroxyphenyl) | —COO⁻ | |
| 7 | —CH₂COOH | 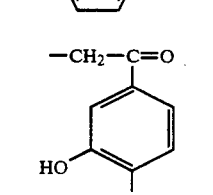 —CH₂—C(=O)—(3,4-dihydroxyphenyl) | —COO⁻ | |
| 8 | —CH₃ | 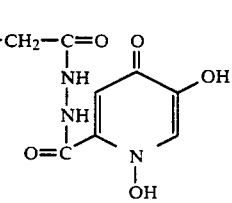 —CH₂—C(=O)—NH—NH—C(=O)—(1-hydroxy-4-oxo-5-hydroxypyridin-2-yl) | —COO⁻ | |
| 9 | —CH₃ | 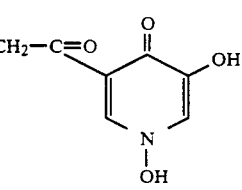 —CH₂—C(=O)—(1-hydroxy-4-oxo-5-hydroxy-1,4-dihydropyridin-3-yl) | —COO⁻ | |
| 10 | —CH₃ | 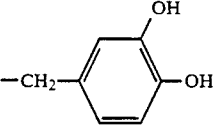 —CH₂—(3,4-dihydroxyphenyl) | —COO⁻ | |
| 11 | —C₂H₅ | 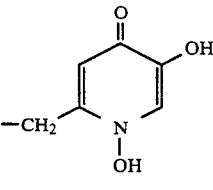 —CH₂—(1-hydroxy-4-oxo-5-hydroxy-1,4-dihydropyridin-2-yl) | —COOH | |
| 12 | —C₂H₅ | 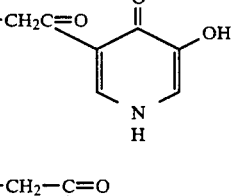 —CH₂—C(=O)—(4-oxo-5-hydroxy-1,4-dihydropyridin-3-yl) | —COOH | |
| 13 | —C₂H₅ | 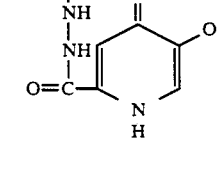 —CH₂—C(=O)—NH—NH—C(=O)—(4-oxo-5-hydroxy-1,4-dihydropyridin-2-yl) | —COOH | |

TABLE 2-continued
| | $R^{201}$ | $R^{202}$ | $R^{203}$ | Remarks |
|---|---|---|---|---|
| 14 | $-C_2H_5$ | 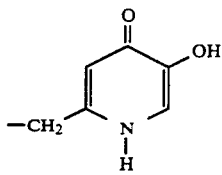 | $-COOH$ | |
| 15 | $-C_2H_5$ | 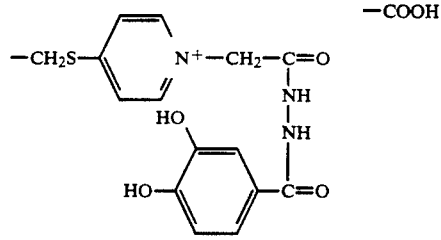 | $-COOH$ | |
| 16 | $-C_2H_5$ | 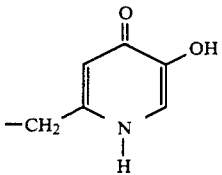 | $-COOH$ | |
| 17 | $-C_2H_5$ | 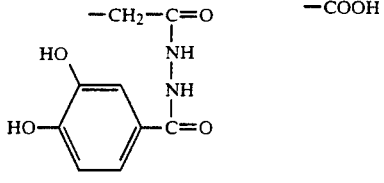 | $-COOH$ | |
| 18 | $-C_2H_5$ | 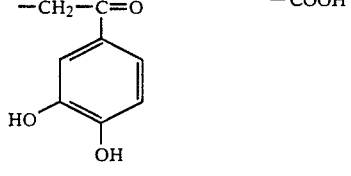 | $-COOH$ | |
| 19 | $-C_2H_5$ | 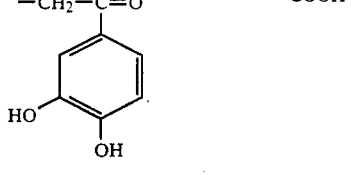 | $-COOH$ | |
| 20 | $-C_2H_5$ | 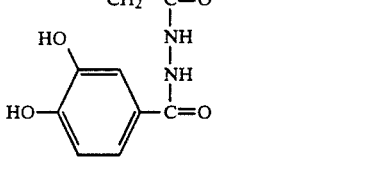 | $-COOH$ | |
| 21 | $-CH_2COOH$ | 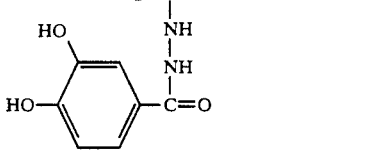 | $-COOH$ | |

TABLE 2-continued

| | $R^{201}$ | $R^{202}$ | $R^{203}$ | Remarks |
|---|---|---|---|---|
| 22 | —CH$_2$COOH | —CH$_2$—C(=O)—(3,4-dihydroxyphenyl) | —COOH | |
| 23 | —CH$_3$ | —CH$_2$—C(=O)— attached to N-hydroxy-5-hydroxy-4-oxo-pyridine-2-carbohydrazide | —COOH | |
| 24 | —CH$_3$ | —CH$_2$—C(=O)— attached to 1-hydroxy-5-hydroxy-4-oxo-1,4-dihydropyridin-3-yl | —COOH | |
| 25 | —CH$_3$ | —CH$_2$—(3,4-dihydroxyphenyl) | —COOH | |
| 26 | —C(CH$_3$)$_3$ | —CH$_2$S— attached to 5-hydroxy-4-oxo-1,4-dihydropyridin-2-yl | —COO$^-$ | |
| 27 | —C(CH$_3$)$_3$ | —CH$_2$—C(=O)—NH—NH—C(=O)—(3,4-dihydroxyphenyl) | —COO$^-$ | |
| 28 | —C(CH$_3$)$_3$ | —CH$_2$—C(=O)—(3,4-dihydroxyphenyl) | —COO$^-$ | |
| 29 | —C(CH$_3$)$_2$C$_2$H$_5$ | —CH$_2$—C(=O)—(3,4-dihydroxyphenyl) | —COO$^-$ | |

TABLE 2-continued

| | $R^{201}$ | $R^{202}$ | $R^{203}$ | Remarks |
|---|---|---|---|---|
| 30 | $\underset{\underset{CH_3}{|}}{\overset{\overset{CH_3}{|}}{-C-C_2H_5}}$ | 3,4-dihydroxybenzoyl hydrazide acetyl group ($-CH_2-C(=O)-NH-NH-C(=O)-C_6H_3(OH)_2$) | $-COO^-$ | |
| 31 | $-C_2H_5$ | $-CH_2-$(5-hydroxy-4-oxo-1,4-dihydropyridin-2-yl) | $-COO^-$ | |
| 32 | $-C_2H_5$ | 3,4-dihydroxybenzoyl hydrazide acetyl group | $-COO^-$ | |
| 33 | $-C_3H_7$ | $-CH_2-C(=O)-$(3,4-dihydroxyphenyl) | $-COO^-$ | |
| 34 | $-C_3H_7$ | $-CH_2-C(=O)-$(3,4-dihydroxyphenyl) | $-COOH$ | |
| 35 | $-C_3H_7$ | 3,4-dihydroxybenzoyl hydrazide acetyl group | $-COOH$ | |
| 36 | $\underset{\underset{CH_3}{|}}{\overset{\overset{CH_3}{|}}{-C-COOH}}$ | $-C_2H_4-$(5-hydroxy-4-oxo-1,4-dihydropyridin-2-yl) | $-COOH$ | |
| 37 | $\underset{\underset{CH_3}{|}}{\overset{\overset{CH_3}{|}}{-C-COOH}}$ | 3,4-dihydroxybenzoyl hydrazide propionyl group ($-C_2H_4-C(=O)-NH-NH-C(=O)-C_6H_3(OH)_2$) | $-COOH$ | |

TABLE 2-continued

| | $R^{201}$ | $R^{202}$ | $R^{203}$ | Remarks |
|---|---|---|---|---|
| 38 | $\underset{CH_3}{\underset{|}{\overset{CH_3}{\overset{|}{-C-COOH}}}}$ | $-C_3H_6-C(=O)-$ (3,4-dihydroxyphenyl) | $-COOH$ | |
| 39 | $-CH_3$ | $-C_3H_6-C(=O)-$ (3,4-dihydroxyphenyl) | $-COOH$ | |
| 40 | $-CH_3$ | $-C_3H_6-C(=O)-NH-NH-C(=O)-$ (3,4-dihydroxyphenyl) | $-COOH$ | |
| 41 | $-CH_2COOH$ | $-C_2H_4-C(=O)-NH-NH-C(=O)-$ (3,4-dihydroxyphenyl) | $-COO^-$ | |
| 42 | $-CH_2COOH$ | $-C_2H_4-C(=O)-$ (3,4-dihydroxyphenyl) | $-COO^-$ | |
| 43 | $-CH_3$ | $-C_2H_4-C(=O)-NH-NH-C(=O)-$ (1-hydroxy-4-oxo-5-hydroxy-pyridin-2-yl) | $-COO^-$ | |
| 44 | $-CH_3$ | $-C_2H_4-C(=O)-$ (1-hydroxy-4-oxo-5-hydroxy-pyridin-3-yl) | $-COO^-$ | |
| 45 | $-CH_3$ | $-C_2H_4-$ (2,4-dihydroxyphenyl) | $-COO^-$ | |

TABLE 3

| | R[301] | R[302] | Y[301] | Y[302] | A[301] | Remarks |
|---|---|---|---|---|---|---|
| 1 | -CH₂S-[4-methyl-5-(CH₂COOH)-thiazol-2-yl] | -COOH | -CH₂- | -S- | -CH₂- | |
| 2 | -CH₂S-[4-methyl-5-(CH₂COOH)-thiazol-2-yl] | -COOH | -S- | -CH₂- | -CH₂- | |
| 3 | -CH₂S-[1-(CH₂COOH)-tetrazol-5-yl] | -COOH | -CH₂- | -S- | -CH₂- | |
| 4 | -CH₂S-[1-(CH₂COOH)-tetrazol-5-yl] | -COOH | -S- | -CH₂- | -CH₂- | |
| 5 | -CH₂S-[4-HOOC-3-OH-isothiazol-5-yl] | -COOH | -CH₂- | -S- | -CH₂- | |
| 6 | -CH₂S-[4-HOOC-3-OH-isothiazol-5-yl] | -COOH | -S- | -CH₂- | -CH₂- | |
| 7 | -CH₂S-[1-(CH₂COOH)-pyridinium-4-yl] | -COO⁻ | -CH₂- | -S- | -CH₂- | |
| 8 | -CH₂S-[1-(CH₂COOH)-pyridinium-4-yl] | -COO⁻ | -S- | -CH₂- | -CH₂- | |
| 9 | -CH₂S-[5-methyl-1,3,4-thiadiazol-2-yl] | -COOH | -S- | -CH₂- | -CH₂- | |
| 10 | -CH₂S-[5-methyl-1,3,4-thiadiazol-2-yl] | -COOH | -CH₂- | -S- | -C₂H₄- | |
| 11 | -CH₂S-[1,3,4-thiadiazol-2-yl] | -COOH | -S- | -CH₂- | -C₂H₄- | |
| 12 | -CH₂S-[1-methyl-pyridinium-4-yl] | -COO⁻ | -S- | -CH₂- | -CH₂- | |
| 13 | -CH₂S-[1-methyl-pyridinium-4-yl] | -COO⁻ | -S- | -CH₂- | -CH₂- | |

TABLE 3-continued

| | R³⁰¹ | R³⁰² | Y³⁰¹ | Y³⁰² | A³⁰¹ | Remarks |
|---|---|---|---|---|---|---|
| 14 | -CH₂S-[thiadiazole with COOH] | -COOH | -S- | -CH₂- | -CH₂- | |
| 15 | -CH₂S-[thiadiazole with COOH] | -COO⁻ | -S- | -CH₂- | -C₂H₄- | |
| 16 | -CH₂S-[thiadiazole] | -COOH | -S- | -CH₂- | -CH₂- | |
| 17 | -CH₂S-[thiadiazole] | -COOH | -CH₂- | -S- | -C₂H₄- | |
| 18 | -CH₂S-[tetrazole-N-C₂H₅] | -COOH | -S- | -CH₂- | -CH₂- | |
| 19 | -CH₂S-[tetrazole-N-C₂H₅] | -COOH | -CH₂- | -S- | -CH₂- | |
| 20 | -CH₂S-[thiazole with C₂H₅ and CH₂COOH] | -COOH | -CH₂- | -S- | -CH₂- | |
| 21 | -CH₂S-[thiazole with C₃H₆ and OH] | -COO⁻ | -S- | -CH₂- | -CH₂- | |
| 22 | -CH₂S-[thiazole with OH and C₂H₄COOH] | -COOH | -S- | -CH₂- | -CH₂- | |
| 23 | -CH₂S-[thiazole with COOH and C₃H₆] | -COOH | -CH₂- | -S- | -CH(CH₃)₂ | |
| 24 | -CH₂S-[thiazole with CH₃ and COOH] | -COOH | -CH₂- | -S- | -C₄H₈- | |
| 25 | -CH₂S-[tetrazole-N-CH₂COOH] | -COOH | -S- | -CH₂- | -C₂H₄- | |
| 26 | -CH₂S-[tetrazole-N-CH₃] | -COOH | -S- | -CH₂- | -C₃H₆- | |

TABLE 3-continued

| | $R^{301}$ | $R^{302}$ | $Y^{301}$ | $Y^{302}$ | $A^{301}$ | Remarks |
|---|---|---|---|---|---|---|
| 27 | ![structure with CH3, OH, -CH2S-, thiazole N-S] | —COOH | —S— | —CH2— | —CH2— | |
| 28 | ![structure with HOOC, OH, -CH2S-, thiazole N-S] | —COO⁻ | —S— | —CH2— | —CH2— | |
| 29 | ![structure with OH, COOH, -CH2S-, thiophene S] | —COO⁻ | —S— | —CH2— | —C4H8— | |
| 30 | ![structure -CH2S-pyridinium N+C2H5] | —COO⁻ | —S— | —CH2— | —C5H10— | |

The cephalosporin derivatives and the starting compounds of this invention can be produced by various methods; for example the compounds can be produced according to the Reaction schemes-1a to -6f.

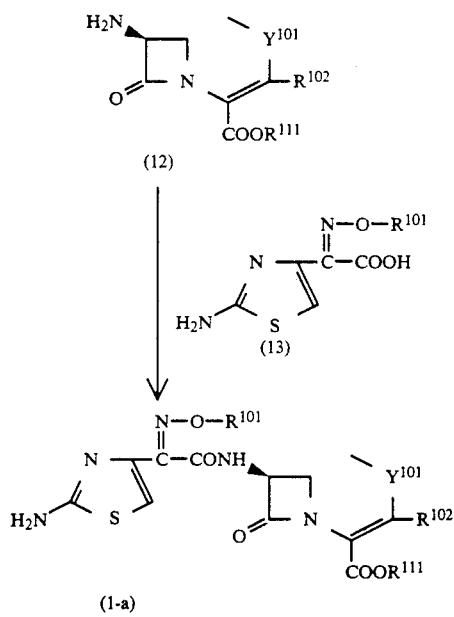

Reaction scheme-1a wherein $R^{101}$, $R^{102}$, and $Y^{101}$ are the same as defined above, and $R^{111}$ is a hydrogen atom or an ester residue.

In the Reaction scheme-1a described above, the compounds represented by the general formula (1-a) including some of the compounds of this invention represented by the general formula (1) can be produced by as usual amide-bond-forming reaction between a carboxylic acid compound represented by the general formula (13) or that of which carboxy group has been activated and an amino compound.

The ester residues represented by $R^{111}$ are exemplified by usual ester residues, i.e. alkyl groups having 1 to 6 carbon atoms, such as methyl, ethyl, propyl, isopropyl, butyl, isobutyl, t-butyl, pentyl and hexyl; (mono- or di-)phenyl-lower-alkyl groups of which alkyl moiety has 1 to 6 carbon atoms, such as benzyl, benzhydryl, α-phenetyl, β-phenetyl, α,β-diphenylethyl, 3-phenylpropyl, 4-phenylbutyl, 5-phenylpentyl and 6-phenylhexyl; alkenyl groups having 2 to 6 carbon atoms, such as vinyl, allyl, crotyl, 2-pentenyl and 2-hexenyl; cycloalkyl groups having 3 to 8 carbon atoms each, such as cyclopropyl, cyclobutyl, cyclopentyl, cyclohexyl, cycloheptyl and cyclooctyl; and cycloalkyl(lower)alkyl groups of which cycloalkyl moiety has 3 to 8 carbon atoms and of which alkyl moiety has 1 to 6 carbon atoms such as cyclohexylmethyl, 2-cyclohexylethyl, 3-cyclohexylpropyl, 4-cyclohexylbutyl, 5-cyclohexylpentyl, 6-cyclohexylhexyl, cyclopropylmethyl, 2-cyclobutylethyl, cyclopentylmethyl, 2-cycloheptylethyl and cyclooctylmethyl.

The phenyl moieties of the (mono- or di-)phenyl-lower-alkyl groups as the ester residues described above may have 1 to 3 substituents selected the group consisting of halogen atoms such as chlorine atom, bromine atoms, fluorine atom, and iodine atom; lower alkyl groups having 1 to 6 carbon each such as methyl, ethyl, propyl, isopropyl, butyl, isobutyl, t-butyl, pentyl and hexyl; lower alkoxy groups having 1 to 6 carbon atoms such as methoxy, ethoxy, propoxy, isopropoxy, butoxy, t-butoxy, pentyloxy and hexyloxy; nitro group; carboxy group; cyano group; and hydroxyl group, or may have lower alkylenedioxy groups having 1 to 4 carbon atoms such as methylenedioxy, ethylenedioxy, trimethylenedioxy and tetramethylenedioxy.

The lower alkyl groups as the ester residues described above may be substituted, for example, by 1 to 3 halogen atoms, hydroxyl group, mercapto group, lower alkoxy groups described above, lower alkanoyloxy group described above, carboxy group, cyano group, nitro group, amino group, lower alkyl group described above, (mono- or di-)lower-alkylamino group such as methylamino, dimethylamino, ethylamino, diethylamino, propylamino and butylamino, lower alkanoylamino group described above, or lower alkylthio groups such as methylthio, ethylthio, propylthio, or butylthio.

Examples of the lower alkanoyloxy group include alkanoyloxy groups which has 1 to 6 carbon atoms, such as formyloxy, acetoxy, propionyloxy, butyryloxy, isobutyryloxy, pentanoyloxy, hexanoyloxy and the like.

Examples of the lower alkanoylamino group include alkanoylamino groups having 1 to 6 carbon atoms, such as formylamino, acetylamino, propionylamino, butyrylamino, isobutyrylamino, pentanoylamino, hexanoylamino and the like.

To the amide-bond-forming reaction, the conditions for the known amide-bond-forming reaction are applicable. For example, a) The method using a condensing agent: wherein the carboxylic acid compound(13) is reacted with the amine compound(12) in the presence of a condensing agent;

b) The mixed acid anhydride method: wherein the mixed acid anhydride is obtained by the reaction between a carboxylic acid compound(13) and an alkylhalocarboxylic acid, and the mixed acid anhydride is reacted with an amine compound(12);

c) The active ester method: wherein a carboxylic acid compound (13) is converted into an active ester such as p-nitrophenyl ester, N-hydroxysuccinimide ester, or 1-hydroxybenzotriazole ester, which is then allowed to react with an amine (12);

d) The method where a carboxylic acid compound(13) is converted into a carboxylic acid anhydride by a dehydrating agent such as acetic anhydride, followed by the reaction with an amine compound(12);

e) The method where a lower alcohol ester of a carboxylic acid compound(13) and an amine compound(12) are allowed to react at high temperature under high pressure;

f) The method where the carboxylic acid (13) is converted into an acid halide, i.e. carboxylic acid halide, which is then allowed to react with an amine compound(12).

An example of the amide-bond-forming reaction is described in more detail below:

The compound of the invention represented by the general formula (1-a) are obtained by reacting of an amine compound represented by the general formula (12) with a carboxylic acid compound represented by the general formula (13) in the presence of a condensing agent, without solvent or in an inert solvent.

The condensing agents used in the said reaction include, for example, thionyl chloride, phosphorus oxychloride, phosphorus pentachloride, a Vilsmeier reagent such as (chloromethylene)dimethylammonium chloride produced by the reaction of dimethylformamide with thionyl chloride, phosphorus oxychloride or phosgene, dicyclohexylcarbodiimide (DCC) and 2,2'-pyridinyl disulfido-triphenylphosphine.

Any solvent may be used unless it exerts adverse effect on the reaction. Such solvents are exemplified by ethers such as diethyl ether, tetrahydrofuran, dioxane and the like; halogenated hydrocarbons such as dichloromethane, dichloroethane, chloroform, carbon tetrachloride and the like; aromatic hydrocarbons such as benzene, toluene, xylene and the like; amines such as pyridine, piperidine, triethylamine and the like; aliphatic hydrocarbons such as hexane, heptane and the like, alcohols such as methanol, ethanol, propanol and the like; aprotoic polar solvents such as dimethylformamide (DMF), hexamethylphosphoric triamide (HMPA), dimethylsulfoxide (DMSO) and the like; and carbon disulfide.

The reaction described above is preferably carried out in the presence of a basic compound. Such basic compounds include trialkyl amines such as triethylamine, tributylamine and the like; organic bases such as pyridine, picoline, 1,5-diazabicyclo[4.3.0]nonene-5, 1,4-diazabicyclo[2.2.2]octane, and 1,8-diazabicyclo[5.4.0]undecene-7 and the like; monotrimethylsilylacetamide, and inorganic bases exemplified by alkali metal hydroxides such as sodium hydroxide, potassium hydroxide and the like; alkali metal carbonates such as sodium carbonate, potassium carbonate and the like; and alkali metal hydrogencarbonate such as sodium hydrogencarbonate and potassium hydrogencarbonate.

In the reaction described above, the carboxylic acid compound of formula (13) and the amine compound of the formula (12) are present in a molar ratio of 1:1 to 10:1, preferably 1:1 to 3:1. The basic compound and the amine compound of the formula (12) are present in a molar ratio of 1:1 to 40:1 and preferably 5:1 to 20:1.

The reaction described above is conducted at $-20°$ C. to $100°$ C., preferably at $-20°$ to $50°$ C. for 30 minutes to 24 hours, preferably for about 30 minutes to 10 hours.

Thus the compounds represented by the general formula (1-a) are obtained.

Referring to the above-mentioned reaction between an amine compound represented by the general formula (12) and a carobxylic acid compound represented by the general formula (13), there may be produced a compound where the carboxy group in the desired compound represented by the general formula (1-a) has been condensed with the carboxy group of the amine represented by the general formula (12) when the group $R^{111}$ is a carboxy group. In such a case, the compounds represented by the general formula (1-a) including some of the compounds of this invention can be obtained by hydrolysis of the condensed product in the presence of an acid catalyst such as an inorganic or organic acid exemplified by hydrochloric acid, hydrobromic acid, trifluoroacetic acid and the like.

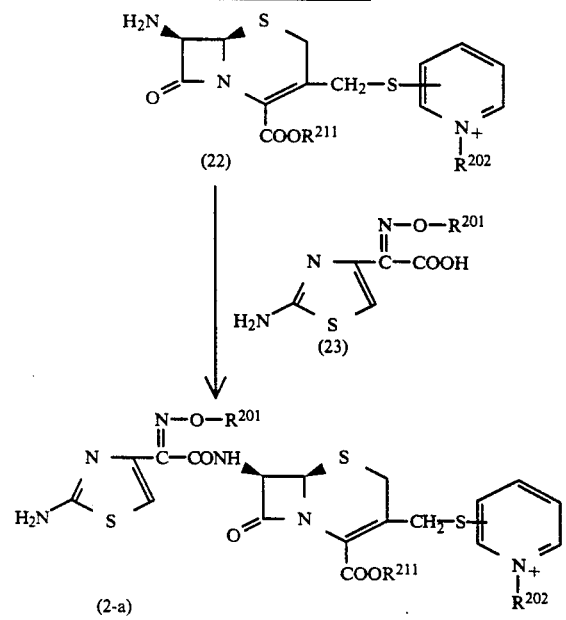

wherein $R^{201}$, and $R^{202}$ are the same as defined above. $R^{211}$ is a hydrogen atom or an ester residue.

In the Reaction scheme-1b, the compound represented by the general formula (2-a) including some of the compound of this invention represented by the general formula (2) can be produced by the usual amide-bound-forming reaction similar to that in the Reaction scheme-1a between a carboxylic acid compound represented by the general formula (23) or a compound of which the carboxy group has been activated, with an amino compound represented by the general formula (22).

The ester residue of $R^{211}$ is the same as that of $R^{111}$ mentioned in Reaction Scheme-1a.

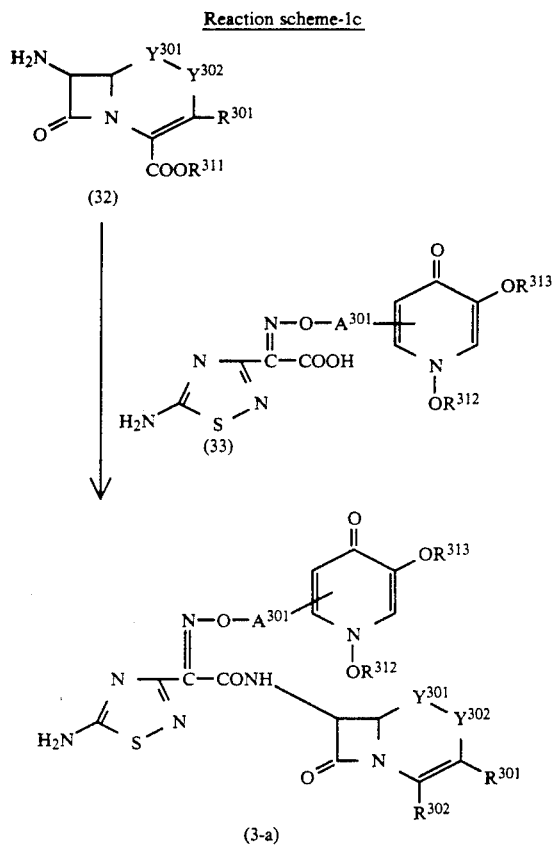

wherein $R^{301}$, $Y^{301}$, $Y^{302}$, and $A^{301}$ are the same as defined above, $R^{311}$ is a hydrogen atom or an ester residue. $R^{312}$ and $R^{313}$ are independently the same group as the ester residue in $R^{3111}$.

In the Reaction scheme-1c described above, the compounds represented by the general formula (3-a) including some of the compounds of this invention represented by the general formula (3) can be produced by the usual amide-bond-forming reaction similar to that in the Reaction scheme-1a between a carboxylic acid compound represented by the general formula (33) or a compound of which carboxy group has been activated, and an amino compound represented by the general formula (32).

The ester residue of $R^{311}$ is the same as that of $R^{111}$ mentioned in Reaction Scheme-1a.

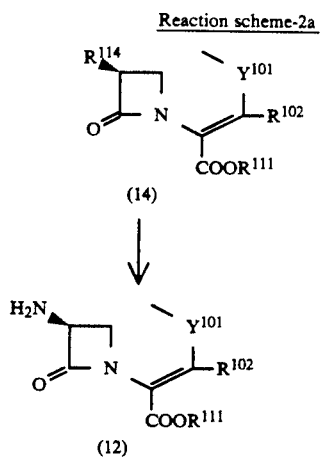

wherein $R^{102}$, $R^{111}$, and $Y^{101}$ are the same as defined above, $R^{114}$ is an azido, a phenylacetamido, or a phthalimido group.

Referring to the Reaction scheme-2a, the compounds represented by the general formula (12) including some novel compounds can produced by reduction hydrolysis or hydrazinolysis of a compound represented by the general formula (14) according to the type of the substituent $R^{114}$.

In the Reaction scheme described above, when the group $R^{114}$ is azido, the compounds represented by the general formula (12) can be obtained by reacting a compound represented by the general formula (8) with a reducing agent without solvent or in the presence of an appropriate inert solvent.

The solvents used in this reaction include halogenated hydrocarbons such as dichloromethane, dichloroethane, chloroform, carbon tetrachloride and the like, aromatic hydrocarbons such as benzene, toluene, xylene and the like; ethers such as diethyl ether, tetrahydrofuran, dioxane and the like; and amines such as triethylamine, pyridine and the like.

Example of the reducing agent is hydrogen sulfide and the like. When hydrogen sulfide is used as the reducing agent, it is preferable that an amide such as triethylamine or pyridine is added.

In this reaction, the reducing agent and the compound represented by the general formula (14) are present in a molar ratio of 1:1 to 100:1, preferably 3:1 to 50:1. The reaction is conducted usually at $-30°$ C. to $50°$ C., preferably at $-10°$ C. to $10°$ C., and completed generally in 30 minutes to 10 hours.

When the group $R^{114}$ is phenylacetamido, the amine compound represented by the general formula (12) can be obtained by hydrolyzing the compound represented by the general formula (14).

The reaction can be conducted essentially in the same way as the Reaction scheme-5a; the procedure and the reaction conditions (for example, the catalyst, solvent, reaction temperature, reaction time and the like) are referred to the description for the Reaction scheme-5a.

When the group $R^{114}$ is phthalimido, the amine compound represented by the general formula (12) can be obtained by hydrazinolysis which is reaction with hydrazine or hydrazine derivatives, either in the presence of a inert solvent or in the absence of solvent.

Examples of the inert solvent usable for this reaction include halogenated hydrocarbons such as dichloromethane, dichloroethane, chloroform, carbon tetrachloride and the like; and alcohols such as methanol, ethanol and the like. Examples of the hydrazine derivative include lower alkyl-substituted hydrazines such as methylhydrazine, ethylhydrazine and the like; and aryl-substituted hydrazines such as phenylhydrazine and the like.

In the reaction, the hydrazine or hydrazine derivatives and the compound represented by the general formula (14) are present in a molar ratio of at least 1:1, preferably 1:1 to 2:1, and the reaction is conducted usually at 0° to 100° C., preferably at 0° to 80° C., and completes in about 1 to 40 hours.

When the group $R^{111}$ is an ester residue in the compound represented by the general formula (12) obtained by the above-mentioned reaction, the compound having hydrogen atom as $R^{111}$ can be obtained by deesterification of the production in the same way as the Reaction scheme-4a.

Reaction scheme-2b

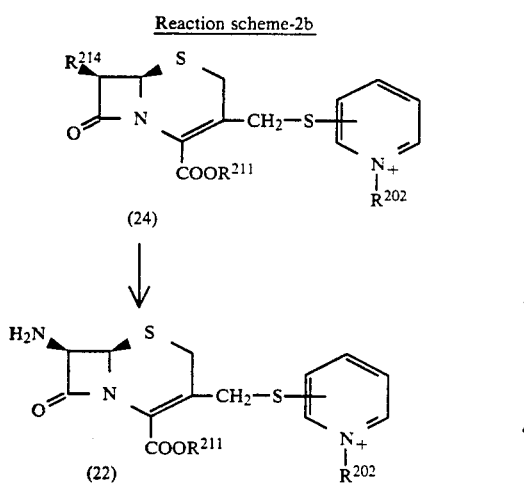

wherein $R^{202}$, $R^{211}$ are the same as defined above. $R^{214}$ is an azido, phenylacetamide or phtalimido group.

According to the above-mentioned Reaction scheme-2b, the compounds represented by the general formula (22) including some novel compounds are produced by reduction, hydrolysis or hydrazinolysis or a compound represented by the general formula (24) according to the type of the substituent $R^{214}$.

The above-mentioned reduction, hydrolysis, and hydrazinolysis can be conducted in the same way to the Reaction scheme-2a described before.

Reaction scheme-2c

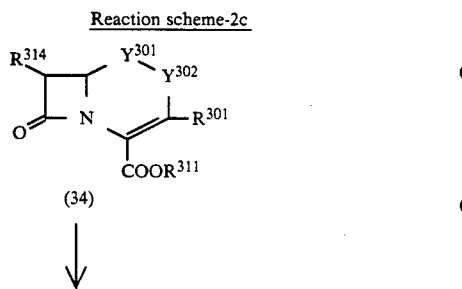

-continued
Reaction scheme-2c

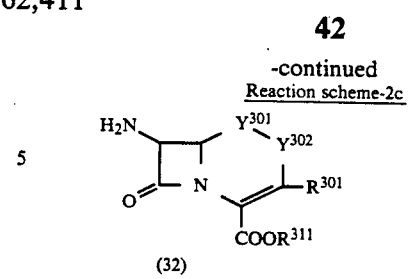

wherein $R^{301}$, $R^{311}$, $Y^{301}$, and $Y^{302}$ are the same as defined above, $R^{314}$ is an azido, phenylacetamide or phtalimido group.

According to the above-mentioned Reaction scheme-2c, the compounds represented by the general formula (32) including some novel compounds are produced by reduction, hydrolysis, or hydrazinolysis of a compound represented by the general formula (34) according to the type of the substituent $R^{14}$ in the same way to the Reaction scheme-2a described before.

Reaction scheme-3

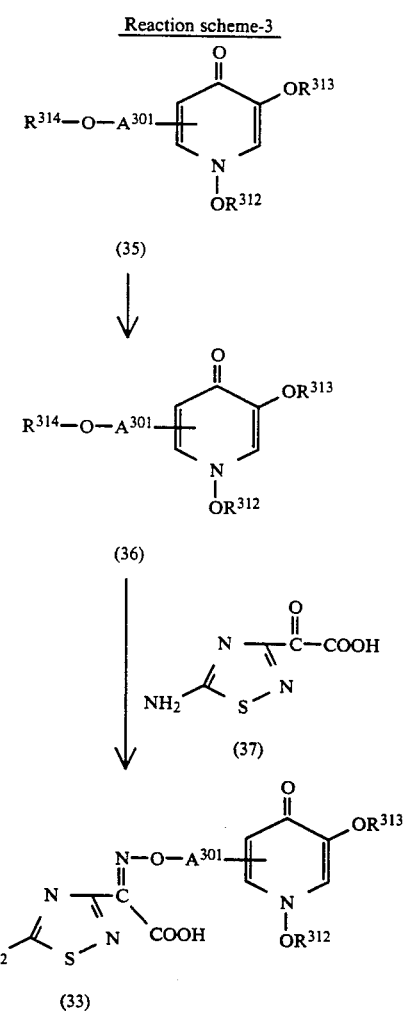

wherein $R^{312}$, $R^{313}$, $R^{314}$, and $A^{301}$ are the same as defined above.

According to the above-mentioned Reaction scheme-3, a primary amine represented by the general formula (36) is produced by reduction, hydrolysis or hydrazinolysis of a compound represented by the general formula (35) according to the type of the substituent $R^{314}$, followed by the reaction of the said primary amine compound with a carbonyl compound represented by the general formula (37), to obtain the compound represented by the general formula (33).

The reduction to obtain the compound represented by the general formula (33) can be conducted either in the absence of solvent or in the presence of solvent. The inert solvents used for this reaction are not specified, being exemplified by the inert solvents shown in the Reaction scheme-1a.

In this reaction, the compound represented by the general formula (37) and the compound represented by the general formula (36) are present in a molar ratio of at least 0.5:1, preferably 0.8:1 to 1.2:1. The reaction is conducted at 0° to 50° C. preferably 15° to 25° C.

Reaction scheme-4a

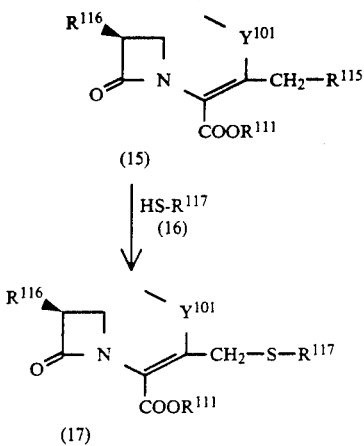

(15)

↓ HS-R$^{117}$ (16)

(17)

wherein R$^{111}$ and Y$^{101}$ are the same as defined above; R$^{115}$ is a halogen atom, lower alkanesulfonyloxy group which may be substituted with halogen atom, lower alkyl group which may be substituted with halogen atom, or arylsulfonyloxy group which may be substituted with halogen atom or nitro group; R$^{116}$ is an azido, amino, phthalimido, phenylacetamido, or a group:

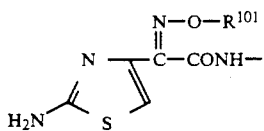

(wherein R$^{101}$ is the same as defined above); R$^{117}$ is the heterocyclic moiety which may have substitutent in R$^{102}$ described above.

There are various methods for introduction of a thiomethyl group having a hetero ring at the 3-position of the isocephem skeleton of the compounds of this invention, and an example of such methods is shown below.

The compound represented by the general formula (17) having heterocyclic thiomethyl group and including some of the compound of this invention can be obtained by reaction the compound represented by the general formula (15A) with the thiol compound represented by the general formula (16) in the presence of a basic compound.

In the compounds represented by the general formula (15), the halogen atoms represented by R$^{115}$ include chlorine atom, bromine atom, iodine atom and fluorine atom; the lower alkanesulfonyloxy groups which may be substituted with halogen atoms include methansulfonyloxy, ethansulfonyloxy, propansulfonyloxy, trifluoromethansulfonyloxy and the like; the arysulfonyloxy groups which may be substituted with lower alkyl groups, halogen atoms or nitro group include benzenesulfonyloxy, toluenesulfonyloxy, p-chlorobenzenesulfonyloxy, and p-nitrogenzenesulfonyloxy and the like.

The basic compounds used in the above-mentioned reaction include organic basic compounds such as tertiary amine e.g. triethylamine, pyridine and the like; and inorganic basic compounds such as sodium carbonate, potassium carbonate and the like.

The compound represented by the general formula (16) and the compound represented by the general formula (15) are present in a molar ratio of 1:1 to 2:1. The using molar ratio of basic compound and the compound represented by the general formula (16) is 1:1 to 2:1. The reaction temperature is −10° C. to 100° C., preferably 0° to 50° C.

In this reaction, a compound having a heterocyclic thiomethyl group represented by the general formula (17) is obtained.

Reaction scheme-4b

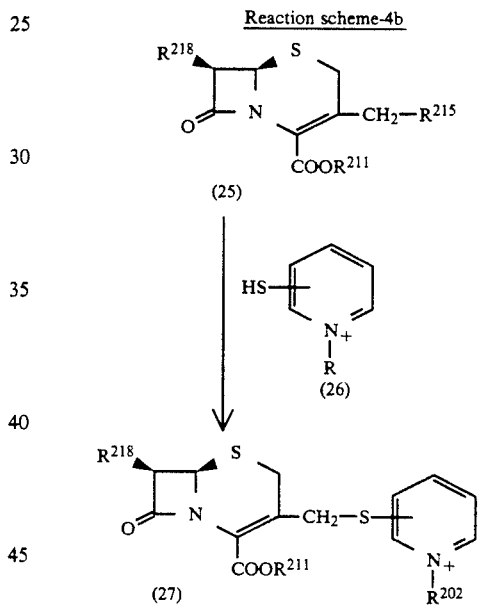

wherein R$^{202}$ and R$^{211}$ are the same as defined above; R$^{215}$ is the same group as R$^{115}$ in Reaction Scheme-4a, and R$^{218}$ is an azido, amino, phthalimido, phenylacetamido or a group:

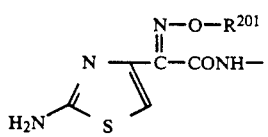

(wherein R$^{201}$ is the same as defined above).

There are various methods for introduction of a thiomethyl group having a heteroring at the 3-position of the isocephem skeleton of the compounds of this invention represented by the general formula (2), and this Reaction scheme-4b is an example of such methods.

This Reaction is conducted in the same way as the Reaction scheme-4a described above, to obtain the compound represented by the general formula (37).

Reaction scheme-4c

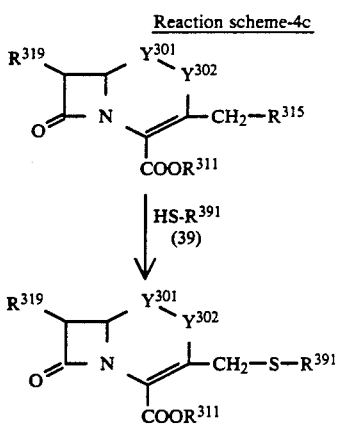

wherein $R^{311}$, $Y^{301}$, and $Y^{302}$ are the same as defined above; $R^{315}$ is the same group as $R^{115}$ in Reaction Scheme-4a; $R^{319}$ is an azido, amino, phthalimido, phenylacetamido, or the group:

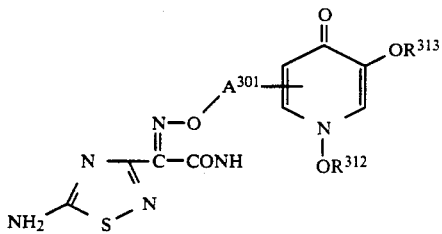

(wherein $R^{312}$, $R^{313}$, and $A^{301}$ are the same as defined above); and $R^{391}$ is the heterocyclic moiety which may have a substituent in the above-mentioned $R^{302}$.

There are various methods for introduction of a thiomethyl group as a substituent into the cephalosporin skeleton of the compounds of this invention, and the Reaction scheme-4c is an example of such methods.

The Reaction can be conducted in the same way to the Reaction scheme-4a or 4b described above.

Reaction scheme-5a

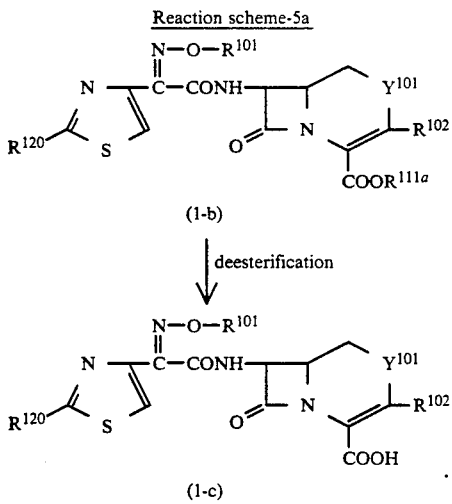

wherein $R^{101}$ and $R^{102}$ are the same as defined above, $R^{111a}$ is the ester residue in the above-mentioned $R^{111}$, and $R^{120}$ is an amino group which may have a protective group.

The carboxylic acid derivative represented by the general formula (1-c) can be produced by deesterification of the ester compound at the 4-position of the isocephem ring represented by the general formula (1-b).

The amino-protective groups in $R^{120}$ include usual protective groups exemplified by lower alkanoyl groups having 1 to 6 carbon atoms such as formyl, acetyl, propionyl, butyryl, isobutyryl, pentanoyl and hexanoyl and the like; lower alkanoyl groups having 2 to 6 carbon atoms each substituted with 1 to 3 halogen atoms, such as monochloroacetyl, monofluoroacetyl, monobromoacetyl, monoiodoacetyl, dichloroacetyl, trichloroacetyl, trifluoroacetyl, 3-chloropropionyl, 2,3-dichloropropionyl, 3,3,3-trichloropropionyl, 4-chlorobutyryl and the like, 5-chloropentanoyl, 6-chlorohexanoyl, 3-fluoropropionyl, and 4-fluorobutyryl; phenyl(lower)alkyl groups that have 1 to 3phenyl groups and of which alkyl moiety has 1 to 6 carbon atoms, such as benzyl, α-phenetyl, β-phenetyl, 3-phenylpropyl, benzhydryl, trityl and the like; phenyl(lower)alkoxycarbonyl groups of which alkoxy moiety has 1 to 6 carbon atoms, such as phenylmethoxycarbonyl, 1-phenylethoxycarbonyl, 2-phenylethoxycarbonyl, 3-phenylpropoxycarbonyl, 4-phenylbutoxycarbonyl, 4-phenylbutoxycarbonyl, 5-phenylpentyloxycarbonyl, 6-phenylhexyloxycarbonyl and the like; and lower alkoxycarbonyl groups of which alkoxy moiety has 1 to 6 carbon atoms, such as methoxycarbonyl, ethoxycarbonyl, propoxycarbonyl, isopropoxycarbonyl, butoxycarbonyl, t-butoxycarbonyl, pentyloxycarbonyl hexyloxycarbonyl and the like.

The above-mentioned deesterification is conducted in absence of solvent or in presence an appropriate inert solvent and in the presence of a catalyst for hydrolysis. The inert solvents used include those shown for the Reaction scheme-1a.

The acidic compound used includes lewis acids such as anhydrous aluminum chloride, stannic chloride, titanium tetrachloride, boron trichloride, boron trifluoride-ethyl ether complex zinc chloride and the like; inorganic acids such as hydrochloric acid, nitric acid, sulfuric acid and the like; organic acids such as trichloroacetic acid, trifluoroacetic acid, methanesulfonic acid, acetic acid and the like; and acid-form ion exchange resin. The basic compound includes organic bases exemplified by trialkylamines, e.g. triethylamine, tributylamine and the like; pyridine, picoline, 1,5-diazabicyclo[4.3.0]nonene-5,1,4-diazabicyclo[2.2.2]octane, 1,8-diazabicyclo[5.4.0] undecene-7 and the like; and inorganic bases exemplified by alkali metal hydroxides such as sodium hydroxide, potassium hydroxide, alkali metal carbonates such as sodium carbonate and potassium carbonate, and alkali metal hydrogencarbonates such as sodium hydrogencarbonate, potassium hydrogencarbonate and so on.

The above-mentioned deesterification can be conducted also by catalytic reduction when $R^{111a}$ is an ester residue such as benzyl group which is readily removed by catalytic reduction method. The catalyst used for the catalytic reduction method includes platinum catalyst (e.g. platinum oxide, platinum black, platinum wire, platinum plate, platinum sponge, colloidal platinum and the like), a palladium catalysts (e.g. palladium black, palladium chloride, palladium oxide, palladium-carbon, palladium-barium sulfate, palladium-barium carbonate, spongy palladium sponge and the like), a nickel catalyst (e.g. reduced nickel, nickel oxide, Raney nickel and the like), a cobalt catalyst (e.g. reduced cobalt, Raney cobalt and the like), an iron catalyst (e.g. reduced iron, Raney iron and the like), and a copper catalyst (e.g. reduced copper, Raney copper and the like).

When the acid or base compound is used in the above-mentioned reaction, the acid or basic compound and the compound of formula (1-b) are present in a molar ratio of 1:1 to 100:1 and preferably 1:1 to 20:1. The said reaction is conducted at $-20°$ C. to $80°$ C. desirably at $-10°$ C. to $50°$ C. for 30 minutes to 48 hours, desirably for about 1 to 24 hours.

When a catalytic reduction is employed, the catalyst and the compound of formula (1-b) are present in a molar ratio of 0.1:1 to 10:1 and preferably 0.1:1 to 1:1. The said reaction is conducted at $0°$ C. to $200°$ C. preferably at $0°$ C. to $100°$ C. and in completion in about for 30 minutes to 48 hours, preferably for about 30 minutes to 6 hours.

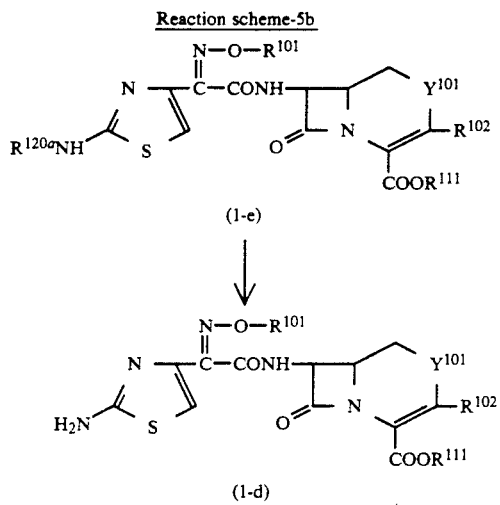

(1-e)

(1-d)

wherein $R^{101}$, $R^{102}$, $R^{111}$, and $Y^{101}$ are the same as defined above; $R^{120a}$ is the protective group of the protected amino group represented by the above-mentioned $R^{120}$.

The compound of this invention represented by the general formula (1-d) having an amino group at the 2-position of the thiazolyl group can be obtained by the reaction of the compound of this invention represented by the general formula (1-e) wherein the 2-position of the thiazolyl group is a substituted amino group under essentially the same conditions as those for the deesterification of the above-mentioned Reaction scheme-5a; for example, by the reaction with an acidic compound or basic compound or by catalytic reduction, either in the absece of solvent or in presence solvent.

The solvents used for the said reaction are not specified, including those shown for the Reaction scheme-1a.

The acidic compounds described above include those shown in the above-mentioned Reaction scheme-5a, and desirable acidic compounds include inorganic acids such as hydrochloric acid, hydrobromic acid, sulfuric acid, nitric acid and the like; organic acid such as trifluoroacetic acid, acetic acid, formic acid and the like; and acid-form ion exchange resin. Among these acidic compounds, the liquid one is used as solvents.

The basic compounds include trialkylamines such as triethylamine, tributylamine and the like; organic base such as pyridine, picoline, 1,5-diazabicyclo[4.3.0]nonene-4, 1,4-diazabicyclo[2.2.2]octane, 1,8-diazabicyclo[5.4.0]undecene-7 and the like; inorganic bases exemplified by an alkali metal hydroxide such as sodium hydroxide and potassium hydroxide and the like; an alkali metal carbonate such as sodium carbonate, potassium carbonate and the like; alkali metal hydrogencarbonate such as sodium hydrogencarbonate and potassium hydrogencarbonate, and an urea derivative such as thiourea, urea and the like.

When water is to be added to the reaction system, it is preferably that water was added in the ratio of 0 to 80% by volume to the acidic compound or the basic compound, and after completing the reaction, added in the ratio of 10 to 20 times as much as the volume of the acidic compound or the basic compound.

The acidic compound or the basic compound and the compound represented by the general formula (1-e) are in a molar ratio of 1:1 to 100:1, preferably 2:1 to 10:1. The reaction temperature is $-20°$ C. to $80°$ C., preferably $-10°$ C. to $50°$ C. The reaction completes in about 1 to 24 hours.

When the reaction of the Reaction scheme-5b is conducted through a catalytic reduction, the conditions for the catalytic reduction e.g. catalyst for the catalytic reduction, amount of the catalyst, solvent, reaction temperature, reaction time, and the like, may be the same as those for the catalytic reduction in the above-mentioned Reaction scheme-5a.

Thus the amine compounds represented by the general formula (1-d) including some of the compounds of this invention are obtained.

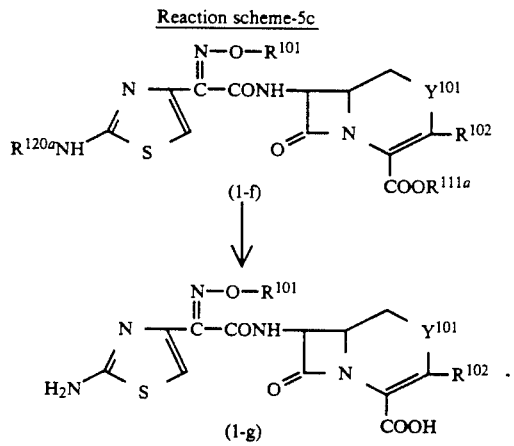

(1-f)

(1-g)

wherein $R^{101}$, $R^{102}$, $R^{120a}$, and $Y^{101}$ are the same as defined above, and $R^{111a}$ represents an ester residue in $R^{111}$.

According to this Reaction scheme-5c, deesterification at the 4-position of a compound represented by the general formula (1-f) and elimination of the protective group of the amino group represented by $R^{120a}$ are simultaneously, to give a compound represented by the general formula (1-g), and the reaction can be conducted under essentially the same conditions as those for the above-mentioned Reaction scheme-5a or -5b, though it is preferable to use an acid as a catalyst for hydrolysis, and more desirable to use an acid such as anhydrous aluminum chloride, zinc chloride, iron chloride, tin chloride, or boron trifluoride, or an organic acid such as trifluoroacetic acid.

Reaction scheme-5d

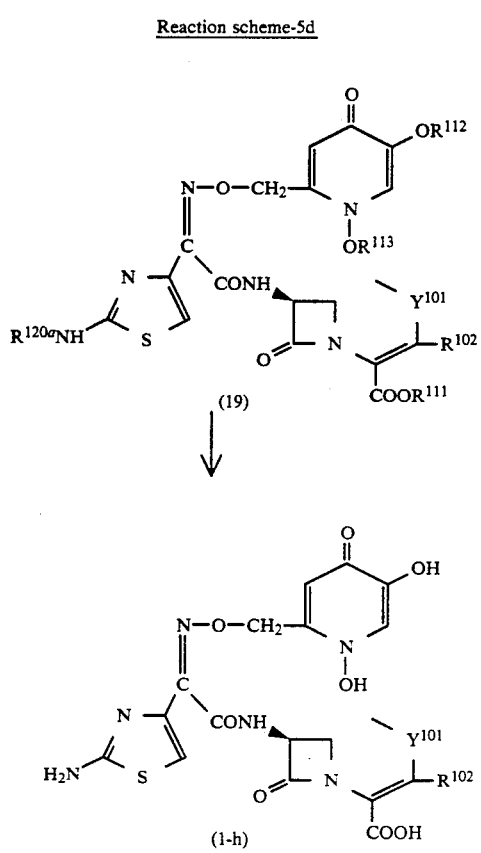

wherein $R^{102}$, $R^{111}$, $R^{120a}$, and $Y^{101}$ are the same as defined above, $R^{112}$ and $R^{123}$ are the ester residue the same or different from each other, the same groups as the ester residue represented by $R^{111a}$.

Under the same conditions as for the above-mentioned Reaction scheme-5c, the compound represented by the general formula (1-h) can be obtained by $^{113}$ and $R^{112}$ of the substituent having pyridonyl group in the compound represented by the general formula (19) substituted to hydrogen atoms. At the same time deesterification and/or removal of the protective group of the amino group may be conducted.

Reaction scheme-5e

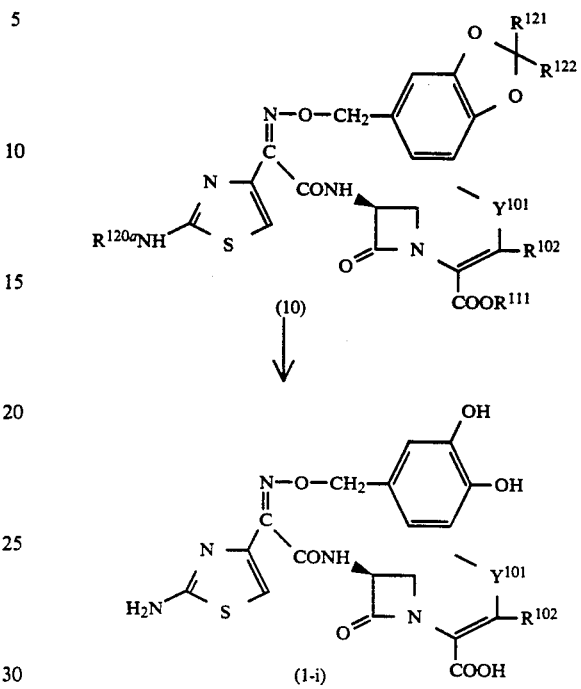

wherein $R^{102}$, $R^{111}$, $R^{120a}$, and $Y^{101}$ are the same as defined above, $R^{121}$ and $R^{122}$ are the same or different from each other, lower alkyl groups, lower alkoxy groups, lower cycloalkyl groups, cycloalkyl-lower-alkyl groups, lower alkenyl group, or (mono- or di-)phenyl-lower-alkyl group.

Under the same conditions as those for the above-mentioned Reaction scheme-5c, a ring-opening reaction is conducted to remove the group:

from the benzodioxonyl group substituted by $R^{121}$ and $R^{122}$ in a compound represented by the general formula (10), to obtain the compound of this invention having a dihydroxyphenyl group represented by the general formula (1-i). As in the above-mentioned Reaction scheme-5d, deesterification and/or removal of the amino group may be conducted at the same time.

The lower alkoxy groups of $R^{121}$ and $R^{122}$ include alkoxy groups having 1 to 6 carbon atoms such as methoxy, ethoxy, propoxy, isopropoxy, butoxy, t-butoxy, pentyloxy, hexyloxy and the like.

Reaction scheme-5f

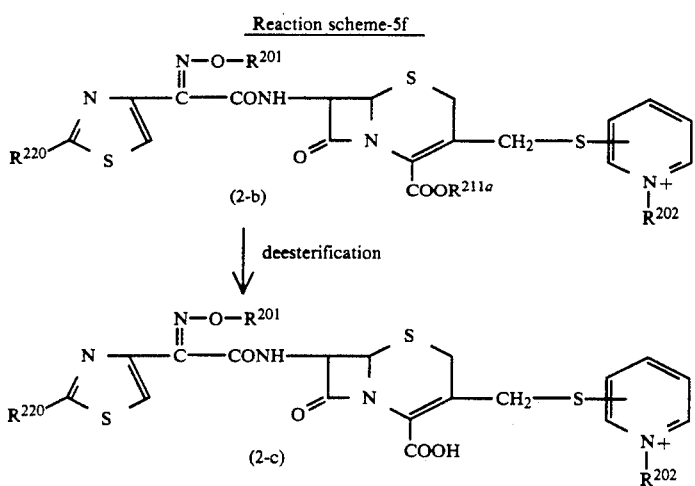

wherein $R^{201}$ and $R^{202}$ are the same as defined above, $R^{220}$ is an amino group which may have a protective group, and $R^{211a}$ is a ester residue in $R^{211}$ mentioned above.

The carboxylic acid derivative represented by the general formula (2-c) can be produced by deesterification of the ester compound at the 4-position of the isocephem ring represented by the general formula (2-b).

The deesterification can be conducted under the same conditions of the above-mentioned Reaction scheme-5a.

The amino-protective groups are the same as those of $R^{120}$ mentioned in Reaction Scheme-5a.

wherein $R^{201}$, $R^{202}$ and $R^{211}$ are the same as defined above, and $R^{220a}$ is the protective group of amino group.

The compounds of this invention represented by the general formula (2-d) wherein the 2-position of the thiazolyl group is an amino group can be produced by the reaction of a compound represented by the general formula (28) wherein the 2-position of the thiazolyl group is a substituted amino group under essentially in the same conditions as the deesterification in the above-mentioned Reaction scheme-5a.

Reaction scheme-5g

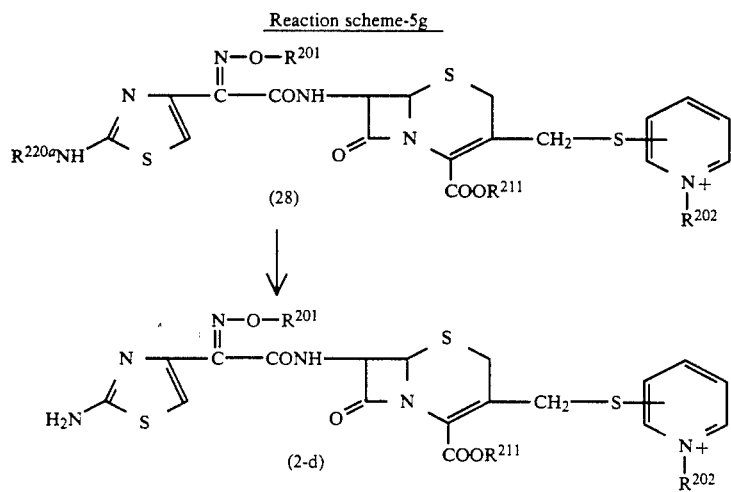

Reaction scheme-5h

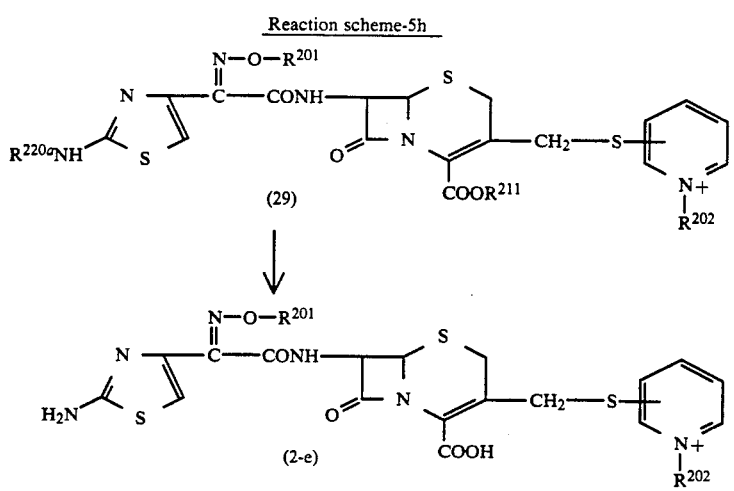

wherein $R^{201}$, $R^{202}$, $R^{211}$ and $R^{220a}$ are the same as defined above.

In this reaction, deesterification at the 4-position and the removal of the amino-protective group represented by $R^{220a}$ of a compound represented by the general formula (29) are conducted at the same time, to give the compound represented by the general formula (2-e), and the reaction can be conducted under essentially the same conditions as those for the above-mentioned Reaction scheme-5a or -5b, though it is desirable to use an acid as the catalyst for hydrolysis and more desirable to use a Lewis acid such a anhydrous aluminum chloride, zinc chloride, iron chloride, tin chloride, or boron trifluoride, or an organic acid such as trifluoroacetic acid.

Reaction scheme-5i

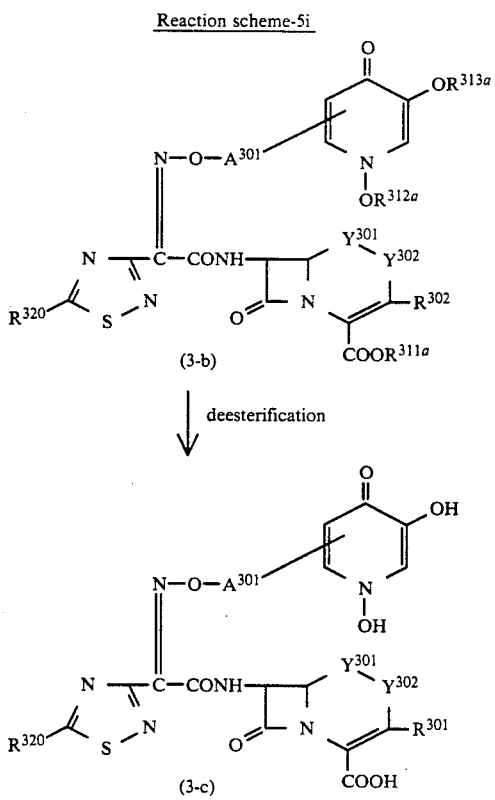

wherein $R^{301}$, $Y^{301}$, $Y^{302}$, and $A^{301}$ are the same as defined above, $R^{311a}$ is the ester residue in $R^{311}$ mentioned above, $R^{312a}$ and $R^{313a}$ are the same group as ester residue of $R^{311a}$, and $R^{320}$ is an amino group which may have the same protective group as mentioned above as $R^{120}$.

The carboxylic acid derivative represented by the general formula (3-c) can be produced by deesterification of the ester compound represented by the general formula (3-b).

The deesterification is conducted either in the absence of solvent or in the presense of appropriate inert solvent, and in the presence of a catalyst for hydrolysis. The inert solvents used include those shown for the above-mentioned Reaction scheme-1a.

The acidic compounds used include Lewis acids such as anhydrous aluminum chloride, stannic chloride, titanium tetrachloride, boron trichloride, boron trifluoride-ethylether complex, zinc chloride and the like; inorganic acids such as hydrochloric acid, nitric acid, sulfuric acid and the like; organic acids such as trichloroacetic acid, trifluoroacetic acid, methanesulfonic acid, acetic acid an the like, and acid-form ion exchange resin; the basic compounds used include organic bases such as trialkylamines (e.g. triethylamine, tributylamine), pyridine, picoline, b 1,5-diazabicyclo[4.3.0]nonene-5, 1,4-diazabicyclo[2.2.2]octane, 18,-diazabicyclo[5.4.0] undecene-7 and the like; and inorganic bases such as alkali metal hydroxides (e.g. sodium hydroxide, potassium hydroxide), alkali metal carbonates e.g. sodium carbonate, potassium carbonate, and the alkali metal hydrogencarbonates e.g. sodium hydrogencarbonate, potassium hydrogencarbonate.

The above-mentioned deesterification can be conducted also through catalytic reduction when $R^{111a}$, $R^{112}$, and $R^{113}$ are ester residues, such as benzyl group, which can be readily removed through catalytic reduction. The catalytic reduction can be conducted according to the procedure described for the Reaction scheme-5a.

Reaction scheme-5j

-continued

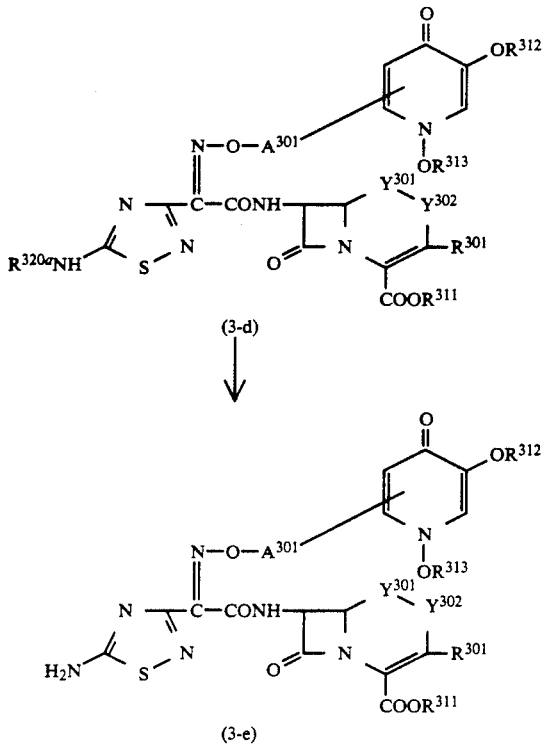

wherein $R^{301}$, $R^{311}$, $R^{312}$, $R^{313}$, $Y^{301}$, $Y^{302}$, and $A^{301}$ are the same as defined above. $R^{320a}$ is the amino protecting group.

The compounds of this invention represented by the general formula (3-e) wherein the 5-position of the thiadiazolyl group is an amino group can be obtained by the reaction of a compound of this invention represented by the general formula (3-d) wherein the 5-position of the thiadiazolyl group is a substituted amino group under essentially the same conditions as those for the deesterification in the above-mentioned Reaction scheme-5g, for example, in the absence of a solvent or in the presence of solvent, and in the presence of an acidic compound or basic compound, or through catalytic reduction.

The solvents used for the said reaction are not specified, including those shown for the Reaction scheme-1a.

The above-mentioned acidic compounds include those shown for the above-mentioned Reaction scheme-5i; desirable acidic compounds include inorganic acids such as hydrochloric acid, hydrobromic acid, sulfuric acid, nitric acid and the like; organic acids such as trifluoroacetic acid, acetic acid formic acid and the like; and acid-form ion exchange resin. Among these acidic compounds liquid ones serve also as solvents.

The basic compounds include organic bases such as trialkylamines e.g. triethylamine, tributylaminen; pyridine, picoline, 1,5-diazabicyclo[4.3.0]nonene-5, 1,4-diazabicyclo[2.2.2]octane and 1.8-diazabicyclo[5.4.0]undecene-7, inorganic bases such as alkali metal hydroxides e.g. sodium hydroxide and potassium hydroxide; alkali metal carbonates e.g. sodium carbonate, potassium carbonate; and alkali metal hydrogencarbonates e.g. sodium hydrogencarbonate, potassium hydrogencarbonate, and urea derivatives, e.g. thiourea, urea.

When water is to be added to the reaction system, it is desirable to use about 10 to 80% by volume of water relative to the acidic or basic compound, followed by addition of 10 to 20 times the volume after completion of the reaction.

The acidic or basic compound and the compound represented by the general formula (3-d) are present in a molar ratio of 1:1 to 100:1, preferably 2:1 to 10:1. The reaction temperature is $-20°$ C. to 80° C., desirably $-10°$ C. to 50° C. The reaction completes in about 1 to 24 hours.

When the reaction according to the Reaction scheme-5h is conducted through catalytic reduction, the conditions for the catalytic reduction, e.g. catalyst for the catalytic reduction, amount of the catalyst, solvent, reaction temperature and reaction time, are the same as those for the catalytic reduction in the Reaction scheme-5a.

Thus amine compound represented by the general formula (3-c) including some of the compound of this invention are obtained.

Reaction scheme-5k

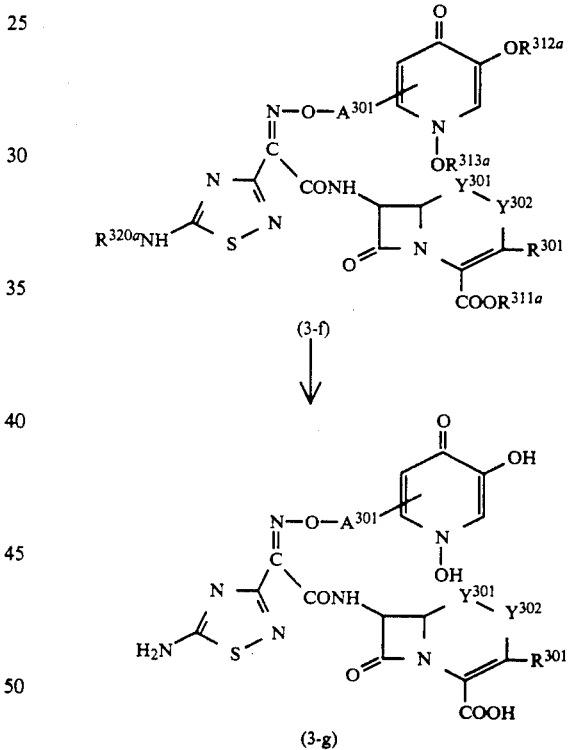

wherein $R^{301}$, $R^{311a}$, $R^{312}$, $R^{313}$, $R^{320a}$, $Y^{301}$, $Y^{302}$, and $A^{301}$ are the same as defined above.

According to this Reaction scheme, deesterification at the 4-position and the removal of the amino-protective group represented by $R^{302a}$ of a compound represented by the general formula (3-f) are conducted at the same time, to give the compound represented by the general formula (3-g), and the reaction can be conducted under essentially the same conditions as those for the above-mentioned Reaction scheme-5i or -5j, though it is desirable to use an acid as the catalyst for hydrolysis, and more desirable to use a Lewis acid such as anhydrous aluminum chloride, zinc chloride, iron chloride, tin chloride, boron trifluoride or the like; or an organic such as trifluoroacetic acid.

Reaction scheme-6a

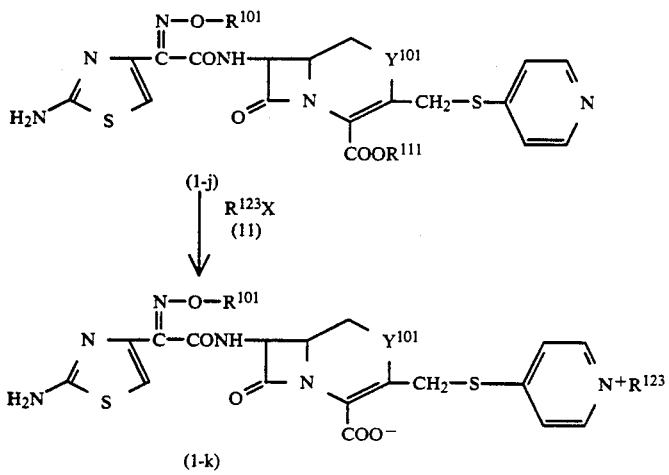

(1-j)

$R^{123}X$
(11)

(1-k)

wherein $R^{101}$, $R^{111}$ and $Y^{101}$ are the same as defined above, X is a halogen atom; and $R^{123}$ is a lower alkyl group, carboxy-lower-alkyl group, hydroxy-lower-alkyl group, amino group, or a group:

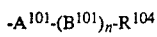
$-A^{101}-(B^{101})_n-R^{104}$ (wherein $A^{101}$, $B^{101}$ and $R^{104}$ are the same as defined above), and n is o.

According to the Reaction scheme-6a, the compound represented by the general formula (1-k) is obtained by reacting the compound represented by the general formula (1-j) with the compound represented by the general formula (11), either in absence of the solvent or in presense of the inert solvent. In the compound represented by the general formula (11), the halogen atom represented by X is exemplified by chlorine, iodine, bromine or fluorine atom.

It is desirable to protect the carboxyl group in the compound represented by the general formula (1-k) by treatment of the compound represented by the general formula (1-j) with a silylating agent prior to the initiation of the reaction. Various lower-alkyl-silylating agents are usable for this purpose, among which N,O-bistrimethylsilylacetamide (BSA) is particularly desirable.

Any solvent may be used unless it exerts adverse effects on the reaction, and such solvents are exemplified by those used for the above-mentioned Reaction scheme-1a.

The silylating agent and the compound represented by the general formula (1-j) are present in a molar ratio of 1:1 to 10:1, preferably 2:1 to 3:1. The reaction temperature is 0° to 60° C., desirably 15° to 20° C., and the reaction completes usually in 5 to 20 hours.

The reaction product is treated with an anion exchange resin, to give a compound of this invention represented by the general formula (1-k).

Reaction scheme-6b

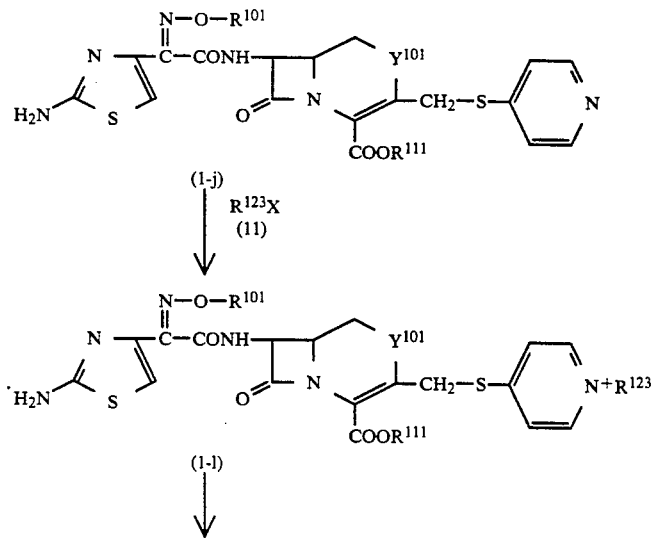

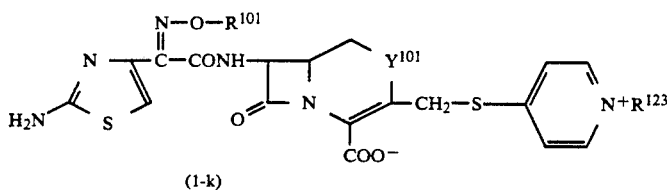

(1-k)

wherein $R^{101}$, $R^{111}$, $R^{123}$, X and $Y^{101}$ are the same as defined above.

Similarly to the above-mentioned Reaction scheme-6a, a compound represented by the general formula (1-j) is react with a compound represented by the general formula (11) to obtain a compound represented by the general formula (1-1), which is then subjected to deesterification using an acidic compound such as trifluoroacetic acid, to give a compound represented by the general formula (1-k).

Reaction scheme-6c

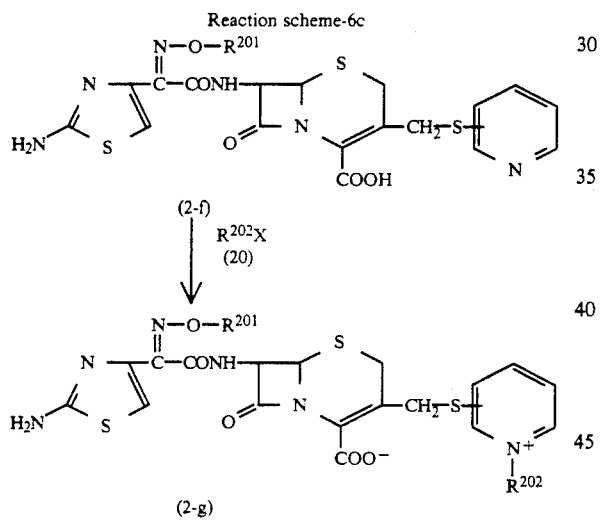

wherein $R^{201}$, $R^{202}$ and X are the same as defined above.

According to the Reaction scheme-6c, the compound represented by the general formula (2-g) is obtained by reacting the compound represented by the general formula (2-f) with a compound represented by the general formula (20), either in the absence of a solvent or in the presence of the inert solvent.

Reaction scheme-6d

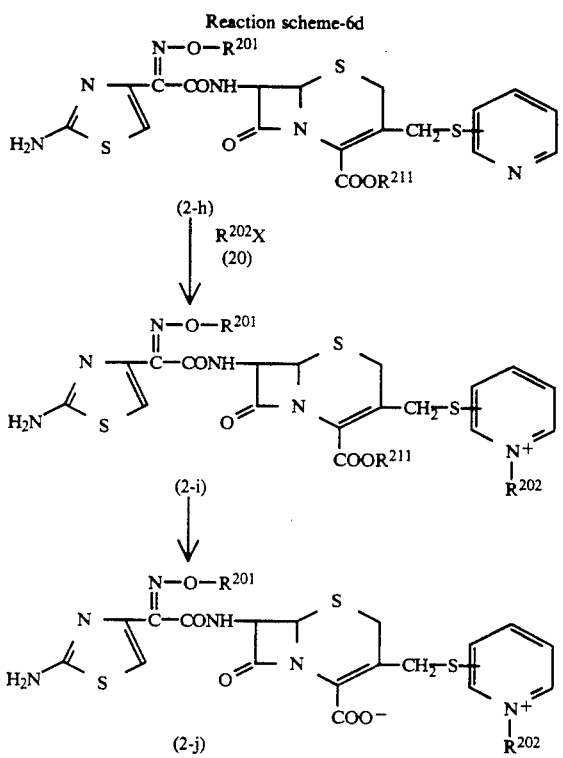

wherein $R^{201}$, $R^{202}$, $R^{211}$ and X are the same as defined above.

According to the Reaction scheme-6d, a compound represented by the general formula (2-h) is allowed to react with a compound represented by the general formula (20) in a similar way to the above-mentioned Reaction scheme-5a, to obtain the compound represented by the general formula (2-i), which is then subjected to deesterification in a similar way to the above-mentioned Reaction scheme-5h, to obtain the compound represented by the general formula (2-j).

Reaction scheme-6e

-continued

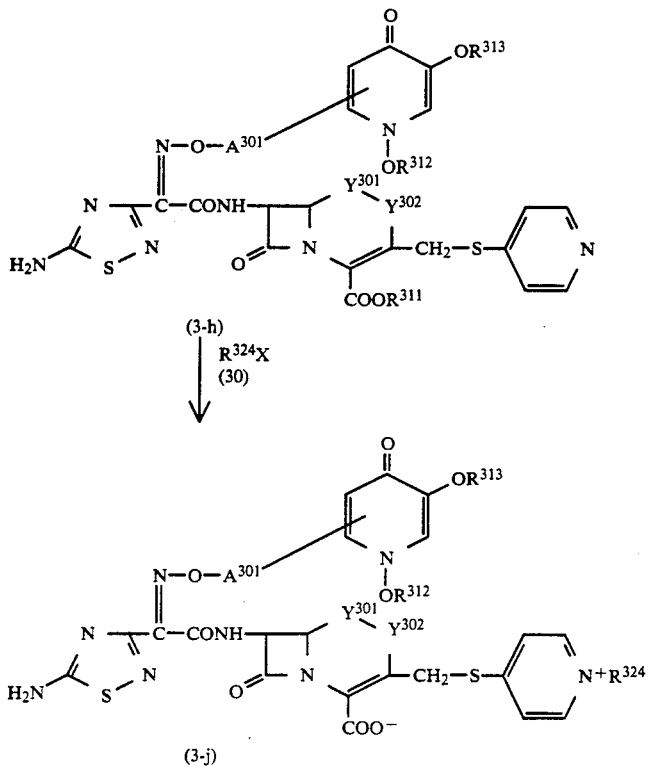

(3-h)

↓ R³²⁴X (30)

(3-j)

wherein $R^{301}$, $R^{311}$, $R^{312}$, $R^{313}$, $Y^{301}$, $Y^{302}$, X and $A^{301}$ are the same as defined above, and $R^{324}$ is a lower alkyl group or carboxy-lower-alkyl group.

According to the Reaction scheme-6e, a compound represented by the general formula (3-j) is obtained by reacting the compound represented by the general formula (3-h) with the compound represented by the general formula (30), either in the absence of a solvent or in the presence of the inert solvent.

It is desirable to protect the carboxyl group in the compound represented by the general formula (3-h) by treatment of the compound represented by the general formula (3-h) with a silylating agent prior to the initiation of the reaction. Various lower-alkyl-silylation agents are use for this purpose, among which N,O-bis-trimethylsilylacetamide (BSA) is particularly desirable.

Any solvent may be use unless it exerts adverse effects on the reaction, and such solvents are exemplified by those used for the above-mentioned Reaction scheme-1c.

The silylating agent and the compound represented by the general formula (3-h) are present in a molar ratio of 1:1 to 10:1, preferably 2:1 to 3:1. The reaction temperature is 0° to 60° C., and the reaction completes usually in 5 to 20 hours.

The reaction product is treated with an anion exchange resin, to obtain a compound of this invention represented by the general formula (3-j).

Reaction scheme-6f

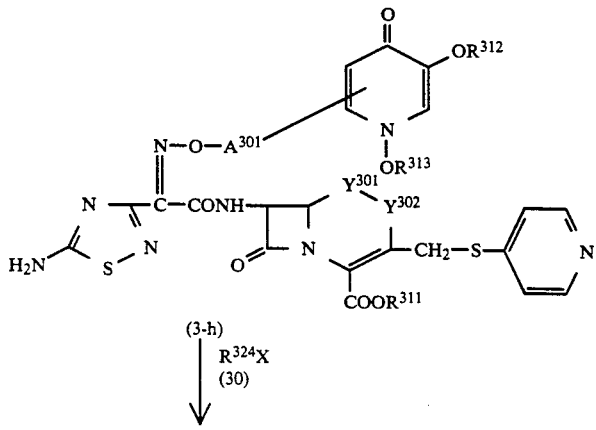

(3-h)

↓ R³²⁴X (30)

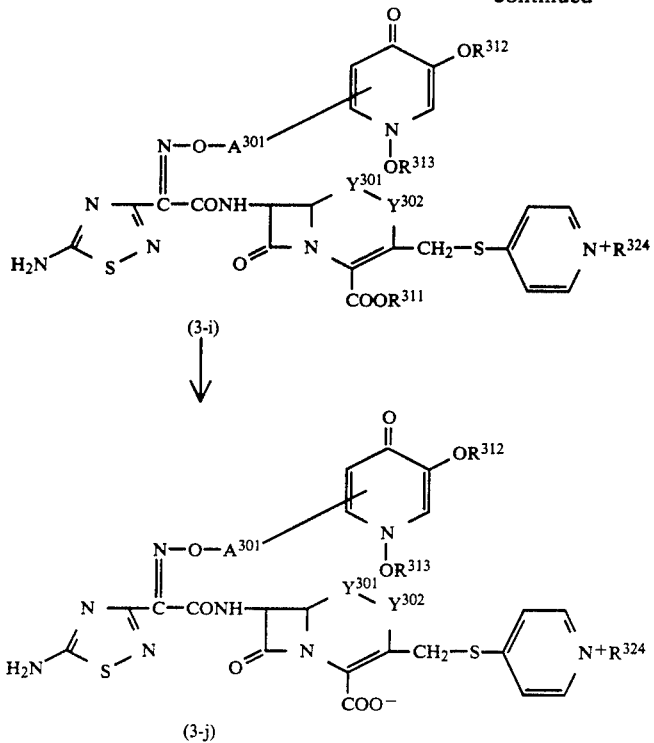

(3-i)

↓

(3-j)

wherein $R^{301}$, $R^{311}$, $R^{312}$, $R^{313}$, $Y^{301}$, $Y^{302}$, X and $A^{301}$ are the same as defined above.

Similarly to the above-mentioned Reaction scheme-6a, a compound represented by the general formula (3-h) is reacted with the compound represented by the general formula (30) to obtain the compound represented by the general formula (3-i), which is then subjected to deesterification using an acidic compound such as trifluoroacetic acid, to obtain a compound represented by the general formula (3-j).

The compounds of this invention represented by the general formula (1), (2), and (3) include of course the optical isomers as well as the syn-isomers and the antiisomers. These isomers can be resolved by usual methods for resolution, for example by the methods using optical resolving agents and the methods using enzymes.

The compounds of this invention are used generally in the form of common pharmaceutical compositions. The compositions are prepared by using diluents or excipients such as fillers, bulking agents, binders, humectants, disintegrators, surfactants, and lubricants. The pharmaceutical compositions can be used in various dosage forms suitable for the therapeutic purpose, and the typical forms include tablets, pills, powders, solutions, suspensions, emulsions, granules, capsules, suppositories, and injections (solutions, suspensions, etc.). For preparation of tablets, the known carriers may be used widely, including excipients such as lactose, sucrose, sodium chloride, glucose, urea, starch, calcium carbonate, kaolin, crystalline cellulose, and silicic acid, binders such as water, ethanol, propanol, simple syrup, glucose solution, starch solution, gelatin solution, carboxymethylcellulose, shellac, methylcellulose, potassium phosphate, and polyvinylpyrrolidone, disintegrators such as dried starch, sodium alginate, agar powder, laminaran powders, sodium hydrogencarbonate, calcium carbonate, polyoxyethylene sorbitan fatty acid esters, sodium lauryl sulfate, stearyl monoglyceride, starch and lactose, disintegration-inhibitors such as sucrose, stearic acid, cacao butter, and hydrogenated oil, absorption enhancers such as quaternary ammonium bases and sodium lauryl sulfate, humectants such as glycerol and starch, adsorbents such as starch, lactose, kaolin, bentonite, and colloidal silicic acid, and lubricants such as purified talc, stearic acid salts, boric acid powders, and polyethyleneglycol. Coated tablets can be prepared if necessary, including sugar-coated tablets, gelatinwrapped tablets, enteric coated tablets, film coated tablets, double coated tablets, and multiple coated tablets. For preparation of pills, the carriers used are those known in this field, including excipients such as glucose, lactose, starch, cacao butter, hydrogenated vegetable oils, kaolin, and talc, binders such as gum arabic powders, powdered tragacanth, gelatin, and ethanol, and disintegrators such as laminaran and agar. For preparation of suppositories, known carriers are widely used, including polyethyleneglycol, cacao butter, higher alcohols and esters of higher alcohols, gelatin, and semisynthetic glycerides. For preparation of injections, solutions, emulsions and suspensions are sterilized and desirably isotonic with blood. All of the diluents which have been used conventionally in this field can be used for preparation of such solutions, emulsions and suspensions, including water, ethyl alcohol, propyleneglycol, isostearyl alcohol ethoxide, polyoxidized isostearyl alcohol, and poly-oxyethylene sorbitan fatty acid esters. Sufficient amount of edible salt, glucose, or glycerol may be included in the pharmaceutical compositions to prepare isotonic solutions, and in addition usual solubilizers, buffering agents, soothing agents, etc., and in addition colorants, preservatives, aromas, flavoring agents, sweetening agents, etc. and other drugs may be added to the therapeutics. For preparation of pastes, creams, and gels, diluents used include white vaseline, paraffin, glycerol, cellulose derivatives, polyethyleneglycol, silicone, and bentonite.

The amount of a compound represented by the general formula or a salt thereof to be included in the pharmaceutical compositions of this invention is not specified and may be selected among the broad range, being usually 1 to 70 weight % in the composition as a whole.

The dose and schedule of administration of the pharmaceutical composition of this invention are not specified, and the composition is administered according to the dosage form, age, sex, and other conditions of the patient, severity of the disease, etc. For example, tablets, pills, solutions, suspensions, emulsions, granules, and capsules are administered orally.

The injections are administered intravenously as they are or as mixtures with usual supplementary solutions such as those containing glucose and amino acids, and may be administered intramuscularly, intracutaneously, subcutaneously, or intraperitoneally. The suppositories are administered into the rectum.

The dose of a pharmaceutical composition of this invention is determined according to the schedule of administration, age, sex and other conditions of the patient, severity of the disease, etc., and the dose of a compound of this invention is usually 1 to 100 mg, desirably 5 to 20 mg, per kg body weight per day, and the daily dose of a composition can be divided into 2 to 4.

EXAMPLES

The invention is illustrated in further details below on the basis of the Reference examples, Examples, Pharmaceutical examples and Antimicrobial activity test.

Reference examples 1 to 10 and Examples 1 to 15 are concerned in the compound represented by the general formula (1); Reference examples 11 and Examples 16 to 19 are concerned in the compound represented by the general formula (2); and Reference examples 12 to 18 and Examples 20 to 27 are concerned in the compounds represented by the general formula (3).

REFERENCE EXAMPLE 1

Benzhydryl(6S,7S)-7-[(Z)-2-(2-tritylaminothiazol-4-yl)-2-(1,5-dibenzhydryloxy-4-pyridone-2-yl-methoxyimino)acetamide]-3-(2-methyl-1,3,4-thiadiazol-5-yl-)thiomethylisocephem-4-carboxylate 1.05 g of benzhydryl(6S,7S)-7-phthalimide-3-(2-methyl-1,3,4-thidiazol-5-yl) thiomethyl-isocephem-4-carboxylate was dissolved in 2 ml of dimethylformamide. Cooling to −10° C., 1 ml of tetrahydrofurane solution of 2M methylhydrazine was dropped. After termination of dropping, the reaction solution was stirred for 40 minutes while keeping at −10° C.

After adding 20 ml of ethyl acetate to the reaction solution, it was washed twice with 20 ml of water and washed once in 20 ml of saturated brine. To this reaction solution, anhydrous sodium sulfate was added, and after removing moisture and filtering, the filtrate was concentrated in vacuo. The obtained concentrate was added to 20 ml of methyl chloride to be dissolved, and after stirring for 2 hours, the insoluble matter precipitated.

Filtering this insoluble matter and while cooling the filtrate with ice, 1.09 g of (Z)-2-(2-tritylaminothiazol-4-yl)-2-(1,5-dibenzhydryloxy-4-pyridone-2-yl-methoxyimino) acetic acid, 0.27 g of 1-hydroxybenzothiazole, and 0.41 g of dicyclohexylcarbodiimide were added to the filtrate in this order. Next, while cooling with ice, the solution was stirred for 3.5 hours, and further stirred for 1.5 hours at room temperature. The insoluble matter was filtered out, and the filtrate was concentrated in vacuo. It was applied to silica gel column chromatograph (elution solvent; methylene chloride:ethyl acetate=1:1), and 0.91 g of the title compound in tiny yellow powder was obtained.

mp: 104° to 106° C.

NMR (CDCl$_3$) δ(ppm):2.66(s, 3H), 2.89(d-d, 1H, J=3Hz, 10Hz), 3.46(d-d, 1H, J=10Hz, 10Hz), 3.90–4.20(m, 1H), 4.87(d, 1H, J=8Hz), 5.30(d, 1H, J=8Hz), 5.75(d-d, 1H, J=4Hz, 8Hz), 5.87(d, 1H, J=11Hz), 6.09(d, 1H, J=11Hz), 6.78(s, 1H), 6.86(s, 1H), 6.91(s, 1H), 6.96(s, 1H), 7.16–7.80(m, 49H).

REFERENCE EXAMPLE 2

Benzhydryl(6S,7S)-7-[(Z)-2-(2-tritylaminothiazol-4-yl)-2-(1,5-dibenzhydryloxy-4-pyridone-2-ylmethoxyimino)acetamide]-3-(1,3,4-thiadiazol-5-yl-)thiomethyl-isocephem-4-carboxylate Using benzhydryl(6S,7S)-7-phthalimide-3-(1,3,4-thiadiazol-5-yl)thiomethyl-isocephem-4-carboxylate, the title compound in tiny yellow powder was obtained in the same manner as in Reference example 1.

mp: 102°–105° C.

NMR (CDCl$_3$) δ(ppm): 2.70–3.00(m, 1H), 3.46(dd, 1H, J=11Hz, 10Hz), 3.93–4.10(m, 1H), 4.87(d, 1H, J=9Hz), 5.28(d, 1H, J=9Hz), 5.72(dd, 1H, J=4Hz, 9Hz), 5.96(s, 2H), 6.76(s, 1H), 6.85(s, 1H), 6.90(s, 1H), 6.91(s, 1H), 7.00–7.90(m, 49H), 8.92(s, 1H).

REFERENCE EXAMPLE 3

Benzhydryl(6S,7S)-7-[(Z)-2-(tritylaminothiazol-4-yl)-2-(1,5-dibenzhydryloxy-4-pyridone-2-ylmethoxyimino)acetamide]-3-methylisocephem-4-carboxylate Using benzhydryl(6S,7S)7-phthalimide-3-methylisocephem-4-carboxylate, the title compound in yellow powder was obtained in the same manner as in Reference example 1.

mp:103°–107° C.

NMR (CDCl$_3$) δ(ppm): 2.24(s, 3H), 2.70(d-d, 1H, J=3Hz, J=12Hz), 3.07(d-d, 1H, J=11Hz, J=12Hz), 4.07–4.28(m, 1H), 4.71(d, 1H, J=13Hz), 4.93(d, 1H, J=13Hz), 5.43(d-d), 1H, J=4Hz, 6Hz), 5.95(s, 1H), 6.13(s, 1H), 6.34(s, 1H), 6.72(s, 1H), 6.84(s, 1H), 6.90(s, 1H), 6.94(s, 1H), 7.05–7.80(m, 48H).

REFERENCE EXAMPLE 4

Benzhydryl(6S,7S)-7-[(Z)-2-(2-tritylaminothiazol-4-yl)-2-(1,5-dibenzhydryloxy-4-pyridone-2-yl-methoxyimino)acetamide]-3-(1,2,3-thiadiazol-5-yl)thiomethylisocephem-4-carboxylate Using benzhydryl(6S,7S)-7-phthalimide-(1,2,3-thiadiazol-5-yl)thiomethylisocephem-4-carboxylate, the title compound was obtained in the same manner as in Reference example 1.

NMR (CDCl$_3$) δ(ppm): 2.63–2.90(m, 1H), 3.00–3.30(m, 1H), 3.80–4.00(m, 1H), 4.68(d, 1H, J=13Hz), 4.87(d, 1H, J=13Hz), 5.47(d-d, 1H, J=4Hz, J=6Hz), 5.90(s, 1H), 6.12(s, 1H), 6.30(s, 1H), 6.75(s, 1H), 6.86(s, 1H), 6.87(s, 1H), 6.94(s, 1H), 7.10–7.90(m, 47H), 8.13(d, 1H, J=6Hz), 8.38(s, 1H).

REFERENCE EXAMPLE 5

Benzhydryl(6S,7S)-7-[(Z)-2-(2,2-dimethylbenzodioxol-5-yl)-methoxyimino-2-(2-tritylaminothiazol-4-yl)]acetamide-3-(2-methyl-1,3,4-thiadiazol-5-ylthiomethyl)isocephem-4-carboxylate Using benzhydryl(6S,7S)-7-phthalimide-3-(2-methyl-1,3,4-thiadiazol-5-ylthiomethyl)isocephem-4-carboxylate and (Z)-2-(2,2-dimethylbenzodioxol-5-yl)-methoxyimino-2-(2-tritylaminothiazol-4-yl)acetic acid, the title compound in tiny yellow powder was obtained in the same manner as in Reference example 1.

mp: 108°–111° C. (change color).

NMR (CDCl$_3$) δ(ppm): 1.63(s, 6H), 2.66(s, 3H), 2.83–3.24(m, 2H), 3.80–4.00(m, 1H), 4.30(d, 1H, J=12Hz), 4.70(d, 1H, J=12Hz), 5.10(s, 2H), 5.52(dd, 1H, J=6Hz, J=6Hz), 6.65(d, 1H, J=9Hz), 6.70(s, 1H), 6.74(s, 1H), 6.77(d, 1H, J=9Hz), 6.91(s, 1H), 7.03–7.60(m, 27H).

REFERENCE EXAMPLE 6

Benzhydryl(6S,7S)j-7-{(Z)-2-[t-butoxycarbonyl(2,2-dimethylbenzodioxol-5-yl)]methoxyimino-2-(2-tritylaminothiazol-4-yl)}acetamide-3-(2-methyl-1,3,4-thiadiazol-5-ylthiomethyl)isocephem-4-carboxylate Using benzhydryl(6S,7S)-7-phthalimide-3-(2-methyl-1,3,4-thiadiazol-5-ylthiomethyl)isocephem-4-carboxylate and (Z)-2-[t-butoxycarbonyl-(2,2-dimethylbenzodioxol-5-yl)]methoxyimino-2-(2-tritylaminothiazol-4-yl) acetic acid, the title compound in tiny yellow powder was obtained in the same manner as in Reference example 1.

mp: 112°–115° C. (change color).

NMR (CDCl$_3$) δ(ppm): 1.48(s, 9H), 1.60(s, 6H), 2.62(s, 3H), 2.99–3.25(m, 2H), 3.81–4.05(m, 1H), 4.28(d, 1H, J=14Hz), 4.71(d, 1H, J=14Hz), 5.49(dd, 1H, J=5Hz, J=6Hz), 5.81–5.93(m, 1H), 6.64(d, 1H, J=10Hz), 6.71(s, 1H), 6.78(d, 1H, J=10Hz), 6.83(s, 1H), 6.91(s, 1H), 7.03–7.60(m, 27H).

REFERENCE EXAMPLE 7

Benzhydryl(6S,7S)-7-[(Z)-2-(2-tritylaminothiazol-4-yl)-2-(1,5-dibenzhydryloxy-4-pyridone-2-ylmethoxyimino)acetamide]-3-[1-benzhydryloxycarbonylmethyl-1H-tetrazole-5-ylthiomethyl)isocephem-4-carboxylate Using benzhydryl(6S,7S)-7-phthalimide-3-(1-benzhydryloxycarbonylmethyl-1H-tetrazole-5-ylthiomethyl)isocephem-4-carboxylate, the title compound in brown powder was obtained in the same manner as in Reference example 1.

mp: 119°–134° C. (change color).

NMR (CDCl$_3$) δ(ppm): 2.68(dd, 1H, J=3Hz, 10Hz), 3.10(dd, 1H, J=10Hz, 11Hz), 4.72–4.98(m, 1H), 4.26(d, 1H, J=15Hz), 4.48(d, 1H, J=15Hz), 4.70(d, 1H, J=14Hz), 4.85(d, 1H, J=14Hz), 4.96(s, 2H), 5.47(dd, 1H, J=5Hz, 7Hz), 5.86(s, 1H), 6.08(s, 1H), 6.25(s, 1H), 6.76(s, 1H), 6.86(s, 2H), 6.91(d, 1H, J=7Hz), 7.00–7.90(m, 57H).

REFERENCE EXAMPLE 8

Benzhydryl(6S,7S)-7-[(Z)-2-(2-tritylaminothiazol-4-yl)-2-(1,5-dibenzhydryloxy-4-pyridone-2-ylmethoxyimino)acetamide]-3-(2-tritylamino-1,3,4-thiadiazol-5-ylthiomethyl)isocephem-4-carboxylate Using benzhydryl(6S,7S)-7-phthalimide-3-(2-tritylamino-1,3,4-thiadiazol-5-ylthiomethyl)isocephem-4-carboxylate, the title compound in yellow powder was obtained in the same manner as in Reference example 1.

mp: 114°–145° C. (change color).

NMR (CDCl$_3$) δ(ppm): 2.66(dd, 1H, J=3Hz, 12Hz), 3.67(dd, 1H, J=12Hz, 12Hz), 3.72–3.93(m, 1H), 4.27(d, 1H, J=15Hz), 4.58(d, 1H, J=15Hz), 4.77(bs, 2H), 5.43(dd, 1H, J=6Hz, 6Hz), 5.95(s, 1H), 6.09(s, 1H), 6.32(s, 1H), 6.76(s, 1H), 6.82(s, 1H), 6.93(s, 1H), 6.96(s, 1H), 6.90–7.92(m, 61H), 8.20(d, 1H, J=6Hz).

REFERENCE EXAMPLE 9

Benzhydryl (6S,7S)-7-[(Z)-2-(2-tritylaminothiazol-4-yl)-2-(1,5-dibenzyhydryloxy-4-pyridone-2-ylmethoxyimino)acetamide]-3-[1-(2-hydroxyethyl)-1H-tetrazol-5-ylthiomethyl]isocephem -4-carboxylate Using benzhydryl(6S,7S)-7-phthalimide-3-[1-(2-hydroxyethyl)-1H-tetrazol-5-ylthiomethyl]isocephem-4-carboxylate, the title compound in brown powder was obtained in the same manner as in Reference example 1.

mp: 124°–138° C. (change color).

NMR (CDCl$_3$) δ (ppm): 2.40(dd, 1H, J=3Hz, 10Hz), 3.00(dd, 1H, J=10Hz, 11Hz), 3.65–5.16(m, 7H), 5.56(dd, 1H, J=5Hz, 6Hz), 5.57(d, 1H, J=19Hz), 5.84(d, 1H, J=19Hz), 6.02(bs, 1H), 6.43(s, 1H), 6.81(d, 1H, J=6Hz), 6.88(s, 2H), 6.92(s, 2H), 7.05–7.96(m, 46H).

REFERENCE EXAMPLE 10

(6S, 7S)-7-[(Z)-2-(2-aminothiazol-4-yl)-2-methoxyiminoacetamide]-3-[(1-carboxymethyl-4-pyridinio)thiomethyl]isocephem-4-carboxylate To 1.00 g of benzhydryl(6S,7S)-7-[(Z)-2-(2-amiinothiazol-4-yl)-2-methoxyiminoacetamide]-3-(pyridine-4-ylthiomethyl)isocephem-4-carboxylate, 3 ml of anisole and then 5.5 ml of trifluoroacetic acid were added with ice-cold state, and stirred. After 10 minutes, 50 ml of isopropylether was added to precipitate a crystal, which was filtered, washed in isopropylether, and dried in vacuo to obtain a crystal.

1.15 g of this crystal was dissolved in 7 ml of N,N-dimethylformamide, and 1.45 ml of N,O-bistrimethylsilylacetamide was added to this solution with ice-cooling. To this mixture, 1 ml of N,N-dimethylformamide solution of 0.61 g of bromacetic acid and 1.1 ml of N,O-bistrimethylsilylacetamide was added. The obtained mixed solution was stirred at room temperature for 15 hours, 2 ml of methyl alcohol was added with ice-cooling, then 50 ml of isopropyl alcohol was added to obtain a crystal. The precipitating crystal was washed with isopropyl alcohol, and dried in vacuo. 0.64 g of this crystal was dissolved in 5% sodium hydrogencarbonate aqueous solution, and a proper amount of nonionic adsorbent resin (HP-20) was added, and 10% HCl aqueous solution was added to adjust the pH to 2 to adsorb. Filling the column with this solution, washing sufficiently in water, it was eluted in 5 to 20% isopropyl alcohol aqueous solution. The eluate was concentrated in vacuo, and 0.36 g of the title compound in tiny yellow powder was obtained.

mp: 184°–188° C. (decomposed).

NMR (DMSO-d6) δ (ppm): 2.96–3.43(m, 2H), 3.85–4.12(m, 1H), 3.88(s, 3H), 4.60(s, 2H), 4.96(s, 2H), 5.62(dd, 1H, J=5Hz, J=8Hz), 6.83(s, 1H), 7.23(brS, 2H), 8.03(d, 2H, J=6Hz), 8.62(d, 2H, J=6Hz), 9.20(d, 1H, J=8Hz).

REFERENCE EXAMPLE 11

Benzhydryl(6S,7S)-7-[(Z)-2-(2-aminothiazol-4-yl)-2-methoxyiminoacetamide]-3-(pyridine -4-ylthiomethyl) isocephem-4-carboxylate 2.48 g of benzhydryl(6S,7S)-7-phthalimide-3-(pyridine-4-ylthiomethyl)-isocephem-4-carboxylate was dissolved in a mixed solution consisting of 15 ml of tetrahydrofurane and 15 ml of dimethylformamide, and the solution was cooled to −15° C. Adding 0.26 ml of methylhydrazine, the solution was stirred at −15 deg. C. for 2 hours. In succession, to the reaction mixed solution, 30 ml of ethyl acetate and 30 ml of water were added, and the solution was separated. 15 ml of ethyl acetate was added to the water part to extract. Adding to the organic solvent part, the mixture was washed three times with 30 ml of water, and then washed once in 30 ml of saturated brine. After washing, anhydrous sodium sulfate was added to the mixture to remove water, and the mixture was filtered, and the filtrate was concentrated in vacuo. The residue was dissolved in 27 ml of methylene chloride, and the solution was stirred for 2 hours, and the precipitate was filtered out. 1.40 g of benzothiazol-2-yl(Z)-2-(2-aminothiazol-4-yl)-2-methoxyiminothioacetic acid was added to the filtrate, and the mixture was stirred at room temperature for 15 hours.

The reaction solution was washed with 30 ml of water, with 30 ml of 5% sodium hydrogencarbonate aqueous solution and with 30 ml of water for twice, and anhydrous sodium sulfate was added to the solution to remove water.

The remaining solution was filtered, the filtrate was dried to solid in vacuo, and the residue was applied to the silica gel chromatography (elution solvent: ethyl acetate), and 1.81 g of the title compound in white powder was obtained.

mp: 232°-235° C. (decomposed).

NMR (CDCl3, DMSO-d6) δ (ppm): 3.06-3.42(m, 2H), 3.95(s, 3H), 3.82-4.18(m, 1H), 4.19(d, 1H, J=13Hz), 4.37(d, 1H, J=13Hz), 5.77(dd, 1H, J=9Hz, J=6Hz), 6.82(s, 1H), 6.78-7.02(brs, 2H), 6.92(s, 1H), 7.18(d, 2H, J=6Hz), 7.08-7.67(m, 10H), 8.37(d, 2H, J=6Hz), 9.23(d, 1H, J=9Hz).

REFERENCE EXAMPLE 12

(Z)-2-(5-Amino-1,2,4-thiadiazol-3-yl)-2-(1,5-dibenzhydryloxy-4-pyridone-2-ylmethoxyimino) acetic acid 3.5 g of 2-phthalimidoxymethyl-1,5-dibenzhydryloxy-4-pyridone was suspended in 35 ml of ethanol, and 0.27 ml of hydrazine hydrate was added. The solution was heated and refluxed for 1 hour. After cooling to room temperature, the insoluble matter was filtered away from the solution, and the filtrate was concentrated and dried. The residue was suspended in 50 ml of chloroform, the insoluble matter was filtered away, and the filtrate was concentrated and dried. The residue was dissolved in 50 ml of methanol, and 0.95 g of 2-(5-amino-1,2,4-thiadiazol-3-yl)-2-oxoacetic acid was added. The mixture was stirred at room temperature for 2 hours. After distilling away the solvent, ether was added to the residue, and white powder was filtered out, and 3.31 g of the title compound was obtained.

mp: 145°-147° C.

NMR (DMSO-d6) δ (ppm): 4.88(2H, s), 6.01(1H, s), 6.31(1H, s), 6.35(1H, s), 7.34(20H, bs), 7.53(1H, s), 8.12(2H, bs).

REFERENCE EXAMPLE 13

Benzhydryl(6S,7S)-7-[(Z)-2-(5-amino-1,2,4-thiadiazol-3-yl)-2-(1,5-dibenzhydryloxy -4-pyridone-2-ylmethoxyimino)acetamide]-3-(5-benzhydryloxycarbonylmethyl-4-methylthiazol-2-ylthiomethyl) isocephem-4-carboxylate 1.18 g of benzhydryl(6S,7S)-7-phthalimide-3-(5-benzhydryloxycarbonylmethyl-4-methylthiazol -2-ylthiomethyl)isocephem-4-carboxylate was dissolved in 2 ml of dimethylformamide. Cooling to −10° C., 1 ml of tetrahydrofurane solution was 2M methylhydrazine was dropped. After termination of dropping, the reaction solution was stirred for 40 minutes with keeping at −10° C.

To this reaction solution, 20 ml of ethyl acetate and 20 ml of water were added, and the solution was shaken and separated. This ethyl acetate was washed in saturated brine, and dried with anhydrous sodium sulfate, and the solvent was distilled away, and benzhydryl(6S,7S)-7-amino-3-(5-benzhydryloxycarbonylmethyl-4-methylthiazol-2-ylthiomethyl)isocephem -4-carboxylate was obtained. It was dissolved in 20 ml of dimethylformamide. 0.9 g of (Z)-2-(5-amino-1,2,4-thiadiazol-3-yl)-2-(1.5-dibenzhydryloxy-4-pyridone-2-ylmethoxyimono)acetic acid. 0.18 g of 1-hydroxybenzotriazole were added, and further 0.28 g of dicyclohexylcarbodiimide was added to the solution with ice-cooling for reacting for 15 hours at room temperature. Then the insoluble matter was filtered away, and the filtrate was extracted in 200 ml of ethyl acetate and 200 ml of water. Successively, the ethyl acetate was washed in saturated brine, dried with anhydrous sodium sulfate, and concentrated. The concentrate was applied to the silica gel chromatography (elution solvent; chloroform:methanol=20:1) for purifivation, and 0.9 g of the title compound in tiny yellow powder was obtained.

mp: 117°-120° C.

NMR (DMSO-d6) δ (ppm): 2.18(3H, s), 2.66-3.18 (2H, m), 3.79-4.11(1H, m), 4.01(2H, s), 4.36(2H, q), 4.86(2H, s), 5.70(1H, dd), 6.08(1H, s), 6.32(1H, s), 6.35(1H, s), 6.81(1H, s), 6.84(1H, s), 6.95-7.70(41H, m), 8.16(2H, bs), 9.37(1H, d)

REFERENCE EXAMPLE 14

Benzhydryl(6R,7R)-7-[(Z)-2-(5-amino-1,2,4-thiadiazol-3-yl)-2-(1,5-dibenzhydryloxy -4-pyridone-2-ylmethoxyimino)acetamide]-3-(5-benzhydryloxycarbonylmethyl-4-methylthiazol-2-ylthiomethyl) -3-cephem-4-carboxylate Using benzhydryl(6R,7R)-7-amino-3-(5-benzhydryloxycarbonylmethyl-4-methylthiazol-2-ylthiomethyl) -3-cephem-4-carboxylate as the starting material, the title compound in tiny yellow color was obtained in the same manner as in Reference example 13.

mp: 112°-115° C.

NMR (CDCl3) δ (ppm): 2.19(3H, s), 3.61(2H, q), 3.69(2H, s), 4.22(2H, q), 4.7-5.1(3H, m), 5.79(1H, dd), 5.82(2H, bs), 5.95(1H, s), 6.07(1H, s), 6.48(1H, s), 6.66(1H, s), 6.88(1H, s), 7.24(40H, s), 7.51(1H, s).

REFERENCE EXAMPLE 15

Benzhydryl(6S,7S)-7-[(Z)-2-(5-amino-1,2,4-thiadiazol-3-yl)-2-(1,5-dibenzhydryloxy-4-pyridone-2-ylmethoxyimino)acetamide]-3-(1-benzhydryloxycarbonylmethyl-1H-tetrazol-5-ylthiomethyl)-isocephem-4-carboxylate Using benzhydryl(6S,7S)-7-phthalimide-3-(1-benzhydryloxycarbonylmethyl-1H-tetrazol-5-ylthiomethyl) isocephem-4-carboxylate as the starting material, the title compound in tiny yellow powder was obtained in the same manner as in Reference example 13.

mp: 118°–120° C.

NMR (DMSO-d6) δ (ppm): 2.71–3.16(2H, m), 3.71–4.15(1H, m), 4.32(2H, q), 4.88(2H, s), 5.64(2H, s), 5.71(1H, dd), 6.11(1H, s), 6.34(1H, s), 6.37(1H, s), 6.83(1H, s), 6.88(1H, s), 6.91–7.68(41H, m), 8.15(2H, bs), 9.35(1H, d).

REFERENCE EXAMPLE 16

Para-methoxybenzyl(6R,7R)-7-[(Z)-2-(5-amino-1,2,4-thiadiazol-3-yl)-2-(1,5-dibenzhydryloxy-4-pyridone-2-ylmethoxyimino)acetamide]-3-(1-benzhydryloxycarbonylmethyl-1H-tetrazol-5-ylthiomethyl)-3-cephem-4-carboxylate Using paramethoxybenzyl(6R,7R)-7-amino-3-(1-dibenzhydryloxycarbonylmethyl-1H-tetrazole-5-ylthiomethyl)-3-cephem-4-carboxylate as the starting material, the title compound in tiny yellow powder was obtained in the same manner as in Reference example 13.

mp: 121°–125° C.

NMR (DMSO-d6) δ (ppm): 3.37(2H, q), 3.75(3H, s), 4.32(2H, q), 4.84(2H, s), 5.01(1H, d), 5.19(2H, s), 5.65(2H, s), 5.78(1H, dd), 6.30(1H, s), 6.41(1H, s), 6.43(1H, s), 6.88(1H, s), 6.89(2H, d), 7.34(32H, s), 7.88(1H, s), 8.14(2H, bs), 9.67(2H, d).

REFERENCE EXAMPLE 17

Benzhydryl(6S,7S)-7-[(Z)-2-(5-amino-1,2,4-thiadiazol-3-yl)-2-(1,5-dibenzhydryloxy-4-pyridone-2-ylmethoxyimino)acetamide]-3-(4-carboxy-3-hydroxyisothiazol-5-ylthiomethyl)isocephem-4-carboxylate 1.18 g of benzhydryl(6S,7S)-7-phthalimide-3-(4-carboxy-3-hydroxyisothiazol-5-ylthiomethyl)-isocephem-4-carboxylate was dissolved in 2 ml of dimethylformamide, and cooling to −10° C., 1 ml of tetrahydrofurane solution of 2M methylhydrazine was dropped to the solution. After termination of dropping, the reaction solution was stirred for 40 minutes with keeping at −10° C.

The reaction solution was added to 50 ml of water, and the produced powder was filtered and dried, thereby obtaining benzhydryl(6S,7S)-7-amino-3-(4-carboxy-3-hydroxyisothiazol-5-ylthiomethyl)isocephem-4-carboxylate.

This powder was dissolved in 2 ml of dimethylformamide, and 0.85 ml of N,O-bistrimethylsilylacetamide was added. The mixture was stirred at room temperature for 30 minutes to obtain solution (A).

1.13 g of (Z)-2-(5-amino-1,2,4-thiadiazol-3-yl)-2-(1,5-dibenzhydryloxy-4-pyridone-2-ylmethoxyimino)acetic acid was dissolved in 5 ml of dimethylformamide. 0.23 g of 1-hydroxybenzotriazole and 0.36 g of dicyclohexylcarbodiimide were added in this order with ice cooling, and the mixture was stirred for 1 hour at room temperature. The insoluble matter was filtered away, and solution (A) was added to the filtrate and reacting for 15 hours at room temperature.

This reaction solution was added to 100 ml of water, and the produced powder was filtered, and was applied on the silica gel column chromalography (elution solvent; chloroform:methanol:water=100:10:1), thereby producing 0.91 g of the title compound in tiny yellow color.

m.p. 108° C.

NMR (DMSO-d6) δ (ppm): 2.60–3.21(2H, m), 3.72–4.01(1H, m), 4.31(2H, q), 4.84(2H, s), 5.69(1H, dd), 6.01(1H, s), 6.36(1H, s), 6.41(1H, s), 6.80(1H, s), 6.89–7.68(1H, m), 8.14(2H, bs), 9.31(1H, d).

REFERENCE EXAMPLE 18

Paramethoxybenzyl(6R,7R)-7-[(Z)-2-(5-amino-1,2,4-thiadiazol-3-yl)-2-(1,5-dibenzhydryloxy-4-pyridone-2-ylmethoxyimino)acetamide]-3-(4-carboxy-3-hyroxyisothiazol-5-ylthiomethyl)-3-cephem-4-carboxylate Using paramethoxybenzyl(6R,7R)-7-amino-3-(4-carboxy-3-hydroxyisothiazol-5-ylthiomethyl)-3-cephem-4-carboxylate as the starting material, the title compound in tiny yellow color was obtained in the same manner as in Reference example 17.

mp: 111° C. (change color).

NMR (DMSO-d6) δ (ppm): 3.41(2H, q), 3.81(3H, s), 4.29(2H, q), 4.85(2H, s), 5.05(1H, d), 5.16(2H, s), 5.71(1H, dd), 6.29(1H, s), 6.38(1H, s), 6.43(1H, m), 6.91(1H, d), 7.15–7.68(23H, m), 8.13(2H, bs), 9.66(1H, d).

EXAMPLE 1

(6S,7S)-7-[(Z)-2-(2-Aminothiazol-4-yl)-2-(1,5-dihydroxy-4-pyridone-2-ylmethoxyimino)acetamide]-3-(2-methyl-1,3,4-thiadiazol-5-yl)thiomethyl-isocephem-4-carboxylic acid To 0.83 g of benzhydryl(6S,7S)-7-[(Z)-2-(2-tritylaminothiazol-4-yl)-2-(1,5-dibenzhydryloxy-4-pyridone-2-ylmethoxyimino)acetamide]-3-(2-methyl-1,3,4-thiadiazol-5-yl-)thiomethyl -isocephem-4-carboxylate obtained in Reference example 1, 0.4 ml of anisol and 4 ml to trifluoroacetic acid were added, and the mixture was stirred at room temperature for 2 hours.

20 ml of diisopropylether was added to the mixture, and a powdery solid was obtained. This powdery solid was filtered, sufficiently washed in diisopropylether and was dried in vacuo. The residue wa dissolved in 5% sodium hydrogencarbonate aqueous solution, and a proper amount of nonionic absorbent resin (HP-20) was added, and the pH was adjusted to 2 by 10% HCl aqueous solution to adsorb. Filling the column with it and washing sufficiently with water, it was eluted in 5 to 20% isopropyl alcohol. The eluate was concentrated in vacuo, and 0.24 g of the title compound in white powder was obtained.

mp: 115 deg. C. (change color).

NMR (DMSO-d6) δ (ppm): 2.72(s, 3H), 3.00–3.32(m, 2H), 3.65–4.18(m, 1H), 4.35(d, 1H, J=13Hz), 4.62(d,1H, J=13Hz), 5.18(s, 2H), 5.68(d,d, 1H, J=4Hz, J=9Hz), 6.75(s, 1H), 6.87(s, 1H), 7.25(bs, 2H), 7.74(s, 1H), 9.38(d, 1H, J=9Hz).

EXAMPLE 2

(6S,7S)-7-[(Z)-2-(2-Aminothiazol-4-yl)-2-(1,5-dihydroxy-4-pyridone-2-ylmethoxyimino)acetamide]-3-(1,3,4-thiadiazol-5-yl)thiomethyl-isocephem-4-carboxylic acid.

Using benzhydryl(6S,7S)-7-[(Z)-2-(2-tritylaminothiazol-4-yl)-2-(1,5-dibenzyhydryloxy -4-pyridone-2-ylmethoxyimino)acetamide]-3-(1,3,4-thiadiazol-5-yl)thiomethyl-isocephem-4-carboxylate obtained in Reference example 2, the title compound in light yellow powder was obtained in the same manner as in Example 1.

mp: 112° C. (change color).

NMR (DMSO-d6) δ (ppm): 3.00–3.36(m, 2H), 3.70–4.18(m, 1H), 4.42(d, 1H, J=12Hz), 4.70(d, 1H, J=12Hz), 5.19(s, 2H), 5.69(dd, 1H, J=5Hz, 9Hz), 6.75(s, 1H), 6.88(x, 1H), 7.25(bs, 2H), 7.76(s, 1H), 9.38(d, 1H, J=9Hz), 9.57(s, 1H).

EXAMPLE 3

(6S,7S)-7-[(Z)-2-(2-aminothiazol-4-yl)-2-(1,5-dihydroxy-4-pyridone-2-ylmethoxyimino)acetamide]-3-methylisocephem-4-carboxylate sodium salt Using benzhydryl(6S,7S)-7-[(Z)-2-(2-tritylaminothiazol-4-yl)-2-(1,5-dibenzhydryloxy -4-pyridone-2-ylmethoxyimino)acetamide]-3-methylisocephem-4-carboxylate obtained in Reference example 3, the title compound in light orange powder was obtained in the same manner as in Example 1.

mp: 147° C. (change color).

NMR (DMSO-d6) δ (ppm): 1.91(s, 3H), 2.5–3.2(m, 2H), 5.00(bs, 2H), 5.22(d, 1H, J=4Hz), 6.17(s, 1H), 6.82(s, 1H), 7.21(s, 1H).

EXAMPLE 4

(6S,7S)-7-[(Z)-2-(2-aminothiazol-4-yl)-2-(1,5-dihydroxy-4-pyridone-2-ylmethoxyimino)acetamide]-3-(1,2,3-thiadiazol-5-yl)thiomethylisocephem-4-carboxylic acid Using benzhydryl(6S,7S)-7-[(Z)-2-(2-tritylaminothiazol-4-yl)-2-(1,5-dibenzhydryloxy -4-pyridone-2-ylmethoxyimino)acetamide]-3-(1,2,3-thiadiazol-5-yl)thiomethylisocephem-4-carboxylate obtained in Reference example 4, the title compound was obtained in the same manner as in Example 1.

NMR (DMSO-d6) δ (ppm): 3.00–3.40(m, 2H), 3.82–4.20(m, 1H), 4.37(s, 2H), 5.20(bs, 2H), 5.68(dd, 1H, J=5Hz, J=9Hz), 6.77(s, 1H), 6.89(s, 1H), 7.26(bs, 2H), 7.76(s, 1H), 8.93(s, 1H), 9.45(d, 1H, J=9Hz).

EXAMPLE 5

(6S,7S)-7-[(Z)-2-(2-aminothiazol-4-yl)-2-(1-carboxy-1-methylethoxy)iminoacetamide]-3-{[1-[2-(3,4-dihydroxyphenyl)-2-oxo]ethyl]-4-pyridinio}thiomethylisocephem-4-carboxylate Using benzhydryl(6S,7S)-7-[(Z)-2-(2-aminothiazol-4-yl)-2-(1-t-butoxycarbonyl-1-methylethoxy)iminoacetamide]-3-(pyridine-4-yl)thiomethylisocephem-4-carboxylate and 2-iode-3',4'-dihydroxyacetophenone, the title compound in tiny red powder was obtained in the same manner as in Reference example 10.

mp: 172° C. (change color).

NMR (DMSO-d6) δ (ppm):
1.42(s, 6H), 2.80–3.40(m, 1H), 3.80–4.12(m, 1H), 4.61(s, 2H), 4.32–4.60(m, 1H), 5.68(dd, 1H, J=5Hz, J=8Hz), 6.18(bs, 2H), 6.80(s, 1H), 6.99(d, 1H, J=7Hz), 7.28(bs, 2H), 7.46(s, 1H), 7.51(d, 1H, J=7Hz), 8.15(d, 2H, J=5Hz), 8.68(d, 2H, J=5Hz), 9.12(d, 1H, J=8Hz).

EXAMPLE 6

(6S,7S)-7-[(Z)-2-(2-aminothiazol-4-yl)-2-(1-carboxy-1-methylethoxy)imino]acetamide]-3-[1-(N-3,4-dihydroxybenzamide)carbamoylmethyl-4-pyridinio]thiomethylisocephem-4-carboxylate To 2.37 g of benzhydryl(6S,7S)-7-[(Z)-2-(2-aminothiazol-4-yl)-2-(1-t-butoxycarbonyl -1-methylethoxy)iminoacetamide]-3-(pyridine-4-ylthiomethyl)isocephem-4-carboxylate, 4 ml of anisol and 16 ml of trifluoroacetic acid were added with ice-cooling. After reacting for 90 minutes at room temperature, 100 ml of diisopropyl ether was added to the solution for precipitating a crystal. The crystal was filtered, and sufficiently washed in diisopropyl ether, and dried in vacuo.

The obtained crystal was reacted with N-(2-bromoacetyl)-N'-(3,4-dihydroxybenzoyl)hydrazine in the same manner as in Reference example 10, and the title compound in tiny red powder was obtained.

mp: 157° C. (change color).

NMR (DMSO-d6) δ (ppm): 1.40(s, 6H), 2.98–3.44(m, 2H), 3.87–4.11(m, 1H), 4.53(d, 2H, J=13Hz), 4.80(d, 2H, J=13Hz), 5.50(s, 2H), 5.26–5.80(m, 1H), 6.76(s, 1H), 7.01–7.66(m, 5H), 8.25(d, 2H, J=6Hz), 8.70(d, 2H, J=6Hz), 9.26–9.66(br, 1H), 10.13–10.50(br, 2H).

EXAMPLE 7

(6S,7S)-7-[(Z)-2-(2-aminothiazol-4-yl)-2-(3,4-dihydroxyphenylmethoxyimino)]acetamide -3-(2-methyl-1,3,4-thiadiazol-5-ylthiomethyl)isocephem-4-carboxylic acid Using benzhydryl(6S,7S)-7-[(Z)-2-(2,2-dimethylbenzodioxol-5-yl)-methoxyimino-2-(2-tritylaminothiazol-4-yl)]acetamide-3-(2-methyl-1,3,4-thiadiazol-5-ylthiomethyl)isocephem-4-carboxylate obtained in Reference example 5, the title compound in tiny red powder was obtained in the same manner as in Example 1.

mp: 153° C. (decomposed).

NMR (DMSO-d6) δ (ppm): 2.73(s, 3H), 2.76–3.33(m, 2H), 3.80–4.13(m, 1H), 4.36(d, 1H, J=12Hz), 4.61(d, 1H, J=12Hz), 4.99(s, 2H), 5.65(dd, 1H, J=5Hz, J=9Hz), 6.65(d, 1H, J=10Hz), 6.86(s, 1H), 6.87(s, 1H), 6.88(d, 1H, J=10Hz), 7.20–7.50(brs, 2H), 9.25(d, 1H, J=9Hz).

EXAMPLE 8

(6S,7S)-7-{(Z)-2-(2-aminothiazol-4-yl)-2-[carboxy(3,4-dihydroxyphenol)methoxyimino]}acetamide-3-(2-methyl-1,3,4-thiadiazol-5-ylthiomethyl)isocephem-4-carboxylic acid Using benzhydryl(6S,7S)-7-{(Z)-2-[t-butoxycarbonyl-(2,2-dimethylbenzodioxol-5-yl)][methoxyimino -2-(2-tritylaminothiazol-4-yl)}acetamide-3-(2-methyl-1,3,4-thiadiazol-5-ylthiomethyl)isocephem -4-carboxylate obtained in Reference example 6, the title compound in tiny red powder was obtained in the same manner as in Example 1.

mp: 142° C. (change color).

NMR (DMSO-d6) δ (ppm): 2.70(s, 3H), 2.75–3.29(m, 2H), 3.82–4.15(m, 1H), 4.29(d, 1H, J=14Hz), 4.65(d, 1H, J=14Hz), 5.62(dd, 1H, J=6Hz, J=9Hz), 5.75–5.83(m, 1H), 6.63(d, 1H, J=11Hz), 6.84(s, 1H), 6.87(s, 1H), 6.89(d, 1H, J=11Hz), 7.23–7.47(brS, 2H), 9.28(d, 1H, J=9Hz).

EXAMPLE 9

(6S,7S)-7-[(Z)-2-(2-aminothiazol-4-yl)-2-(1-carboxy-1-methylethoxy)imino]acetamide-3-[(5-hydroxy-4-pyridone-2-yl)methyl-4-pyridinio]thiomethylisocephem-4-carboxylate Using benzhydryl(6S,7S)-7-[(Z)-2-(2-aminothiazol-4-yl)-2-(1-t-butoxycarbonyl-1-methylethoxy)imino] acetamide-3-(pyridine-4-ylthiomethyl)isocephem-4-carboxylate and 2-iodomethyl-5-hydroxy-4-pyridone, the title compound in tiny yellow powder was obtained in the same manner as in Reference example 10.

mp: 164° C. (change color), 205° C. (decomposed).

NMR (DMSO-d6) δ (ppm): 1.45(s, 6H), 3.10–3.40(m, 2H), 3.87–4.25(m, 1H), 4.53(s, 2H), 5.65–5.80(m, 3H), 6.82(s, 1H), 7.03(s, 1H), 7.80–8.20(m, 3H), 8.77–8.92(m, 2H), 9.14(d, 1H, J=8Hz).

EXAMPLE 10

(6S,7S)-7-[(Z)-2-(2-aminothiazol-4-yl)-2-(1-carboxymethoxy)iminoacetamide]-3
{[1-[2-(3,4-dihydroxyphenyl)-2-oxo]ethyl]-4-pyridinio} thiomethyl-Δ³-O-2-isocephem -4-carboxylate Using benzhydryl(6S,7S)-7-[(Z)-2-(2-aminothiazol-4-yl)-2-(1-t-butoxycarbonylmethoxyimino) acetamide]-3-{[1-[2-(3,4-dihydroxyphenyl)-2-oxo]ethyl]-4-pyridinio} thiomethyl-Δ³-O-2-isocephem-4-carboxylate, the title compound was obtained in the same manner as in Reference example 10.

mp: 125° C. (change color).

NMR (DMSO-d6) δ (ppm): 3.40–4.30(m, 2H), 4.45(bs, 2H), 4.62(bs, 2H), 5.25(d, 1H), 5.85(dd, 1H), 6.21(bs, 2H), 6.81(s, 1H), 6.98(d, 1H), 7.43(bs, 3H), 7.48(d, 1H), 8.10(d, 2H), 8.68(d, 2H), 9.56(d, 1H), 9.40–9.70(m, 1H).

EXAMPLE 11

(6S,7S)-7-[(Z)-2-(2-aminothiazol-4-yl)-2-(1,5-dihydroxy-4-pyridone-2-ylmethoxyimino)acetamide]-3-(1-carboxymethyl-1H-tetrazole-5-ylthiomethyl)isocephem-4-carboxylic acid Using benzhydryl(6S,7S)-7-[(Z)-2-(2-tritylaminothiazol-4-yl)-2-(1,5-dibenzhydryloxy -4-pyridone-2-ylmethoxyimino)acetamide]-3-(1-benzhydryloxycarbonylmethyl-1H-tetrazole-5-ylthiomethyl) isocephem-4-carboxylate, the title compound in tiny yellow powder was obtained in the same manner as in Example 1.

mp: 119° C. (change color).

NMR (DMSO-d6) δ (ppm): 3.00–3.23(m, 2H), 3.40–3.60(m, 1H), 4.44(s, 1H), 5.22(s, 2H), 5.23(s, 2H), 5.65(dd, 1H, J=8Hz, 4Hz), 6.83(s, 1H), 6.88(s, 1H), 7.24(bs, 2H), 7.86(s, 1H), 9.41(d, 1H, J=8Hz).

EXAMPLE 12

(6S,7S)-7-[(Z)-2-(2-aminothiazol-4-yl)-2-(1,5-dihydroxy-4-pyridone-2-ylmethoxyimino)acetamide]-3-(2-amino-1,3,4-thiadiazol-5-ylthiomethyl)isocephem-4-carboxylic acid Using benzhydryl(6S,7S)-7-[(Z)-2-(2-tritylaminothiazol-4-yl)-2-(1,5-dibenzhydryloxy -4-pyridone-2-ylmethoxyimino)acetamide]-3-(2-tritylamino-1,3,4-thiadiazol-5-ylthiomethyl)isocephem -4-carboxylate, the title compound in tiny brown powder was obtained in the same manner as in Example 1.

mp: 123° c. (change color).

NMR (DMSO-d6) δ (ppm): 3.00–3.27(m, 2H), 3.40–3.70(m, 1H), 4.15(d, 1H, J=13Hz), 4.38(d, 1H, J=13Hz), 5.21(s, 2H), 5.67(dd, 1H, J=9Hz, 4Hz), 6.79(s, 1H), 6.89(s, 1H), 7.28(bs, 4H), 7.79(s, 1H), 9.46(d, 1H, J=9Hz).

EXAMPLE 13

(6S,7S)-7-[(Z)-2-(2-aminothiazol-4-yl)-2-(1,5-dihydroxy-4-pyridone-2-ylmethoxyimino)acetamide]-3-[1-(2-hydroxyethyl)-1H-tetrazole-5-ylthiomethyl]isocephem-4-carboxylic acid.

Using benzhydryl(6S,7S)-7-[(Z)-2-(2-tritylaminothiazol-4-yl)-2-(1,5-dibenzyhydryloxy -4-pyridone-2-ylmethoxyimino)acetamide]-3-[1-(2-hydroxyethyl)-1H-tetrazole-5-ylthiomethyl]isocephem-4-carboxylate, the title compound in tiny yellow powder was obtained in the same manner as in Example 1.

mp: 121° C. (change color).

NMR (DMSO-d6) δ (ppm): 3.00–3.42(m, 3H), 4.25–4.55(m, 6H), 5.18(s, 2H), 5.67(dd, 1H, J=9Hz, J=4Hz), 6.78(s, 1H), 6.88(s, 1H), 7.25(bs, 2H), 7.78(s, 1H), 9.42(d, 1H, J=9Hz).

EXAMPLE 14

(6S,7S)-7-[(Z)-2-(2-aminothiazol-4-yl)-2-(1,5-dihydroxy-4-pyridone-2-ylmethoxyimino)acetamide]-3-[(1-carboxymethyl-4-pyridinio)thiomethyl]isocephem-4-carboxylate Using benzhydryl(6S,7S)-7-[(Z)-2-(2-tritylaminothiazol-4-yl)-2-(1,5-dibenzyhydryloxy -4-pyridone-2-ylmethoxyimono)acetamide]-3-(pyridine-4-ylthiomethyl)-4-carboxylate, the title compound was obtained in the same manner as in Reference example 10.

mp: 139° C. (change color).

NMR (DMSO-d6) δ (ppm): 2.91(m, 2H), 3.84–4.11(m, 1H), 4.48(s, 2H), 4.82(s, 2H), 5.15(s, 2H), 5.38(dd, 1H, J=3Hz, J=9Hz), 6.85(s, 1H), 6.88(s, 1H), 7.30(brs, 2H), 7.65(s, 1H), 7.99(d, 2H, J=6Hz), 8.53(d, 2H, J=6Hz), 9.44(d, 1H, J=9Hz).

EXAMPLE 15

(6S,7S)-7-[(Z)-2-(2-aminothiazol-4-yl)-2-(1,5-dihydroxy-4-pyridone-2-ylmethoxyimino)acetamide]-3-[(5-carboxymethyl-4-methyl-thiazol-2-yl)thiomethyl]isocephem-4-carboxylic acid Using benzhydryl(6S,7S)-7-[(Z)-2-(2-tritylaminothiazol-4-yl)-2-(1,5-dibenzhydryloxy -4-pyridone-2-ylmethoxyimino)acetamide]-3-[(5-benzhydryloxycarbonylmethyl-4-methyl-thiazol-2-yl) thiomethyl]isocephem-4-carboxylate, the title compound was obtained in the same manner as in Example 1.

mp: 178° C. (change color).

NMR (DMSO-d6) δ (ppm): 2.23(s, 3H), 2.9–3.3(m, 2H), 3.72(s, 2H), 3.83–4.05(m, 1H), 4.17(d, 1H, J=14Hz), 4.56(d, 1H, J=14Hz), 5.17(s, 2H), 5.65(dd, 1H, J=8Hz, J=4Hz), 6.74(s, 1H), 6.83(s, 1H), 7.22(bs, 2H), 7.73(s, 1H), 9.32(d, 1H, J=8Hz).

EXAMPLE 16

(6R,7R)-7-[(Z)-2-(2-aminothiazol-4-yl)-2-(1-carboxy-1-methylethoxy)imonoacetamide
-3-[(5-hydroxy-4-pyridon-2-yl)methyl-4-pyridinio]thiomethyl-3-cephem-4-carboxylate Using p-methoxybenzyl(6R,7R)-7-[(Z)-2-(2-aminothiazol-4-yl)-2-(1-t-butoxycarbonyl-1-methylethoxy)imino]acetamide-3-(pyridine-4-ylthiomethyl)-3-cephem-4-carboxylate and 2-iodomethyl-5-hydroxy-4-pyridone, the title compound was obtained in the same manner as in Reference example 11.

mp: 128° C. (change color).

NMR (DMSO-d6) δ: 1.45(s, 6H), 3.52(ABq, 2H), 4.50(bs, 2H), 5.12(d, 1H), 5.4–5.9(m, 3H), 6.77(s, 1H), 6.93(s, 1H), 7.26(s, 2H), 7.84(s, 1H), 8.20(d, 2H), 8.77(d, 2H), 9.58(d, 1H).

EXAMPLE 17

(6R,7R)-7-[(Z)-2-(2-aminothiazol-4-yl)-2-(1-carboxy-1-methylethoxy)imino]acetamide-3-[1-(N-3,4-dihydroxybenzamide)carbamoylmethyl-4-pyridinio]thiomethyl-3-cephem-4-carboxylate Using p-methoxybenzyl(6R,7R)-7-[(Z)-2-(2-aminothiazol-4-yl)-2-(1-t-butoxycarbonyl-1-methylethoxy)imino]acetamide-3-(pyridine-4-ylthiomethyl)-3-cephem-4-carboxylate and N-bromoacetyl-N'-3,4-dihydrobenzoylhydrazide, the title compound was obtained in the same manner as in Reference example 11.

mp: 131° C. (change color).

NMR (DMSO-d6) δ: 1.1–1.7(m, 6H), 2.9–4.0(m, 2H), 4.47(bs, 2H), 5.06(d, 1H), 5.46(bs, 2H), 5.67(dd, 1H), 6.5–7.5(m, 5H), 6.70(s, 1H), 8.22(d, 2H), 8.64(d, 2H), 9.1–11.3(m, 3H).

EXAMPLE 18

(6R,7R)-7-[(Z)-2-(2-aminothiazol-4-yl)-2-(1-carboxy-1-methylethoxy)iminoacetamide]-3-[[1-[2-(3,4-dihydroxyphenyl)-2-oxo]ethyl]-4-pyridinio]thiomethyl-3-cephem-4-carboxylate Using p-methoxybenzyl(6R,7R)-7-[(Z)-2-(2-aminothiazol-4-yl)-2-(1-t-butoxycarbonyl-1-methylethoxy)imino]acetamide-3-(pyridine-4-ylthiomethyl)-3-cephem-4-carboxylate and 2-iode-3',4'-dihydroxyacetophenone, the title compound was obtained in the same manner as in Reference example 11.

mp: 127° C. (change color).

NMR (DMSO-d6) δ: 1.45(s, 6H), 4.57(bs, 2H), 5.15(d, 1H), 5.68(q, 1H), 6.14(bs, 2H), 6.74(s, 1H), 6.97(d, 1H), 7.34–7.68(m, 2H), 8.32(d, 2H), 8.60(d, 2H).

EXAMPLE 19

(6R,7R)-[(Z)-2-(2-aminothiazol-4-yl)-2-methoxyiminoacetamide]-3-[[1-[2-(3,4-dihydroxyphenyl)-2-oxo]ethyl]-4-pyridinio]thiomethyl-3-cephem-4-carboxylate Using p-methoxybenzyl(6R,7R)-7-[(Z)-2-(2-aminothiazol-4-yl)-2-methoxyiminoacetamide]-3-(pyridine-4-ylthiomethyl)-3-cephem-4-carboxylate and 2-iode-3',4'-dihydroxyacetophenone, the title compound was obtained in the same manner as in Reference 11.

mp: 119° C. (change color).

NMR (DMSO-d6) δ: 3.0–4.0(m, 2H), 3.83(s, 3H), 4.3–4.6(bs, 2H), 5.18(d, 1H), 5.76(dd, 1H), 6.21(bs, 2H), 6.7–7.1(m, 2H), 7.16(bs, 2H), 7.3–7.6(m, 2H), 8.10(d, 2H), 8.62(d, 2H), 9.55(d, 1H).

EXAMPLE 20

(6S,7S)-7-[(Z)-2-(5-amino-1,2,4-thiadiazol-3-yl)-2-(1,5-dihydroxy-4-pyridone-2-ylmethoxyimino)acetamide]-3-(5-carboxymethyl-4-methylthiazol-2-ylthiomethyl)isocephem-4-carboxylic acid To 0.87 g of benzhydryl(6S,7S)-7-[(Z)-2-(5-amino-1,2,4-thiadiazol-3-yl)-2-(1,5 -dibenzhydryloxy-4-pyridone-2-ylmethoxyimino)acetamide]-3-(5-benzhydryloxycarbonylmethyl-4-methylthiazol-2-ylthiomethyl)isocephem-4-carboxylate obtained in Reference 13, 0.5 ml of anisol and 4.5 ml of trifluoroacetic acid were added, and the mixture was stirred for 2 hours at room temperature.

To this reaction solution, 50 ml of diethyl ether was added, and the produced powder solid was filtered and suspended in 20 ml of water. By adding a proper amount of 7% sodium hydrogencarbonate aqueous solution to adjust the pH to 3, the powder solid matter in liquid was filtered, washed in water, and 0.2 g of the title compound in tiny yellow powder was obtained.

mp: 116° C. (change color).

NMR (DMSO-d6) δ](ppm): 2.22(3H, s), 2.9–3.3(2H, m), 3.73(2H, s), 3.85–4.10(1H, m), 4.35(2H, q), 5.23(2H, s), 5.60(1H, dd), 6.69(1H, s), 7.72(1H, s), 8.14(2H, bs), 9.38(1H, d).

EXAMPLE 21

(6R,7R)-7-[(Z)-2-(5-amino-1,2,4-thiadiazol-3-yl)-2-(1,5-dihydroxy-4-pyridone -2-ylmethoxyimino)acetamide]-3-(5-carboxymethyl-4-methylthiazol-2-ylthiomethyl)-3-cephem-4-carboxylic acid Using benzhydryl(6R,7R)-7-[(Z)-2-(5-amino-1,2,4-thiadiazol-3-yl)-2-(1,5-dibenzhydryloxy-4-pyridone-2-ylmethoxyimino)acetamide]-3-(5-benzhydryloxycarbonylmethyl-4-methylthiazol -2-ylthiomethyl)-3-cephem-4-carboxylate obtained in Reference example 14, the title compound in tiny red powder was obtained in the same manner as in Example 20.

m: 101° C. (change color).

NMR (DMSO-d6) δ(ppm): 2.22(3H, s), 3.2 to 5.9(6H, m), 3.72(2H, s), 5.22(2H, s), 6.72(1H, s), 7.74(1H, s), 8.11(2H, bs), 9.61(1H, d).

EXAMPLE 22

(6S,7S)-7-[(Z)-2-(5-amino-1,2,4-thiadiazol-3-yl)-2-(1,5-dihydroxy-4-pyridone-2-ylmethoxyimino)acetamide]-3-(1-carboxymethyl-1H-tetrazol-5-ylthiomethyl)-isocephem-4-carboxylic acid Using benzhydryl(6S,6S)-7-[(Z)-2-(5-amino-1,2,4--thiadiazol-3-yl)-2-(1,5-dibenzhydryloxy-4-pyridone-2-ylmethoxyimino)acetamide]-3-(1-benzhydryloxycarbonylmethyl-1H-tetrazol-5-ylthiomethyl)-isocephem-4-carboxylate obtained in Reference example 15, the title compound in tiny yellow powder was obtained in the same manner as in Example 20.

mp: 108° C. (change color).

NMR (DMSO-d6) δ(ppm): 3.01 to 3.21(2H, m), 3.80 to 4.12(1H, m), 4.38(2H, s), 5.21(2H, s), 5.22(2H, s), 5.66(1H, dd), 6.71(1H, s), 7.75(1H, s), 8.12(2H, bs), 9.40(1H, d).

EXAMPLE 23

(6R,7R)-7-[(Z)-2-(5-amino-1,2,4-thiadiazol-3-yl)-2-(1,5-dihydroxy-4-pyridone-2-ylmethoxyimino)acetamide]-3-(1-carboxymethyl-1H-tetrazole-5-ylthiomethyl)-3-cephem-4-carboxylic acid Using paramethoxybenzyl(6R,7R)-7-[(Z)-2-(5-amino-1,2,4-thiadiazol-3-yl)-2-(1,5-dibenzhydryloxy-4-pyridone-2-ylmethoxyimino)acetamide]-3-(1-benzyhydryloxycarbonylmethyl-1H-tetrazol-5-ylthiomethyl)-3-cephem-4-carboxylate obtained in Reference example 16, the title compound in tiny yellow was obtained in the same manner as in Example 20.

mp: 118° C. (change color).

NMR (DMSO-d6) δ(ppm): 3.48(2H, ABq), 4.31(2H, bs), 5.09(1H, d), 5.22(2H, s), 5.23(2H, s), 5.78(1H, dd), 6.80(1H, s), 7.80(1H, s), 8.12(2H, bs), 9.63(1H, d).

EXAMPLE 24

(6S,7S)-7-[(Z)-2-(5-amino-1,2,4-thiadiazol-3-yl)-2-(1,5-dihydroxy-4-pyridone-2-ylmethoxyimino) acetamide]-3-(4-carboxy-3-hydroxyisothiazol-5-ylthiomethyl) isocephem-4-carboxylic acid Using benzhydryl(6S,7S)-7-[(Z)-2-(5-amino-1,2,4-thiadiazol-3-yl)-2-(1,5-dibenzhydryloxy-4-pyridone-2-ylmethoxyimino)acetamide]-3-(4-carboxy-3-(4-carboxy-3-hydroxyisothiazol-5-ylthiomethyl)isocephem-4-carboxylate obtained in Reference example 17, the title compound in tiny yellow powder was obtained in the same manner as in Example 20.

mp: 112° C. (change color).

NMR (DMSO-d6) δ(ppm): 3.05–3.31(2H, m), 3.35–3.52(1H, m), 4.39(2H, s), 5.20(2H, s), 5.59(1H, dd), 6.69(1H, s), 7.72(1H, s), 8.14(2H, bs), 9.41(1H, d).

EXAMPLE 25

(6R,7R)-7-[(Z)-2-(5-amino-1,2,4-thiadiazol-3-yl)-2-(1,5-dihydroxy-4-pyridone-2-ylmethoxyimino)acetamide]-3-(4-carboxy-3-hydroxyiso-thiazol-5-ylthiomethyl)-3-cephem-4-carboxylic acid Using parametoxybenzyl(6R,7R)-7-[(Z)-2-(5-amino--1,2,4-thiadiazol-3-yl)-2-(1,5-dibenzhydryloxy-4-pyridone-2-ylmethoxyimino)acetamide[-3-(4-carboxy-3-hydroxyisothiazol-5-ylthiomethyl)-3-cephem-4-carboxylate obtained in Reference example 18, the title compound in tiny yellow powder was obtained in the same manner as in Example 20.

mp: 111° C. (change color).

NMR (DMSO-d6) δ(ppm): 3.41(2H, ABq), 4.29(2H, bs), 5.12(1H, d), 5.21(2H, s), 5.72(1H, dd), 6.82(1H, s), 7.83(1H, s), 8.14(2H, bs), 9.66(1H, d).

EXAMPLE 26

(6S,7S)-7-[(Z)-2-(5-amino-1,2,4-thiadiazol-3-yl)-2-(1,5-dihydroxy-4-pyridone-2-ylmethoxyimino) acetamide]-3-(1-carboxymethylpyridinium-4-ylthiomethyl)isocephem-4-carboxylate Using benzhydryl(6S,7S)-7-phthalimide-3-(pyrido-4-ylthiomethyl)isocephem-4-carboxylate, benzhydryl(6S,7S)-7-[(Z)-2-(5-amino-1,2,4-thiadiazol-3-yl)-2-(1,5-dibenzhydryloxy-4-pyridone-2-ylmethoxyimino) acetamide]-3-(pyrido-4-ylthiomethyl)isocephem-4-carboxylate was obtained in the same manner as in Reference example 13.

1.08 g of this compound was dissolved in 20 ml of methylene chloride, and 0.39 g of tert-butyl bromoacetate was added. The solution was stirred at room temperature for 24 hours. To this reaction solution, 50 ml of ether was added, and a brown powder was obtained. This powder was filtered, washed in ether, and 1 ml of anisol and 5 ml of trifluoroacetic acid was added, and the mixture was stirred at room temperature for 2 hours. In succession, 50 ml of ether was added to this reaction solution, and powder solid matter was obtained. This powder solid matter was filtered and washed in ether. It was then dissolved in 5% sodium hydrogencarbonate aqueous solution, and 100 ml of nonionic adsorbent resin (HP-20) was added and the pH was adjusted to 2 with 10% HCl aqueous solution to adsorb. A column was filled up with this nonionic adsorbent resin, 500 ml of water was passed, and it was eluted in 5 to 20% isopropyl alcohol aqueous solution. The desired fraction was concentrated, and the concentrate was freeze-dried, and 0.26 g of the title compound in tiny yellow powder was obtained.

mp: 128° C. (change color).

NMR (DMSO-d6) δ(ppm): 2.89 to 3.35(2H, m), 3.72–4.01(1H, m), 4.46(2H, s), 4.79(2H, s), 5.16(2H, s), 5.41(1H, dd, J=3Hz, J=9Hz), 6.83(1H, s), 7.68(1H, s), 7.88(2H, d, J=6Hz), 8.11(2H, bs), 8.51(2H, d, J=6Hz), 9.46(1H, d, J=9Hz).

EXAMPLE 27

(6R,7R)-7-[(Z)-2-(5-amino-1,2,4-thiadiazol-3-yl)-2-(1,5-dihydroxy-4-pyridone-2-ylmethoxyimino) acetamide]-3-(1-carboxymethylpyridinium-4-ylthiomethyl)-3-cephem-4-carboxylate Using parametoxybenzyl(6R,7R)-7-amino-3-(pyrido-4-ylthiomethyl)-3-cephem-4-carboxylate, parametoxybenzyl(6R,7R)-7-[(Z)-2-(5-amino-1,2,4-thiadiazol-3-yl)-2-(1,5-benzhydryloxy-4-pyridone-2-ylmethoxyimino)acetamide]-3-(pyrido-4-ylthiomethyl)-3-cephem-4-carboxylate was obtained in the same manner as in Reference example 16.

This compound was caused to react with tert-butyl bromoacetate in the same manner as in Example 26, and was treated with trifluoroacetic acid and refined, and the title compound in tiny yellow powder was obtained.

mp: 131° C. (change color).

NMR (DMSO-d6) δ(ppm): 3.05(2H, ABq), 4.62(2H, bs), 4.86(2H, s), 5.04(1H, d), 5.18(2H, s), 5.55(1H, dd), 6.78(1H, s), 7.78(1H, s), 8.01(2H, d), 8.12(2H, bs), 8.52(2H, d), 9.43(1H, d).

Pharmaceutical examples are shown below.

| Pharmaceutical example 1 | |
|---|---|
| (6S,7S)-7-[(Z)-2-(2-Aminothiazol-4-yl)-2-(1,5-dihydroxy-4-pyridone-2-ylmethoxyimino)acetamide]-3-(2-methyl-1,3,4-thiadiazol-5-yl) thiomethyl-isocephem-4-carboxylic acid | 200 mg |
| Glucose | 250 mg |
| Distilled water for injection | proper |
| Whole amount | 5 ml |

To the distilled water for injection, (6S,7S)-7-[(Z)-2-(2-Aminothiazol-4-yl)-2-(1,5-dihydroxy-4-pyridone-2-ylmethoxyimino)acetamide]-3-(2-methyl-1,3,4-thiadiazol-5-yl)thiomethyl-isocephem-4-carboxylic acid (Example 1) and glucose were dissolved, and the mixture was poured into 5 ml ampule, and after nitrogen replacement, it was sterilized under pressure for 15 minutes at 121° C., and the injection of the above composition was obtained.

| Pharmaceutical example 2 | |
|---|---|
| (6S,7S)-7-[(Z)-2-(2-Aminothiazol-4-yl)-2-(1,5-dihydroxy-4-pyridone-2-ylmethoxy-iminoacetamide]-3-(1,3,4-thiadiazol-5-yl)-thiomethylisocephem-4-carboxylic acid | 100 g |
| Abicell (tradename, Asahi Chemical) | 40 g |
| Corn starch | 30 g |
| Magnesium stearate | 2 g |
| TC-5 (tradename, Shin Etsu Chemical; hydroxypropylmethylcellulose) | 10 g |
| Polyethyleneglycol-6000 | 3 g |

| Pharmaceutical example 2 | |
| --- | --- |
| Castor oil | 40 g |
| Ethanol | 40 g |
| Whole amount | 255 g |

(6S,7S)-7-[(Z)-2-(2-Aminothiazol-4-yl)-2-(1,5-dihydroxy-4-pyridone-2-ylmethoxyimino)acetamide]-3-(1,3,4-thiadiazol-5-yl)thiomethyl-isocephem-4-carboxylic acid (Example 2), Abicell, corn starch and magnesium stearate were mixed and polished, and tableted with a pestle for sugar-coated R 100 mm tablets. The obtained tablets were coated with film coating agent composed of TC-5, polyethyleneglycol-6000, castor oil nd ethanol, and film coated tablets in the above composition were manufactured.

| Pharmaceutical example 3 | |
| --- | --- |
| (6S,7S)-7-[(Z)-2-(2-aminothiazol-4-yl)-2-(1 5-dihydroxy-4-pyridone-2-ylmethoxyimino)acetamide]-3-methylisocephem-4-carboxylate sodium salt | 2 g |
| Refined lanolin | 5 g |
| Bleached beeswax | 5 g |
| White vaseline | 88 g |
| Whole amount | 100 g |

Bleached beeswax was heated to be liquefied, and (6S,7S)-7-[(Z)-2-(2-aminothiazol-4-yl)-2-(1,5-dihydroxy-4-pyridone-2-ylmethoxyimino)acetamide]-3-methylisocephem-4-carboxylate sodium salt (Example 3), refined lanolin and while vaseline were added, and heated until liquefied, and stir red until beginning to be solidified, and the ointment in above composition was obtained.

| Pharmaceutical example 4 | |
| --- | --- |
| (6R,7R)-7-[(Z)-2-(2-aminothiazol-4-yl)-2-(1-carboxy-1-methylethoxy)imonoacetamide-3-[(5-hydroxy-4-pyridon-2-yl)methyl-4-pyridinio]thiomethyl 3-cephem-4-carboxylate | 200 mg |
| Glucose | 250 mg |
| Distilled water for injection | proper |
| Whole amount | 5 ml |

Using (6R,7R)-7-[(Z)-2-(2-aminothiazol-4-yl)-2-(1-carboxy-1-methylethoxy)imonoacetamide-3-[(5-hydroxy-4-pyridon-2-yl)methyl-4-pyridinio[thiomethyl-3-cephem-4-carboxylate (Example 16), the injection of the above composition was obtained in the same manner as in Pharmaceutical example 1.

| Pharmaceutical example 5 | |
| --- | --- |
| (6R,7R)-7-[(Z)-2-(2-aminothiazol-4-yl)-2-(1-carboxy-methylethoxy)imino]acetamide-3-[1-(N-3,4-dihydroxybenzamide) carbamoylmethyl-4-pyridinio]thiomethyl-3-cephem-4-carboxylate | 100 g |
| Abicell (tradename, Asahi Chemical) | 40 g |
| Corn starch | 30 g |
| Magnesium stearate | 2 g |
| TC-5 (tradename, Shin Etsu Chemical; hydroxypropylmethylcellulose) | 10 g |
| Polyethyleneglycol-6000 | 3 g |
| Castor oil | 40 g |
| Ethanol | 40 g |
| Whole amount | 225 g |

(6R,7R)-7-[(Z)-2-(2-aminothiazol-4-yl)-2-(1-carboxymethylethoxy)imino]acetamide-3-[1-(N-3,4-dihydroxybenzamide) carbamoylmethyl-4-pyridino]thiomethyl-3-cephem-4-carboxylate (Example 17), Abicell, corn starch and magnesium stearate were mixed and polished, and tableted with a pestle for sugar-coated R 10 mm tablets, and film coated tablet in the above composition were manufactured in the same manner as in Pharmaceutical example 2.

| Pharmaceutical example 6 | |
| --- | --- |
| (6R,7R)-7-[(Z)-2-(2-aminothiazol-4-yl)-2-(1-carboxy-1-methylethoxy)iminoacetamide]-3-[[1-[2-(3,4-dihydroxyphenyl)-2-oxo]ethyl]-4-pyridinio]thiomethyl-3-cephem-4-carboxylate | 2 g |
| Refined lanolin | 5 g |
| Bleached beeswax | 5 g |
| White vaseline | 88 g |
| Whole amount | 100 g |

(6R,7R)-7-[(Z)-2-(2-aminothiazol-4-yl)-2-(1-carboxy-1-methylethoxy)iminoacetamide]-3-[[1-[2-(3,4-dihydroxyphenyl)-2-oxo]ethyl]-4-pyridinio]thiomethyl-3-cephem-4-carboxylate (Example 18), the ointment in the above composition was obtained in the same manner as in Pharmaceutical example 3.

| Pharmaceutical example 7 | |
| --- | --- |
| (6S,7S)-7-[(Z)-2-(5-amino-1,2,4-thiadiazol-3-yl)-2-(1,5-dihydroxy-4-pyridone-2-ylmethoxyimino)acetamide]-3-(5-carboxymethyl-4-methylthiazol-2-ylthiomethyl)-isocephem-4-carboxylic acid | 200 mg |
| Glucose | 250 mg |
| Distilled water for injection | proper |
| Whole amount | 5 ml |

(6S,7S)-7-[(Z)-2-(5-amino-1,2,4-thiadiazol-3-yl)-2-(1,5-dihydroxy-4-pyridone-2-ylmethoxyimino)acetamide]-3-(5-carboxymethyl-4-methylthiazol-2-ylthiomethyl)isocephem-4-carboxylic acid (Example 20), the injection of the above composition was obtained in the same manner as in Pharmaceutical example 1.

| Pharmaceutical example 8 | |
| --- | --- |
| (6R,7R)-7-[(Z)-2-(5-amino-1,2,4-thiadiazol- 3-yl)-2-(1,5-dihydroxy-4-pyridone-2-ylmethoxyimino)acetamide]-3-(5-carboxymethyl-4-methylthiazol-2-ylthiomethyl)-3-cephem-4-carboxylic acid | 100 g |
| Abicell (tradename, Asahi Chemical) | 40 g |
| Corn starch | 30 g |
| Magnesium stearate | 2 g |
| TC-5 (tradename, Shin Etsu Chemical; hydroxypropylmethylcellulose) | 10 g |
| Polyethyleneglycol-6000 | 3 g |
| Castor oil | 40 g |
| Ethanol | 40 g |
| Whole amount | 255 g |

(6R,7R)-7-[(Z)-2-(5-amino-1,2,4-thiadiazol-3-yl)-2-(1,5-dihydroxy-4-pyridone-2-ylmethoxyimino) acetamide]-3-(5-carboxymethyl-4-methylthiazol-2-ylthiomethyl)-3-cephem- 4-carboxylic acid (Example 21), the film coated tablets in the above composition was manufactured in the same manner as in Pharmaceutical example 2.

| Pharmaceutical example 9 | |
| --- | --- |
| (6S,7S)-7-[(Z)-2-(5-amino-1,2,4-thiazol-3-yl)-2-(1,5-dihydroxy-4-pyridone-2-ylmethoxyimino) acetamide]-3-(1-carboxymethyl-1H-tetrazol-5-ylthiomethyl)-isocephem-4-carboxylic acid | 2 g |
| Refined lanolin | 5 g |
| Bleached beeswax | 5 g |
| White vaseline | 88 g |
| Whole amount | 100 g |

The bleached beeswax was heated to be liquefied, and using (6S,7S)-7-[(Z)-2-(5-amino-1,2,4-thiazol-3-yl)-2-(1,5-dihydroxy-4-pyridone-2-ylmethoxyimino)acetamide]-3-(1-carboxymethyl-1H-tetrazol-5-ylthiomethyl)isocephem-4-carboxylic acid (Example 22), the ointment in the above composition was obtained in the same manner as in Pharmaceutical example 3.

Antimicrobial Activity Test

In order to to investigate the in vitro activity of the test compounds against various bacteria, the minimal inhibitory concentration (MIC) values were determined by the plate diluted method (See CHEMOTHERAPY, 22, 1126-1128, 1974.)

The test inoculum results are shown in Table 4.

Each strain was adjusted to $1 \times 10^6$ cells/ml (O.D. 600 m$\mu$, 0.07 to 0.16).

TEST COMPOUNDS

No. 1:(6S,7S)-7-[(Z)-2-(2-Aminothiazol-4-yl)-2-(1,5-dihydroxy-4-pyridone-2-ylmethoxyimino)acetoamide]-3-(2-methyl-1,3,4-thiaziazol-5-yl)thiomethylisocephem-4-carboxylic acid (Example 1).

No. 2:(6S,7S)-7-[(Z)-2-(2-Aminothiazol-4-yl)-2-(1,5-dihydroxy-4-pyridone-2-ylmethoxyimino)acetamide]-3-(1,3,4-thiadiazol-5-yl)thiomethyl-isocephem-4-carboxylic acid (Example 2)

No. 3:(6S,7S)-7-[(Z)-2-(2-aminothiazol-4-yl)-2-(1-carboxy-1-methylethoxy)iminoacetamide]-3-{[1-[2-(3,4-dihydroxyphenyl)-2-oxo]methyl]-4-pyridinio) thiomethylisocephem-4-carboxylate (Example 5)

No. 4:(6S,7S)-7-[(Z)-2-(2-aminothiazol-4-yl)-2-(1-carboxy-1-methylethoxy)imino]acetamide-3-[1-(N-3,4-dihydroxybenzamide)carbamoylmethyl-4pyridinio]-thiomethylisocephem-4-carboxylate (Example 6)

No. 5:(6S,7S)-7-[(Z)-2-(2-aminothiazol-4-yl)-2-(3,4-dihydroxyphenylmethoxyimino)]acetamide-3-(2-methyl-1,3,4-thiadiazol-5-ylthiomethyl)isocephem-4-carboxylic acid (Example 7)

No. 6:(6S,7S)-7-{(Z)-2-(2-aminothiazol-4-yl)-2-[carboxy-(3,4-dihydroxyphenol)methoxyimino]}acetamide-3-(2-methyl-1,2,3-thiadiazol-5-ylthiomethyl)isocephem-4-carboxylic acid (Example 8)

No. 7:(6S,7S)-7-[(Z)-2-(2-aminothiazol-4-yl)-2-(1-carboxy-1-methylethoxy)imino]acetamide-3[(5-hydroxy-4-pyridone-2-yl)methyl-4-pyridinio]thiomethylisocephem-4-carboxylate (Example 9)

No. 8:(6S,7S)-7-[(Z)-2-(2-aminothiazol-4-yl)-2-(1--carboxymethoxy)iminocetamide]-3{[1-[2-(3,4-dihydroxyphenyl)-2-oxo]ethyl]-4-pyridinio{-thiomethyl-$\Delta^3$-O2-isocephem-4-carboxylate (Example 10)

No. 9:(6S,7S)-7-[(Z)-2-(2-aminothiazol-4-yl)-2-(1,5-dihydroxy-4-pyridine-2-ylmethoxyimino)acetamide]-3-(1-carboxymethyl-1H-tetrazole-5-ylthiomethyl-)isocephem-4-carboxylic acid (Example 11)

No. 10:(6S,7S)-7-[(Z)-2-(2-aminothiazol-4-yl)-2-(1,5-dihydroxy-4-pyridone-2-ylmethoxyimino)acetamide]-3-(2-amino-1,3,4-thiadiazol-5-ylthiomethyl)isocephem-4-carboxylic acid (Example 12)

No. 11:(6S,7S)-7-[(Z)-2-(2-aminothiazol-4-yl)-2-(1,5-dihydroxy-4-pyridone-2-ylmethoxyimino)acetamide]-3-[1-(2-hydroxyethyl)-1H-tetrazole-5-ylthiomethyl] isocephem-4-carboxylic acid (Example 13)

No. 12:(6S,7S)-7-[(Z)-2-(2-aminothiazol-4-yl)-2-(1,5-dihydroxy-4-pyridone-2-ylmethoxyimino)acetamide]-3-[(1-carboxymethyl-4-pyridinio)-thiomethyl]isocephem-4-carboxylate (Example 14)

No. 13:(6S,7S)-7-[(Z)-2-(2-aminothiazol-4-yl)-2-(1,5-dihydroxy-4-pyridone-2-ylmethoxyimino)acetamide]-3-[(5-carboxymethyl-4-methyl-thiazol-2-yl)thiomethyl]isocephem-4-carboxylic acid (Example 15)

No. 14: (6R,7R)-7-[(Z)-2-(2-aminothiazol-4-yl)-2-(1-carboxy-1-methylethoxy)iminoacetamide-3-[(5-hydroxy-4-pyridon-2-yl)methyl-4-pyridinio]thiomethyl-3-cephem-4-carboxylate (Example 16)

No. 15:(6R,7R)-7-[(Z)-2-(2-aminothiazol-4-yl)-2-(1-carboxy-methylethoxy)imino]acetamide-3-[1-(N-3,4-dihydroxybenzamide)carbamoylmethyl-4-pyridinio]-thiomethyl-3-cephem-4-carboxylate (Example 17)

No. 16:(6R,7R)-7-[(Z)-2-(2-aminothiazol-4-yl)-2-(1-carboxy-1-methylethoxy)iminoacetamide]-3-[[1-[2-(3,4-dihydroxyphenyl)-2-oxo]ethyl]-4-pyridinio]thiomethyl-3-cephem-4-carboxylate (Example 18)

No. 17:(6R,7R)-7-[(Z)-2-(2-aminothiazol-4-yl)2-methoxyiminoacetamide]-3-[[1-[2-(3,4-dihydroxphenyl)-2-oxo]ethyl]-4-pyridino]-thiomethyl-3-cephem-4-carboxylate (Example 19)

No. 18:(6S,7S)-7-[(Z)-2-(5-amino-1,2,4-thiazol-3-yl)-2-(1,5-dihydroxy-4-pyridone-2-ylmethoxyimino)acetamide]-3-(5-carboxymethyl-4-methylthiazol-2-ylthiomethyl)-isocephem-4-carboxylic acid (Example 20)

No. 19:(6R,7R)-7-[(Z)-2-(5-amino-1,2,4-thiadiazol-3-yl)-2-(1,5-dihydroxy-4-pyridone-2-ylmethoxyimino)acetamide]-3-(5-carboxymethyl-4-methylthiazol-2-ylthiomethyl)-3-cephem-4-carboxylic acid (Example 21)

No. 20:(6S,7S)-7-[(Z)-2-(5-amino-1,2,4-thiaziazol-3-yl)-2-(1,5-dihydroxy-4-pyridone-2-ylmethoxyimino)acetamide]-3-(1-carboxymethyl-1H-tetrazol-5-ylthiomethyl)-isocephem-4-carboxylic acid (Example 22)

No. 21:(6R,7R)-7-[(Z)-2-(5-amino-1,2,4-thiadiazol-3-yl)-2(1,5-dihydroxy-4-pyridone-2-ylmethoxyimino)acetamide]-3-(1-carboxymethyl-1H-tetrazol-5-ylthiomethyl)-3-cephem-4-carboxylic acid (Example 23)

No. 22:(6S,7S)-7-[(Z)-2-(5-amino-1,2,4-thiadiazol-3-yl)-2-(1,5-dihydroxy-4-pyridone-2-ylmethoxyimino)acetamide]-3-(4-carboxy-3-hydroxyisothiazol-5-ylthiomethyl)isocephem-4-carboxylic acid (Example 24)

No. 23:(6R,7R)-7-[(Z)-2-(5-amino-1,2,4-thiadiazol-3-yl)-2-(1,5-dihydroxy-4-pyridone-2-ylmethoxyimino)acetamide]3-(4-carboxy-3-hydroxyisothiazol-5-ylthiomethyl)-3-cephem-4-carboxylic acid (Example 25)

No. 24:(6S,7S)-7-[(Z)-2-(5-amino-1,2,4-thiadiazol-3-yl)-2-(1,5-dihydroxy-4-pyridone-2-ylmethoxyimino)acetamide]-3-(1-carboxymethylpyridinium-4-ylthiomethyl)-isocephem-4-carboxylate (Example 26)

No. 25:(6R,7R)-7-[(Z)-2-(5-amino-1,2,4-thiadiazol-3-yl)-2-(1,5-dihydroxy-4-pyridone-2-ylmethoxyimino)acetamide]-3-(1-carboxymethylpyridinium-4-ylthiomethyl)-3-cephem-4-carboxylate (Example 27)

Comparison: Ceftazizime (CAZ, cephem antibiotic)

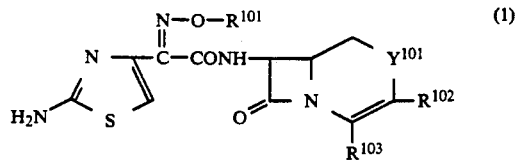

(1)

wherein $R^{101}$ is a lower alkyl group, a carboxy-lower-alkyl group or a group:

$$-A^{101}-R^{104}$$

wherein $A^{101}$ is a lower alkylene group which may have a carboxy group and $R^{104}$ is a group:

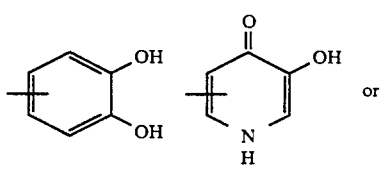

or

TABLE 4

| strain | No. 1 | No. 2 | No. 3 | No. 4 | No. 5 | No. 6 | No. 7 | No. 8 | No. 9 | No. 10 | No. 11 | No. 12 | No. 13 |
|---|---|---|---|---|---|---|---|---|---|---|---|---|---|
| S. aureus FDA-209P | 25 | 12.5 | 0.78 | 3.13 | 1.56 | 3.13 | 3.13 | 1.56 | 100 | 50 | 50 | 12.5 | 100 |
| E. coli No. 29 | 0.024 | 0.024 | ≦0.006 | 0.012 | 0.012 | 0.012 | 0.012 | ≦0.006 | 0.012 | 0.05 | 0.05 | 0.012 | 0.012 |
| K. pneumoniae NCTA-9632 | 0.012 | ≦0.006 | ≦0.006 | ≦0.006 | 0.012 | ≦0.006 | 0.012 | ≦0.006 | ≦0.006 | 0.05 | 0.012 | ≦0.006 | ≦0.006 |
| M. moganii IIDkono | 0.05 | 0.1 | 0.024 | 0.024 | 0.05 | 0.024 | 0.024 | 0.024 | 0.024 | 0.05 | 0.024 | 0.1 | 0.024 |
| S. marcescens IFO 12648 | 0.024 | 0.05 | 0.024 | 0.024 | 0.05 | 0.012 | 0.012 | 0.024 | 0.012 | 0.05 | 0.012 | 0.05 | 0.012 |
| A. calcoaceticus Ac-54 | 0.1 | 0.1 | 0.1 | 0.2 | 0.39 | 0.2 | 0.2 | 0.05 | 0.012 | 0.78 | 0.2 | 0.39 | 0.012 |
| P. aeruginosa ATCC-10145 | 0.1 | 0.05 | 0.05 | 0.1 | 0.39 | 0.2 | 0.1 | 0.05 | 0.05 | 0.1 | 0.05 | 0.1 | 0.05 |
| P. aeruginosa E-2 | 0.2 | 0.05 | 0.05 | 0.1 | 0.39 | 0.39 | 0.1 | 0.1 | 0.05 | 0.2 | 0.05 | 0.2 | 0.05 |

| strain | No. 14 | No. 15 | No. 16 | No. 17 | No. 18 | No. 19 | No. 20 | No. 21 | No. 22 | No. 23 | No. 24 | No. 25 | Comparative Example (CAZ) |
|---|---|---|---|---|---|---|---|---|---|---|---|---|---|
| S. aureus FDA-209P | 6.25 | 3.13 | 1.56 | 0.39 | 100 | 100 | 100 | 100 | 100 | 100 | 12.5 | 6.25 | 3.13 |
| E. coli No. 29 | 0.05 | 0.012 | 0.012 | 0.012 | | | | | | | | | |
| E. coli NIHJ JC-2 | | | | | 0.1 | 0.1 | 0.05 | 0.1 | 0.05 | 0.1 | 0.1 | 0.2 | 0.2 |
| K. pneumoniae NCTC-9632 | 0.012 | 0.012 | 0.012 | 0.012 | 0.024 | 0.024 | 0.012 | 0.012 | 0.012 | 0.024 | 0.024 | 0.024 | 0.05 |
| M. moganii IIDkono | 0.05 | 0.05 | 0.05 | 0.1 | 0.05 | 0.05 | 0.024 | 0.024 | 0.05 | 0.05 | 0.024 | 0.05 | 0.05 |
| S. marcescens IFO 12648 | 0.024 | 0.05 | 0.024 | 0.05 | 0.024 | 0.024 | 0.012 | 0.012 | 0.012 | 0.024 | 0.024 | 0.024 | 0.024 |
| A. calcoaceticus Ac-54 | 0.39 | 0.1 | 0.05 | 0.1 | 0.1 | 0.05 | 0.05 | 0.05 | 0.1 | 0.1 | 0.39 | 0.39 | 1.56 |
| P. aeruginosa ATCC-10145 | 0.2 | 0.05 | 0.1 | 0.2 | 0.1 | 0.05 | 0.05 | 0.1 | 0.1 | 0.1 | 0.1 | 0.1 | 0.78 |
| P. aeruginosa E-2 | 0.1 | 0.05 | 0.1 | 0.39 | 0.1 | 0.1 | 0.05 | 0.1 | 0.2 | 0.1 | 0.2 | 0.2 | 1.56 |

What is claimed is:

1. A cephalosporin derivative represented by the general formula (1):

-continued

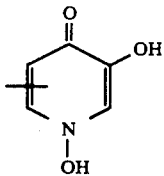

$R^{102}$ is a hydrogen atom, a lower alkyl group or a heterocylic thiomethyl group having 1 to 4 hetero atoms selected from the group consisting of a nitrogen atom and a sulfur atom, and the hetero cyclic moiety of the heterocyclic thiomethyl group may have a lower alkyl group, a carboxy lower alkyl group, a hydroxy lower alkyl group, an amino group or a group:

$-A^{102}-(B^{101})_n-R^{104}$ wherein $A^{102}$ is a lower alkylene group, $B^{101}$ is a carbonyl group or a group:

—CONHNHCO— n is 0 or 1, and $R^{104}$ is the same as defined above; $R^{103}$ is a carboxy group or a carboxylate group, and $Y^{101}$ is an oxygen atom or a sulfur atom, provided that at least one of $R^{101}$ and $R^{102}$ contains $R^{104}$, or a pharmaceutically acceptable salt thereof.

2. A cephalosporin derivative or its pharmaceutically acceptable salt thereof as claimed in claim 1, wherein $Y^{101}$ is a sulfur atom, $R^{101}$ is a $C_1$–$C_6$ alkyl group, a carboxy $C_1$–$C_6$ alkyl group or a group:

wherein $A^{101}$ is a $C_1$–$C_6$ alkylene group which may have a carboxy group and $R^{104}$ is a group:

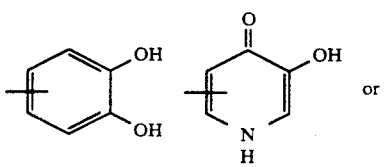

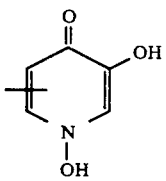

$R^{102}$ is a hydrogen atom, a $C_1$–$C_4$ alkyl group, or a heterocyclic thiomethyl group having 1 to 4 hetero atoms selected from the group consisting of a nitrogen atom and a sulfur atom, and the hetero cyclic moiety of the heterocyclic thiomethyl group may have a $C_1$–$C_6$ alkyl group, a carboxy $C_1$–$C_6$ alkyl group, a hydroxy $C_1$–$C_6$ alkyl group, an amino group, or a group:

$-A^{102}-(C^{101})_n-R^{104}$ wherein $A^{102}$ is a $C_1$–$C_6$ alkylene group, $B^{101}$ is a carbonyl group or a group:

—CONHNHCO— n is 0 or 1, and $R^{104}$ is same as defined above; and $R^{103}$ is a carboxy group or carboxylate group provided that at least one of $R^{101}$ and $R^{102}$ contains $R^{104}$.

3. A cephalosporin derivative or the pharmaceutically acceptable salt thereof as claimed in claim 1, wherein $Y^{101}$ is an oxygen atom, $R^{101}$ is a $C_1$–$C_6$ alkyl group, a carboxy $C_1$–$C_6$ alkyl group or a group:

$-A^{101}-R^{104}$ wherein $A^{101}$ is a $C_1$–$C_6$ alkylene group which may have a carboxy group and $R^{104}$ is a group:

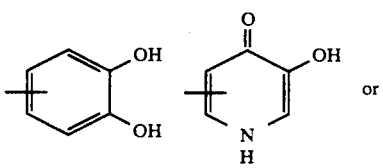

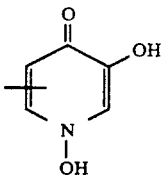

$R^{102}$ is a hydrogen atom, a $C_1$–$C_6$ alkyl group, or a heterocyclic thiomethyl group having 1 to 4 hetero atoms selected from the group consisting of a nitrogen atom and a sulfur atom, and the heterocyclic moiety of the heterocyclic thiomethyl group may have a $C_1$–$C_6$ alkyl group, a carboxy $C_1$–$C_6$ alkyl group, a hydroxy $C_1$–$C_6$ alkyl group, an amino group, or a group:

$-A^{102}-(B^{101})_n-R^{104}$ wherein $A^{102}$ is a $C_1$–$C_6$ alkylene group, $B^{101}$ is a carbonyl group or a group:

—CONHNHCO— n is 0 or 1, and $R^{104}$ is the same as defined above; and $R^{103}$ is a carboxy group or a carboxylate group, provided that at least one of $R^{101}$ and $R^{102}$ contains a $R^{104}$.

4. A cephalosporin derivative or its pharmaceutically acceptable salt thereof as claimed in claim 2, wherein $Y^{101}$ is an oxygen atom, $R^{101}$ is a group:

$-A^{101}-R^{104}$ wherein $A^{101}$ is a $C_1$–$C_6$ alkylene group which may have a carboxy group and $R^{104}$ is a group:

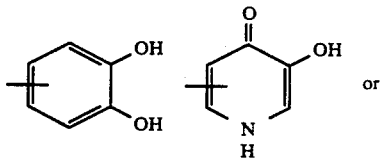 or

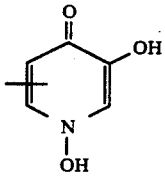

5. A cephalosporin derivative or its pharmaceutically acceptable salt thereof as claimed in claim 2, wherein $R^{101}$ is a $C_1$–$C_6$ alkyl group or a carboxy $C_1$–$C_6$ alkyl group.

6. A cephalosporin derivative or its pharmaceutically acceptable salt thereof as claimed in claim 4, wherein $R^{102}$ is a heterocyclic thiomethyl group which may have the substituent.

7. A cephalosporin derivative or its pharmaceutically acceptable salt thereof as claimed in claim 4, wherein $R^{102}$ is a hydrogen atom or a $C_1$–$C_6$ alkyl group.

8. A cephalosporin derivative or its pharmaceutically acceptable salt thereof as claimed in claim 6, wherein $R^{104}$ is a group:

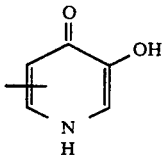

or

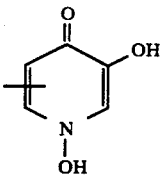

9. A cephalosporin derivative or its pharmaceutically acceptable salt thereof as claimed in claim 6, wherein $R^{104}$ is a group:

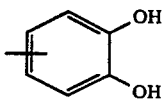

10. (6S,7S)-7-[(Z)-2-Aminothiazol-4-yl)-2-(1-carboxymethyl)-iminoacetamide]-3-{[1-[2-(3,4-dihydroxyphenyl)-2-oxo]ethyl]-4-pyridinio}thiomethyl-$\Delta^3$-O-2-isocephem-4-carboxylate according to claim 3.

11. (2S,7S)-7-[(Z)-2-(Aminothiazol-4-yl)-2-(1-carboxy-1-methylethoxy)iminoacetamide]-3-{[1-[2-(3,4-dihydroxyphenyl)-2-oxo]ethyl]-4-pyridinio}thiomethylisocephem-4-carboxylate or (6S,7S)-[(Z)-2-(2-aminothiazol-4-yl)-2-(1-carboxy-1-methylethoxy)imino]acetamide-3-[1-(N-3,4-dihydroxybenzamide)-carbamoylmethyl-4-pyridinio]thiomethylisocephem-4-carboxylate according to claim 5.

12. (6S,7S)-7-[(Z)-2-(2-Aminothiazol-4-yl)-2-(1,5-dihydroxy-4-pyridone-2-ylmethoxyimino)acetamide]-2-(1-carboxymethyl-1H-tetrazole-5-ylthiomethyl-)isocephem-4-carboxylic acid according to claim 8.

13. (6S,7S)-7-[(Z)-2-(2-Aminothiazol-4-yl)-2-( 1,5-dihydroxy-4-pyridone-2-ylmethoxyimino)acetamide]-3-[(5-carboxymethyl-4-methyl-thiazol-2-yl)thiomethyl-]isocephem-4-carboxylic acid.

14. An antimicrobial composition comprising an antimicrobially effective amount of a cepharosporin derivative represented by the general formula (1) in claim 1 or a pharmaceutically acceptable salt thereof, and a pharmaceutically acceptable carrier.

* * * * *